United States Patent
Heightman et al.

(10) Patent No.: US 7,615,550 B2
(45) Date of Patent: Nov. 10, 2009

(54) SUBSTITUTED PIPERAZINES,(1,4) DIAZEPINES, AND 2,5-DIAZABICYCLO (2.2.1)HEPTANES AS HISTAMINE H1 AND/OR H3 ANTAGONISTS OR HISTAMINE H3 REVERSE ANTAGONISTS

(75) Inventors: Thomas Daniel Heightman, Harlow (GB); Simon Teanby Hodgson, Stevenage (GB); Matthew J Lindon, Stevenage (GB); David Matthew Wilson, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 379 days.

(21) Appl. No.: 10/531,758

(22) PCT Filed: Oct. 14, 2003

(86) PCT No.: PCT/EP03/11423

§ 371 (c)(1), (2), (4) Date: Apr. 14, 2005

(87) PCT Pub. No.: WO2004/035556

PCT Pub. Date: Apr. 29, 2004

(65) Prior Publication Data

US 2006/0025404 A1    Feb. 2, 2006

(51) Int. Cl.
| | |
|---|---|
| *A61P 11/00* | (2006.01) |
| *A61P 25/00* | (2006.01) |
| *A61K 31/496* | (2006.01) |
| *C07D 243/08* | (2006.01) |
| *C07D 295/00* | (2006.01) |
| *C07D 307/85* | (2006.01) |
| *C07D 311/90* | (2006.01) |
| *C07D 317/68* | (2006.01) |
| *C07D 333/38* | (2006.01) |
| *C07D 401/12* | (2006.01) |
| *C07D 403/12* | (2006.01) |
| *C07D 405/06* | (2006.01) |
| *C07D 487/08* | (2006.01) |
| *C07D 491/04* | (2006.01) |

(52) U.S. Cl. ............ 514/227.8; 514/235.8; 514/252.11; 514/253.09; 514/253.1; 514/253.12; 544/60; 544/120; 544/357; 544/360; 544/364

(58) Field of Classification Search .............. 514/227.8, 514/235.8, 252.11, 253.09, 253.1, 253.12; 544/60, 120, 357, 360, 364
See application file for complete search history.

(56) References Cited

U.S. PATENT DOCUMENTS

| | | | |
|---|---|---|---|
| 3,996,361 | A | 12/1976 | Friebe et al. |
| 4,405,620 | A | 9/1983 | Buckle et al. |
| 5,364,791 | A | 11/1994 | Vegeto et al. |
| 5,874,534 | A | 2/1999 | Vegeto et al. |
| 5,880,128 | A | 3/1999 | Doll et al. |
| 5,935,934 | A | 8/1999 | Vegeto et al. |
| 2002/0137931 | A1 | 9/2002 | Bennani et al. |
| 2006/0019964 | A1 | 1/2006 | Ancliff et al. |

FOREIGN PATENT DOCUMENTS

| | | |
|---|---|---|
| DE | 4410822 | 9/1995 |
| JP | 2002-173426 | 6/2002 |
| WO | WO 95/25443 | 9/1995 |
| WO | WO 97/26252 | 7/1997 |
| WO | WO 99/41242 | 8/1999 |
| WO | 0206223 A1 | 1/2002 |
| WO | WO 02 06233 | 1/2002 |
| WO | WO 02 12190 | 2/2002 |
| WO | WO 02 12214 | 2/2002 |
| WO | 02055496 A1 | 7/2002 |
| WO | WO 02 076925 | 10/2002 |
| WO | WO 03 059341 | 7/2003 |
| WO | WO 03 066604 | 8/2003 |
| WO | WO 2004/094441 | 11/2004 |

OTHER PUBLICATIONS

Leurs et al., Trends Pharmacol. Sci. 19:177-183 (1998).
Schlicker et al., Fundam. Clin. Pharmacol. 8:128-137 (1994).
Onodera et al., In: The Histamine H3 Receptor, ed Leurs and Timmerman, pp. 255-267, Elsevier Science B.V. (1998).
Giovanni et al., Behav. Brain Res. 104:147-155 (1999).
Hill et al., Pharmacol. Rev. 49:253-278 (1997).
Aaronson, Ann. Allergy 67:541-547 (1991).
Varty & Hey, Eur. J. Pharmacol. 452:339-345 (2002).
Hey et al., Arzneim-Forsch Drug Res. 48:881-888 (1998).
McLeod et al., Am. J. Rhinol. 13:391-399 (1999).
Chem. Pharm. Bull, 49(10):1314 (2001) (Abstract).
Lovenberg et al., Mol. Pharmacol. 55:1101-1107 (1999).
Taylor-Clark et al., "Histamine receptors that influence blockage of the normal human nasal airway." British Journal of Pharmacology, 2005, vol. 144, pp. 867-874.
Varty, et al. "Activiation of histamine H3 receptors in human nasal mucosa inhibits sympathetic vasoconstriction." European Journal of Pharmacology, 2004, vol. 484, pp. 83-89.

*Primary Examiner*—Brenda L Coleman
(74) *Attorney, Agent, or Firm*—James P. Riek

(57) ABSTRACT

The present invention relates to novel piperazine and azepine derivatives having pharmacological activity, processes for their preparation, to compositions containing them and to their use in the treatment of neurodegenerative disorders including Alzheimer's disease.

19 Claims, No Drawings

SUBSTITUTED PIPERAZINES,(1,4) DIAZEPINES, AND 2,5-DIAZABICYCLO (2.2.1)HEPTANES AS HISTAMINE H1 AND/OR H3 ANTAGONISTS OR HISTAMINE H3 REVERSE ANTAGONISTS

This application is filed pursuant to 35 U.S.C. §371 as a U.S. National Phase Application of International Application No. PCT/EP2003/011423 filed 14 Oct. 2003, which claims priority from GB0224084.4 filed 16 Oct. 2002.

The present invention relates to novel piperazine and azepine derivatives having pharmacological activity, processes for their preparation, to compositions containing them and to their use in the treatment of neurodegenerative disorders including Alzheimer's disease.

WO 02/76925 (Eli Lilly) describes a series of compounds which are claimed to be histamine H3 antagonists. WO 02/055496 (GlaxoSmithKline) describes a series of piperidine and piperazine derivatives which are claimed to be inducers of LDL-receptor expression. WO 02/12214 (Ortho McNeil Pharmaceutical Inc) describes a series of substituted aryloxyalkylamines which are claimed to be histamine H3 antagonists.

The histamine H3 receptor is expressed in both the mammalian central nervous system (CNS), and in peripheral tissues (Leurs et al., (1998), Trends Pharmacol. Sci. 19, 177-183). Activation of H3 receptors by selective agonists or histamine results in the inhibition of neurotransmitter release from a variety of different nerve populations, including histaminergic, adrenergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

The present invention provides, in a first aspect, a compound of formula (I):

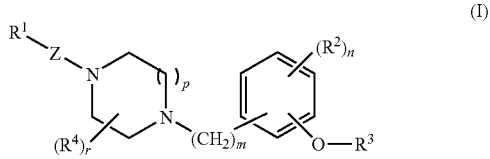

wherein:
$R^1$ represents hydrogen, -$C_{1-6}$ alkyl, -$C_{1-6}$ alkoxy, -$C_{3-8}$ cycloalkyl, -$C_{1-6}$ alkyl-$C_{3-8}$ cycloalkyl, aryl, heterocyclyl, heteroaryl, -$C_{1-6}$ alkyl-aryl, -$C_{1-6}$ alkyl-heteroaryl, -$C_{1-6}$ alkyl-heterocyclyl, -aryl-aryl, -aryl-heteroaryl, -aryl-heterocyclyl,-heteroaryl-aryl, -heteroaryl-heteroaryl, -heteroaryl-heterocyclyl, -heterocyclyl-aryl, -heterocyclyl-heteroaryl, -heterocyclyl-heterocyclyl, wherein $R^1$ may be optionally substituted by one or more substituents which may be the same or different, and which are selected from the group consisting of halogen, hydroxy, $COOR^{15}$, cyano, —$C_{1-6}$ alkyl-cyano, nitro, oxo, trifluoromethyl, trifluoromethoxy, fluoromethoxy, difluoromethoxy, $C_{1-6}$ alkyl (optionally substituted by a $COOR^{15}$ group), $C_{2-6}$ alkenyl (optionally substituted by a $COOR^{15}$ group), $C_{2-6}$ alkynyl (optionally substituted by a $COOR^{15}$ group), $C_{1-6}$ alkoxy (optionally substituted by a $COOR^{15}$ group), pentafluoroethyl, $C_{1-6}$ alkoxy, $C_{2-6}$ alkenoxy, aryl, aryl$C_{1-6}$ alkyl, —CO-aryl (optionally substituted by a halogen atom), —CO-heteroaryl, —$C_{1-6}$ alkyl-CO-aryl, aryl$C_{1-6}$ alkoxy, $C_{1-6}$ alkylthio, $C_{1-6}$ alkoxy$C_{1-6}$ alkyl, $C_{3-7}$ cycloalkyl, $C_{3-7}$ cycloalkyl$C_{1-6}$ alkoxy, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, sulfonyl, arylsulfonyl, arylsulfonyloxy, arylsulfonyl$C_{1-6}$ alkyl, aryloxy, $C_{1-6}$ alkylsulfonamido, $C_{1-6}$ alkylamido, $C_{1-6}$ alkylsulfonamido$C_{1-6}$ alkyl, $C_{1-6}$ alkylamido$C_{1-6}$ alkyl, arylsulfonamido, arylcarboxamido, arylsulfonamido$C_{1-6}$ alkyl, arylcarboxamido$C_{1-6}$ alkyl, aroyl, aroyl$C_{1-6}$ alkyl, aryl$C_{1-6}$ alkanoyl, or a group —$COR^{15}$, —$NR^{15}R^{16}$, —$CONR^{15}R^{16}$, —$NR^{15}COR^{16}$, —$NR^{15}SO_2R^{16}$ or —$SO_2NR^{15}R^{16}$, wherein $R^{15}$ and $R^{16}$ independently represent hydrogen, $C_{1-6}$ alkyl or $C_{3-6}$ cycloalkyl or together may be fused to form a 5- to 7-membered non-aromatic heterocyclic ring optionally interrupted by an O or S atom and optionally substituted by a halogen, $C_{1-6}$ alkyl or —$C_{1-6}$ alkyl$C_{1-6}$ alkoxy group;

Z represents a bond, CO, N($R^{10}$)CO or $SO_2$, such that when $R^1$ represents hydrogen, Z represents $NR^{10}CO$;

p is 1 or 2;

m, n and r independently represent 0, 1 or 2;

$R^2$ represents halogen, $C_{1-6}$ alkyl, $C_{1-6}$ alkoxy, cyano, amino or trifluoromethyl, such that when n represents 2, two $R^2$ groups may instead be linked to form a phenyl ring;

$R^4$ represents $C_{1-6}$ alkyl, or when r represents 2, two $R^4$ groups may instead together form a bridged $CH_2$, $(CH_2)_2$ or $(CH_2)_3$ group;

$R^{10}$ represents hydrogen or $C_{1-6}$ alkyl, or $R^{10}$, together with the nitrogen to which it is attached and $R^1$ forms a nitrogen containing heterocyclic group;

$R^3$ represents —$(CH_2)_q$—$NR^{11}R^{12}$ or a group of formula (i):

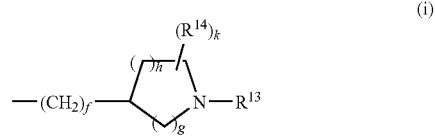

wherein q is 2, 3 or 4;

$R^{11}$ and $R^{12}$ independently represent $C_{1-6}$ alkyl or $C_{3-8}$ cycloalkyl or together with the nitrogen atom to which they are attached represent an N-linked nitrogen containing heterocyclyl group optionally substituted by one or more $R^{17}$ groups;

$R^{13}$ represents hydrogen, $C_{1-6}$ alkyl, —$C_{1-6}$ alkyl-$C_{1-6}$ alkoxy, $C_{3-6}$ cycloalkyl, —$C_{1-6}$ alkyl-$C_{3-8}$ cycloalkyl, —$C_{1-6}$ alkyl-aryl or heterocyclyl;

$R^{14}$ and $R^{17}$ independently represent halogen, $C_{1-6}$ alkyl, haloalkyl, OH, di$C_{1-6}$ alkylamino, $C_{1-6}$ alkoxy or heterocyclyl;

f and k independently represent 0, 1 or 2;

g is 0, 1 or 2 and h is 0, 1, 2 or 3, such that g and h cannot both be 0;

with the proviso that when m represents 1, n and r both represent 0 and $R^3$ represents —$(CH_2)_3$-N-piperidine or —$(CH_2)_3$-N(ethyl)$_2$, $R^1$—Z represents a group other than methyl, —CO—O—C(CH$_3$)$_3$ or benzyl;

and with the proviso that when m, n and r all represent 0, p represents 1, $R^3$ represents —$(CH_2)_3$-N-pyrrolidine or —$(CH_2)_3$-N-piperidine, $R^1$ represents benzyl, Z represents a group other than a bond;

and with the proviso that when m, n and r all represent 0, p represents 1, $R^3$ represents —$(CH_2)_3$-N-piperidine, $R^1$ represents isopropyl, Z represents a group other than a bond;

and with the proviso that when m represents 1, n and r both represent 0, p represents 1, $R^3$ represents—$(CH_2)_3$-N-piperidine, $R^1$ represents methyl, isopropyl, aryl or benzyl, Z represents a group other than a bond;

and with the proviso that when m and n both represent 0, $R^3$ represents —$(CH_2)_3$-N(ethyl)$_2$, p represents 1, r represents 2 and $R^1$ and $R^4$ both represent methyl, Z represents a group other than a bond;

or a pharmaceutically acceptable salt thereof.

In one particular aspect of the present invention, there is provided a compound of formula (I) as defined above wherein:

$R^1$ represents a group other than hydrogen, —$C_{1-6}$ alkoxy or —$C_{1-6}$ alkyl-$C_{3-8}$ cycloalkyl; and $R^1$ is optionally substituted by one or more substituents other than COOR$^{15}$, —$C_{1-6}$ alkyl-cyano, $C_{1-6}$ alkyl substituted by a COOR$^{15}$ group), $C_{2-6}$ alkenyl (optionally substituted by a COOR$^{15}$ group), $C_{2-6}$ alkynyl (optionally substituted by a COOR$^{15}$ group), $C_{1-6}$ alkoxy (optionally substituted by a COOR$^{15}$ group), $C_{2-6}$ alkenoxy, aryl, aryl$C_{1-6}$ alkyl, —CO-aryl (optionally substituted by a halogen atom), —CO-heteroaryl, —$C_{1-6}$ alkyl-CO-aryl or $C_{3-7}$ cycloalkyl; and $R^{15}$ and $R^{16}$ independently represent a group other than $C_{3-8}$ cycloalkyl or together may be fused to form an unsubstituted 5- to 7-membered non-aromatic heterocyclic ring optionally interrupted by an O or S atom; and r represents 0; and two $R^2$ groups are not linked to form a phenyl ring; and $R^{11}$ and $R^{12}$ independently represent a group other than $C_{3-8}$ cycloalkyl; and $R^{13}$ represents a group other than —$C_{1-6}$ alkyl-$C_{3-8}$ cycloalkyl.

In a second particular aspect of the present invention, there is provided a compound of formula (I) as defined above wherein m represents 0 or 2.

In a further particular aspect of the present invention, there is provided a compound of formula (I) as defined above wherein Z represents CO, CONR$^{10}$ or SO$_2$.

Alkyl groups, whether alone or as part of another group, may be straight chain or branched and the groups alkoxy and alkanoyl shall be interpreted similarly. Alkyl moieties are more preferably $C_{1-4}$ alkyl, eg. methyl or ethyl. The term 'halogen' is used herein to describe, unless otherwise stated, a group selected from fluorine, chlorine, bromine or iodine.

The term "aryl" includes single and fused rings wherein at least one ring is aromatic, for example, phenyl, naphthyl, tetrahydronaphthalenyl, indanyl or fluorenyl.

The term "heterocyclyl" is intended to mean a 4-7 membered monocyclic saturated or partially unsaturated ring or a 4-7 membered saturated or partially unsaturated ring fused to a benzene ring containing 1 to 3 heteroatoms selected from oxygen, nitrogen or sulphur. Suitable examples of such monocyclic rings include pyrrolidinyl, piperidinyl, piperazinyl, morpholinyl, thiomorpholinyl, tetrahydrofuranyl, diazepanyl, azepanyl and azocanyl. Suitable examples of benzofused heterocyclic rings include indolinyl, isoindolinyl, benzodioxolyl and dihydroisoquinolinyl.

The term "nitrogen containing heterocyclyl" is intended to represent any heterocyclyl group as defined above which contains a nitrogen atom.

The term "heteroaryl" is intended to mean a 5-7 membered monocyclic aromatic or a fused 8-11 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include furopyridinyl and benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia, age-related memory dysfunction, mild cognitive impairment, cognitive dysfunction, epilepsy, neuropathic pain, inflammatory pain, migraine, Parkinson's disease, multiple sclerosis, stroke and sleep disorders including narcolepsy, psychiatric disorders including schizophrenia, attention deficit hyperactivity disorder, depression and addiction; and other diseases including obesity, asthma, allergic rhinitis, nasal congestion, chronic obstructive pulmonary disease and gastro-intestinal disorders.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

Preferably, $R^1$ represents:

hydrogen;

$C_{1-6}$ alkyl (eg. methyl, methylbutyl, or propyl);

$C_{1-6}$ alkoxy (eg. —OC(CH$_3$)$_3$);

aryl (eg. phenyl, naphthyl, tetrahydronaphthyl, indanyl or fluorenyl);

heteroaryl (eg. benzofuranyl, indolyl, pyrazinyl, benzoxadiazolyl, thiadiazolyl, thienyl, pyrazolopyrimidinyl, pyrazolopyridinyl, benzothiazolyl, furopyridinyl, pyridyl, quinolinyl, isoquinolinyl, quinoxalinyl, cinnolinyl, thiazolyl, triazolyl, isoxazolyl, pyrimidinyl, naphthyridinyl, benzisoxazolyl or benzisothiazolyl);

heterocyclyl (eg. benzodioxolyl, pyrrolidinyl, piperidinyl, piperazinyl, morpholinyl, thiomorpholinyl, tetrahydrothiopyranyl, thiopyranyl, tetrahydropyranyl, dihydrobenzofuranyl, dihydrochromenyl and xanthenyl);

$C_{3-8}$ cycloalkyl (eg. cyclopropyl, cyclopentyl or cyclohexyl);

—$C_{1-6}$ alkyl-aryl (eg. benzyl);

—$C_{1-6}$ alkyl-$C_{3-8}$ cycloalkyl (eg. —CH$_2$-cyclopropyl);

—$C_{1-6}$ alkyl-heteroaryl (eg. —CH$_2$-pyridyl, —CH$_2$-tetrazolyl, —CH$_2$-triazolyl, —CH$_2$-isothiazolyl, —CH$_2$-thienyl or —CH$_2$-furanyl);

-aryl-heterocyclyl (eg. -phenyl-pyrrolidinyl);
-aryl-aryl (eg. -biphenyl);
-aryl-heteroaryl (eg. -phenyl-pyridyl, -phenyl-pyrrolyl or -phenyl-tetrazolyl); or
-heteroaryl-aryl (eg. -pyridyl-phenyl).

More preferably, $R^1$ represents unsubstituted phenyl.

Also more preferably, $R^1$ represents:

aryl (eg. phenyl); or heterocyclyl (eg. piperidinyl, piperazinyl, morpholinyl, thiomorpholinyl or tetrahydropyranyl).

Preferably, $R^1$ is optionally substituted by one or more (eg. 1, 2 or 3): halogen (eg. chlorine, fluorine or bromine); trifluoromethyl; —$C_{1-6}$ alkyl (eg. methyl, ethyl, isopropyl, propyl or t-butyl) optionally substituted by $COOR^{15}$ (eg. COOH, COOMe or COOEt); —$C_{1-6}$ alkoxy (eg. methoxy, butoxy, —OCH(Me)$_2$ or —OC(Me)$_3$) optionally substituted by $COOR^{15}$ (eg. COOH or COOMe); hydroxy; oxo; cyano; —$C_{1-6}$ alkyl-cyano (eg. —$CH_2$—CN); $C_{1-6}$ alkenyl (eg. ethenyl) optionally substituted by $COOR^{15}$ (eg. COOMe); $C_{3-7}$ cycloalkyl (eg. cyclopentyl); $C_{1-6}$ alkylsulfonyl (eg. —$SO_2$Me); $C_{1-6}$ alkenoxy (eg. —$OCH_2CH=CH_2$); $C_{1-6}$ alkylthio (eg. —S-ethyl); $NR^{15}R^{16}$ (eg. N(Me)$_2$); —$C_{1-6}$ alkyl-aryl (eg. benzyl); aryl (eg. phenyl); —CO-aryl (eg. —CO-phenyl) optionally substituted by halogen (eg. chlorine); —CO-heteroaryl (eg. —CO-azetidinyl); —CO-heterocyclyl (eg. —CO-tetrahydropyranyl); —$COOR^{15}$ (eg. COOH, COOMe or COOt-butyl); —$COR^{15}$ (eg. —CO-methyl, —CO-ethyl, —CO-isopropyl, —CO-cyclopropyl, —CO-cyclobutyl, —CO-cyclopentyl or —CO-cyclohexyl); —$CONR^{15}R^{16}$ (eg. —$CONH_2$, —CO-pyrrolidinyl, —CO-morpholinyl, —CO-piperazinyl, —CO-piperidinyl, —CO-thiomorpholinyl) optionally substituted by $C_{1-6}$ alkyl (eg. methyl), halogen (eg. fluorine) or —$C_{1-6}$ alkyl$C_{1-6}$ alkoxy (eg. —$CH_2$—OMe); or —$C_{1-6}$ alkyl-CO-aryl (eg. —$CH_2$COphenyl) groups.

More preferably, $R^1$ is optionally substituted by one or more (eg. 1, 2 or 3): halogen (eg. fluorine); oxo; cyano; —$CONR^{15}R^{16}$ (eg. —CO-pyrrolidinyl) or —$COR^{15}$ (eg. —CO-isopropyl, —CO-cyclopropyl or —CO-cyclobutyl).

Preferably, Z represents a bond, CO or $CONR^{10}$. More preferably, Z represents bond or CO, especially CO.

Preferably, $R^{10}$ represents hydrogen or $C_{1-6}$ alkyl.

Preferably, m is 0 or 2, more preferably 0.

Preferably, n is 0 or 1, more preferably n is 0.

When n represents 1, $R^2$ is preferably halogen (eg. chlorine, bromine or fluorine), trifluoromethyl, cyano or $C_{1-6}$ alkyl (eg. methyl).

Preferably, r is 0.

When r represents 1 or 2, $R^2$ is preferably $C_{1-6}$ alkyl (eg. methyl) or two $R^4$ groups together form a bridged $CH_2$ group.

Preferably, p is 1.

Preferably, $R^3$ represents —$(CH_2)_q$—$NR^{11}R^{12}$.

When $R^3$ represents a group of formula (i), preferably f is 0 or 1, g is 2, h is 1, k is 0 and $R^{13}$ represents hydrogen, optionally substituted $C_{1-6}$ alkyl (eg. ethyl, methylpropyl, isopropyl or methoxyethyl), $C_{3-8}$ cycloalkyl (eg. cyclopropyl, cyclobutyl or cyclopentyl) or —$C_{1-6}$ alkyl-$C_{3-8}$ cycloalkyl (eg. —$CH_2$-cyclopropyl).

When $R^3$ represents a group of formula (i), more preferably f is 0, g is 2, h is 1, k is 0 and $R^{13}$ represents $C_{1-6}$ alkyl (eg. isopropyl) or $C_{3-8}$ cycloalkyl (eg. cyclopropyl or cyclobutyl).

Preferably, q is 2 or 3, more preferably 3.

Preferably, $R^{11}$ and $R^{12}$ independently represent $C_{1-6}$ alkyl (eg. methyl) or $C_{3-8}$ cycloalkyl (eg. cyclopentyl) or $NR^{11}R^{12}$ represents a heterocyclic group (eg. piperidinyl, pyrrolidinyl, thiomorpholinyl, azepanyl or azocanyl optionally substituted by one or more halogen (eg. fluorine) or $C_{1-6}$ alkyl (eg. methyl or ethyl).

More preferably $NR^{11}R^{12}$ represents pyrrolidinyl, piperidinyl, azepanyl or azocanyl optionally substituted by one or more $C_{1-6}$ alkyl (eg. methyl or ethyl), especially unsubstituted piperidine.

Preferably, —O—$R^3$ is present at the para position of the phenyl group with respect to the rest of the compound.

Preferred compounds according to the invention include examples E1-E503 as shown below, or a pharmaceutically acceptable salt thereof.

Compounds of formula (I) may form acid addition salts with acids, such as conventional pharmaceutically acceptable acids, for example maleic, hydrochloric, hydrobromic, phosphoric, acetic, fumaric, salicylic, sulphuric, citric, lactic, mandelic, tartaric and methanesulphonic. Salts, solvates and hydrates of compounds of formula (I) therefore form an aspect of the invention.

Certain compounds of formula (I) are capable of existing in stereoisomeric forms. It will be understood that the invention encompasses all geometric and optical isomers of these compounds and the mixtures thereof including racemates. Tautomers also form an aspect of the invention. For example, when $R^3$ represents $(CH_2)_q NR^{11}R^{12}$ and $NR^{11}R^{12}$ represents a nitrogen containing heterocyclyl group substituted by one or more $C_{1-6}$ alkyl groups it will be appreciated that the present invention extends to cover diastereomeric and enantiomeric compounds.

The present invention also provides a process for the preparation of a compound of formula (I) or a pharmaceutically acceptable salt thereof, which process comprises:

(a) reacting a compound of formula (II)

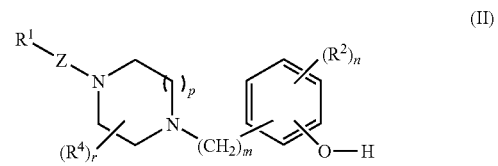

(II)

wherein $R^1$, Z, $R^4$, p, m, r, $R^2$ and n are as defined above, with a compound of formula $R^{3'}$—$L^1$, wherein $R^{3'}$ is as defined above for $R^3$ or a group convertible thereto and $L^1$ represents a suitable leaving group such as a halogen atom (eg. bromine or chlorine) or an optionally activated hydroxyl group; or (b) preparing a compound of formula (I) wherein Z represents CO by reacting a compound of formula (III)

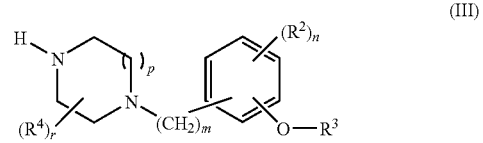

(III)

or a protected derivative thereof, wherein $R^4$, r, p, m, $R^2$, n and $R^3$ are as defined above, with a compound of formula $R^1$—COX, wherein $R^1$ is as defined above and X represents a suitable leaving group such as an activated hydroxy group, a suitable halogen atom or benzotriazolyl; or (c) preparing a compound of formula (I) wherein Z represents $SO_2$ by reacting a compound of formula (III) as defined above with a compound of formula R¹—SO₂Cl, wherein R¹ is as defined above; or (d) preparing a compound of formula (I) wherein Z represents NR¹⁰CO by reacting a compound of formula (III) as defined above with a compound of formula R¹—N=C=), wherein R¹ is as defined above; or (e) preparing a compound of formula (I) wherein Z represents CONR¹⁰ by reacting a compound of formula (III) as defined above, sequentially with phosgene in a solvent such as toluene followed by a compound of formula R¹⁰R¹—NH, in a solvent such as dichloromethane, wherein R¹ and R¹⁰ are as defined above; or (f) preparing a compound of formula (I) wherein m represents 1 by reacting a compound of formula (IV)

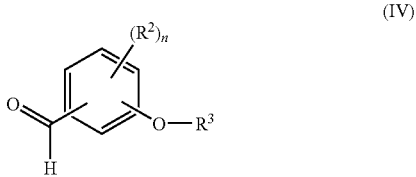

(IV)

with a compound of formula (XI)

(III)

or an optionally protected derivative thereof, wherein R⁴, r, R², n, R³, R¹, Z and p are as defined above under reducing conditions; or (g) deprotecting a compound of formula (I) which is protected; and (h) interconversion of other compounds of formula (I).

When R³ represents —(CH₂)$_q$—NR¹¹R¹², process (a) typically comprises the use of a suitable base, such as potassium carbonate in an appropriate solvent such as 2-butanone optionally in the presence of an activating reagent such as potassium iodide at an appropriate temperature such as reflux.

When a group R³' convertible to R³ represents, for example, L²—(CH₂)$_q$—, process (a) typically comprises an alkylation reaction using analogous conditions to those described above.

When R³ represents a group of formula (I) and L¹ represents an optionally activated hydroxyl group, process (a) typically comprises the use of a phosphine such as triphenylphosphine in a suitable solvent such as tetrahydrofuran, followed by addition of an azodicarboxylate such as diethylazodicarboxylate at a suitable temperature such as room temperature.

Process (b) typically comprises the use of an appropriate solvent such as dichloromethane optionally in the presence of an organic or inorganic base such as potassium carbonate or in the presence of a suitable coupling agent such as 1,3-dicyclohexylcarbodiimide and 1-hydroxybenzotriazole.

Processes (c) and (d) typically comprise the use of a suitable solvent such as 2-butanone.

Process (e) typically comprises the use of a suitable base, such as triethylamine.

Process (f) comprises the use of reductive conditions (such as treatment with a borohydride eg. sodium triacetoxyborohydride), optionally in the presence of an acid, such as acetic acid, followed by optional deprotection in the event that the compound of formula (XI) is a protected derivative.

In process (g), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxan or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—COCF₃) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (h) may be performed using conventional interconversion procedures such as epimerisation, oxidation, reduction, alkylation, nucleophilic or electrophilic aromatic substitution, ester hydrolysis or amide bond formation. For example, compounds of formula (I) wherein R³ represents a group of formula (i) may be interconverted at the R¹³ position by reaction with an alkyl halide such as 1-chloro-2-methoxyethane in the presence of a base such as potassium carbonate in a suitable solvent such as 2-butanone optionally in the presence of a transfer reagent such as potassium iodide. Such interconversion may also be carried out by reductive amination, for example, with acetone in the presence of a borohydride such as sodium triacetoxyborohydride and optionally an acid such as acetic acid in a suitable solvent such as dichloromethane.

Compounds of formula (II) and (III) wherein m is 1 or 2 may be prepared in accordance with the following scheme:

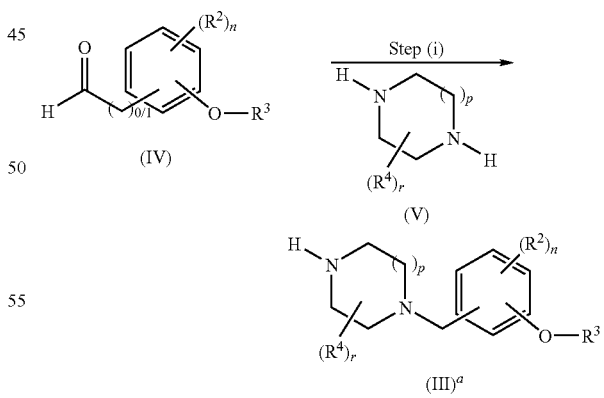

wherein R⁴, r, R², n, R³, p are as defined above and the compound of formula (V) may be optionally protected.

Step (i) may be performed in an analogous manner to that described for process (f) above.

Compounds of formula (III) wherein m is 0 may be prepared in accordance with the following scheme:

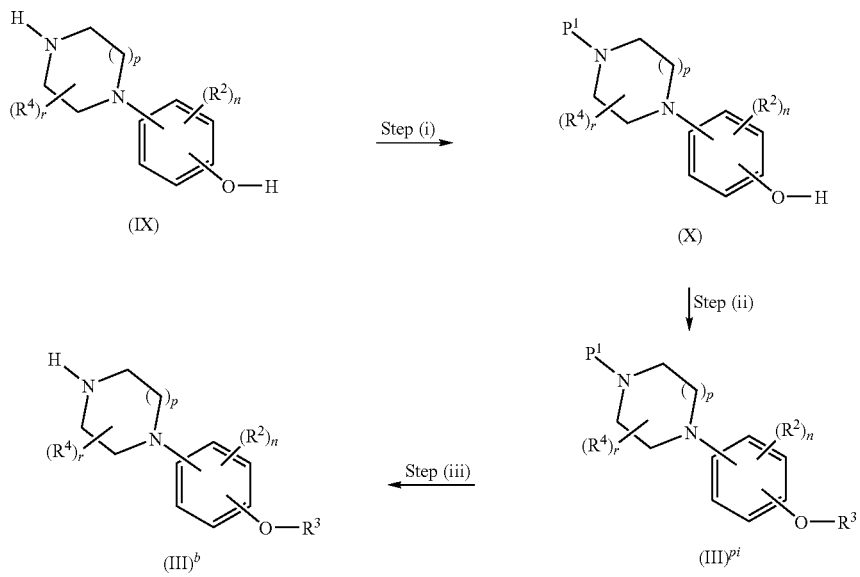

wherein $R^4$, r, p, $R^2$, n and $R^3$ are as defined above and $P^1$ represents a suitable protecting group (such as Boc).

Step (i) may be performed when $P^1$ represents Boc by reacting a compound of formula (IX) with di-t-butyl carbonate in the presence of a suitable base (eg. triethylamine) in the presence of a suitable solvent (eg. dichloromethane) at a suitable temperature (eg. room temperature).

Step (ii) may be performed in an analogous manner to the procedures shown below for the preparation of compounds of formula (IV).

Step (iii) typically comprises a deprotection reaction, for example, when $P^1$ represents Boc, deprotection may typically comprise reaction of a compound of formula $(III)^{pi}$ with hydrochloric acid in dioxan or trifluoroacetic acid in dichloromethane.

Compounds of formula (III) wherein m is 2 may be prepared in accordance with the following scheme:

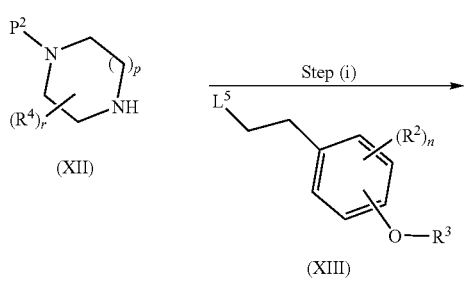

-continued

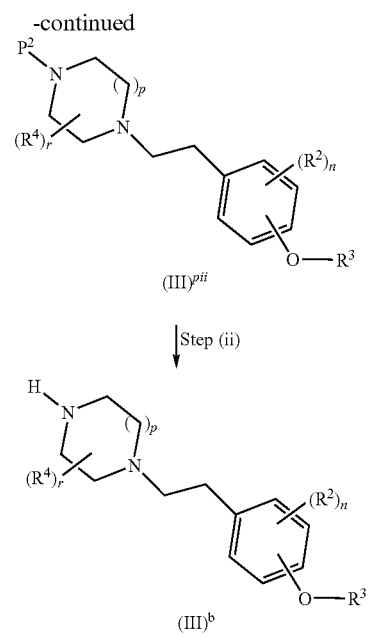

wherein $R^2$, $R^3$, $R^4$, n, p, r are as defined above, $P^2$ represents a suitable protecting group such as Boc and $L^5$ represents a suitable leaving group such as a halogen atom (eg. bromine).

Step (i) typically comprises reaction of a compound of formula (XII) with a compound of formula (XIII) in the presence of an inert solvent such as dimethylformamide or acetonitrile.

Step (ii) typically comprises a deprotection reaction, for example, when $P^2$ represents Boc, deprotection may typically comprise reaction of a compound of formula $(III)^{pii}$ with hydrochloric acid in dioxan or trifluoroacetic acid in dichloromethane.

Compounds of formula (IV) wherein $R^3$ represents $-(CH_2)_q-NR^{11}R^{12}$ may be prepared in accordance with the following scheme:

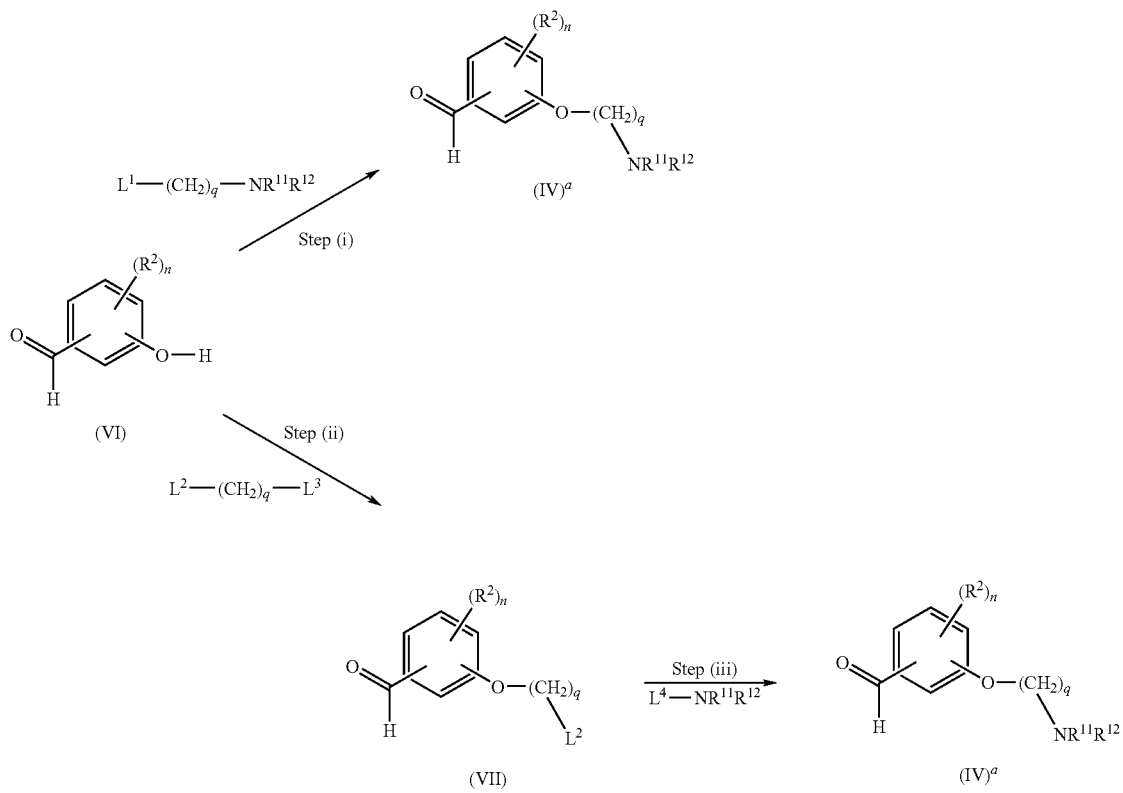

wherein $R^2$, n, q, $R^{11}$, $R^{12}$ are as defined above and $L^1$, $L^2$, $L^3$ and $L^4$ represent suitable leaving groups (eg. halogen atoms, such as bromine or chlorine).

Steps (i), (ii) and (iii) may be performed using similar conditions to those described for process (a) above.

Compounds of formula (IV) wherein $R^3$ represents a group of formula (i) as defined above may be prepared in accordance with the following scheme:

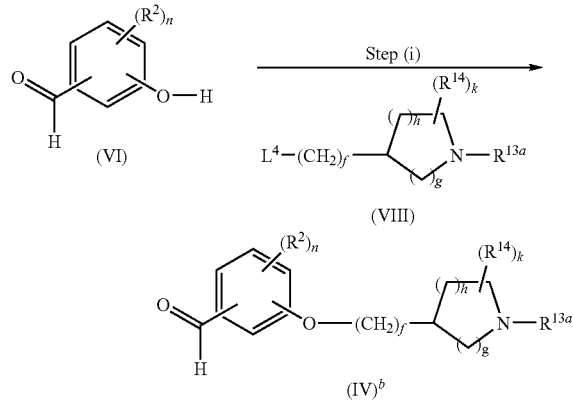

wherein $R^2$, n, f, g, h, k, are as defined above, $L^4$ represents a suitable leaving group such as a halogen atom or a hydroxyl group and $R^{13a}$ is as defined above for $R^{13}$ or a protecting group such as t-butoxycarbonyl, followed by optional deprotection.

Step (i) may be performed using similar conditions to those described for process (a) above.

Compounds of formula (II) wherein m is 0 may be prepared by a deprotection reaction of a compound of formula (IX) as defined above, followed by an analogous process to those described in processes (b), (c), (d) and (e) above, optionally followed by hydrolysis treatment to re-generate the free hydroxyl group of formula (II).

Compounds of formula (II) wherein m is 1 or 2 may be prepared from a compound of formula (IV) as defined above in an analogous process to that defined above to prepare compounds of formula (III)$^a$ followed by an analogous process to those described in processes (b), (c), (d) and (e) above, optionally followed by hydrolysis treatment to re-generate the free hydroxyl group of formula (II).

Compounds of formula (XI) may be prepared from the corresponding piperazine or diazepane by analogous procedures to those described in processes (b), (c), (d) and (e) above.

Compounds of formula (XI) wherein Z represents a bond may be prepared by reacting a compound of formula $R^1$—$L^6$ (wherein $R^1$ is as defined above and $L^6$ represents a suitable leaving group, eg. a bromine atom) with a compound of formula (XII), such as 1-BOC-piperazine, in the presence of a palladium catalyst, such as tris(dibenzylideneacetone) dipalladium, and a ligand such as 2-cyclohexylphosphino-2'-(N,N-dimethylamino)biphenyl, in an inert solvent such as tetrahydrofuran and in the presence of a base such as lithium bis(trimethylsilyl)amide in an inert atmosphere (nitrogen) and at elevated temperature such as 80° C., according to the procedure of Buchwald, Organic Letters, 2002, 4, 2885-2888.

Compounds of formula (V), (VI), (VIII), (IX), (XII) and (XIII) are either known or may be prepared in accordance with known procedures.

Certain compounds of formula (I), and their pharmaceutically acceptable salts have also been found to have affinity for the histamine H1 receptor.

Histamine H1 receptors are widely distributed throughout the CNS and periphery, and are involved in wakefulness and acute inflammatory processes [Hill et al, Pharmacol. Rev. 49:253-278 (1997)]. Seasonal allergic rhinitis, and other allergic conditions, are associated with the release of histamine from mast cells. The activation of H1 receptors in blood vessels and nerve endings are responsible for many of the symptoms of allergic rhinitis, which include itching, sneezing, and the production of watery rhinorrhea. Antihistamine compounds, i.e. drugs which are selective H1 receptor antagonists such as chlorphenyramine and cetirizine, are effective in treating the itching, sneezing and rhinorrhea associated with allergic rhinitis, but are not very effective in treating the nasal congestion symptoms [Aaronson, Ann. Allergy, 67:541-547, (1991)].

H3 receptor agonists are known to inhibit the effect of sympathetic nerve activation on vascular tone in porcine nasal mucosa [Varty & Hey. Eur. J. Pharmacol., 452:339-345, (2002)]. In vivo, H3 receptor agonists inhibit the decrease in nasal airway resistance produced by sympathetic nerve activation [Hey et al, Arzneim-Forsch Drug Res., 48:881-888 (1998)]. Furthermore, H3 receptor antagonists in combination with histamine H1 receptor antagonists reverse the effects of mast cell activation on nasal airway resistance and nasal cavity volume, an index of nasal congestion [McLeod et al, Am. J. Rhinol., 13: 391-399, (1999)]. A combined histamine H1 and H3 receptor antagonist, such as the series described herein, would be effective in the treatment of both the nasal congestion and the sneezing, itching and rhinorrhea associated with both seasonal and perennial allergic rhinitis.

Therefore, examples of disease states in which dual histamine H1 and H3 antagonists have potentially beneficial anti-inflammatory effects include diseases of the respiratory tract such as asthma (including allergic and non-allergic), allergic rhinitis, sinusitis, bronchitis (including chronic bronchitis), bronchiectasis, chronic obstructive pulmonary disease (COPD) and cystic fibrosis.

Other examples of disease states in which dual histamine H1 and H3 antagonists have potentially beneficial effects include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure.

Dual histamine H1 and H3 antagonists of the present invention may also be of use in the treatment of sleep/wake disorders, arousal/vigilance disorders, migraine, dementia, mild cognitive impairment (pre-dementia), cognitive dysfunction, Alzheimer's disease, epilepsy, narcolepsy, eating disorders, motion sickness, vertigo, attention deficit hyperactivity disorders, learning disorders, memory retention disorders, schizophrenia, depression, manic disorders, bipolar disorders and diabetes.

Diseases of principal interest for a dual histamine H1 and H3 antagonist include asthma, COPD and inflammatory diseases of the upper respiratory tract involving seasonal and perennial allergic rhinitis, non-allergic rhinitis, and the specific symptoms associated with these diseases including nasal congestion, rhinorrhoea, sneezing, cough and itching (pruritis) of eyes, ears, nose and throat. Other diseases of principal interest include cough, chronic urticaria, allergic conjunctivitis, nasal polyposis, sinusitis, psoriasis eczema and allergic dermatoses (including urticaria, atopic dermatitis, contact dermatitis, drug rashes and insect bites).

Diseases of principal interest include asthma, COPD, cognitive disorders and inflammatory diseases of the upper respiratory tract involving seasonal and perennial rhinitis.

Preferred diseases of principal interest include asthma, cognitive disorders and inflammatory diseases of the upper respiratory tract involving seasonal and perennial rhinitis.

Further diseases also of principal interest include inflammatory diseases of the gastrointestinal tract such as inflammatory bowel disease.

Thus the invention also provides a dual histamine H1 and H3 antagonist compound of formula (I) or a pharmaceutically acceptable salt thereof, for use as a therapeutic substance in the treatment or prophylaxis of the above disorders, in particular allergic rhinitis.

Preferred dual histamine H1 and H3 antagonist compounds of formula (I) are those wherein:

$R^1$ represents aryl (eg. phenyl, naphthyl or tetrahydronaphthyl) or heteroaryl (eg. benzofuranyl, indolyl or quinolinyl);

$R^1$ is optionally substituted by one or more (eg. 1, 2 or 3): halogen (eg. chlorine, fluorine or bromine); trifluoromethyl; —$C_{1-6}$ alkyl (eg. methyl, ethyl, isopropyl, propyl or t-butyl) optionally substituted by $COOR^{15}$ (eg. COOEt); —$C_{1-6}$ alkoxy (eg. methoxy) optionally substituted by $COOR^{15}$ (eg. COOMe); $C_{1-6}$ alkenyl (eg. ethenyl); $NR^{15}R^{16}$ (eg. $N(Me)_2$); or $C_{1-6}$ alkylthio (eg. —S-ethyl) groups;

Z is a bond or CO;

m is 0 or 2;

n is 0;

r is 0;

p is 1, $R^3$ represents —$(CH_2)_q$—$NR^{11}R^{12}$;

q represents 3; and $NR^{11}R^{12}$ represents pyrrolidinyl, piperidinyl, azepanyl or azocanyl optionally substituted by one or more $C_{1-6}$ alkyl (eg. methyl or ethyl), more preferably piperidinyl substituted by one or two methyl or ethyl groups.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (eg. sodium cromoglycate, nedocromil sodium, PDE-4 inhibitors, leukotriene antagonists, lipoxygenase inhibitors, chemokine antagonists (e.g CCR3, CCR1, CCR2, CXCR1, CXCR2 ), iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof), or sympathomimetics (e.g pseudoephedrine or oxymetazoline), or other antagonists at the histamine receptor (e.g H4), or cholinesterase inhibitors, or cholinergic antagonists, or antiinfective agents (eg. antibiotics, antivirals).

A pharmaceutical composition of the invention, which may be prepared by admixture, suitably at ambient temperature and atmospheric pressure, is usually adapted for oral, topical, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The compositiion may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Descriptions and Examples illustrate the preparation of compounds of the invention.

DESCRIPTION 1

4-[4-(3-Piperidin-1-yl-propoxy)-benzyl]-piperazine-1-carboxylic acid tert-butyl ester (D1)

To a solution of 4-(3-(piperidin-1-yl)propoxy)benzaldehyde (WO 02/12214 A2) (1.90 g, 7.68 mmol) in dichloromethane (25 ml) was added 1-N tert butoxy carbonyl piperazine (1.57 g, 8.45 mmol) followed by acetic acid (1 ml), and the reaction stirred for 1 hour at room temperature, then treated with sodium triacetoxy borohydride (2 g, 9.61 mmol) and stirred for 16 hours at room temperature. The reaction was then diluted with saturated sodium bicarbonate solution and extracted with dichloromethane. The dichloromethane was then washed sequentially with water and brine, dried over anhydrous sodium sulfate and evaporated in vacuo to yield a residue which was purified using silica gel chromatography eluting with a mixture of 0.880 ammonia:methanol:dichloromethane (0.5:4.5:95) to afford the title compound (1.586 g, 50%); MS (ES+), m/e 418 [M+H]$^+$.

DESCRIPTION 2

1-[4-(3-Piperidin-1-yl-propoxy)-benzyl]-piperazine trihydrochloride (D2)

To a solution of 4-[4-(3-piperidin-1-yl-propoxy)-benzyl]-piperazine-1-carboxylic acid tert-butyl ester (D1) (1.576 g, 3.76 mmol) in a (1:1) mixture of dichloromethane and methanol (20 ml) was added a 1M solution of hydrogen chloride in diethyl ether (20 ml) and the reaction stirred for 5 hours at room temperature. The solvent was then evaporated in vacuo and the resulting residue triturated with diethyl ether to afford the title compound (1.5 g, 93%); MS (ES+), m/e 318 [M+H]$^+$.

DESCRIPTION 3

4-[4-(3-Piperidin-1-yl-propoxy)-benzyl]-[1,4]diazepane-1-carboxylic acid tert-butyl ester (D3)

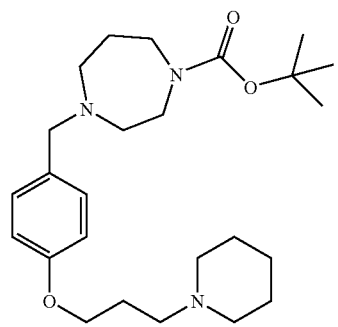

The title compound (D3) was prepared from [1,4]diazepane-1-carboxylic acid tert-butyl ester using the method of Description 1 (D1).

MS(ES+) m/e 432 [M+H]$^+$.

DESCRIPTION 4

1-[4-(3-Piperidin-1-yl-propoxy)-benzyl]-[1,4]diazepane (D4)

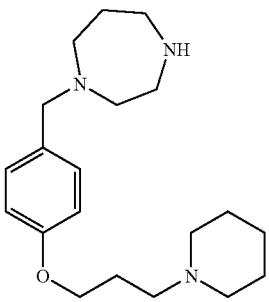

4-[4-(3-Piperidin-1-yl-propoxy)-benzyl]-[1,4]diazepane-1-carboxylic acid tert-butyl ester (D3) (2.27 g, 5.27 mmol) was dissolved in dichloromethane (10 ml), treated with trifluoroacetic acid (5 ml) and stirred at room temperature under argon for 2 hours. The solvent was removed in vacuo and the residue dissolved in methanol and passed down an SCX column (10 g) eluting with methanol followed by 0.88 ammonia/methanol (1:9). The basic fractions were combined and concentrated in vacuo to afford the title compound (1.57 g).

MS(ES+) m/e 332 [M+H]$^+$.

DESCRIPTION 5

4-(4-Formyl-phenoxy)-piperidine-1-carboxylic acid tert-butyl ester (D5)

4-Hydroxybenzaldehyde (2.0 g, 16.4 mmol) was dissolved in tetrahydrofuran (20 ml) and treated with 4-hydroxy-piperidine-1-carboxylic acid tert-butyl ester (4.1 g, 20.5 mmol) and by column chromatography on silica eluting with 4-1 hexane-ethyl acetate to afford the title compound as a colourless viscous oil (3.8 g)

MS (ES+) m/e 355 [M+H]$^+$.

DESCRIPTION 10

4-[4-(3-Piperidin-1-yl-propoxy)-phenyl]-piperazine-1-carboxylic acid tert-butyl ester (D10)

A mixture of 4-[4-(3-chloro-propoxy)-phenyl]-piperazine-1-carboxylic acid tert-butyl ester (D9) (4.0 g; 11.3 mM), piperidine (2.23 ml; 2 eq), potassium carbonate (3.73 g; 2.4 eq) and potassium iodide (3.74 g; 2 eq) in butan-2-one (100 ml) was heated at reflux for 3 days. The mixture was allowed to cool to room temperature, filtered and evaporated to give the title compound as a pale yellow solid (4.6 g)

MS (ES+) m/e 404 [M+H]$^+$.

DESCRIPTION 11

1-[4-(3-Piperidin-1-yl-propoxy)-phenyl]-piperazine (D11)

A solution of 4-[4-(3-piperidin-1-yl-propoxy)phenyl]-piperazine-1-carboxylic acid tert-butyl ester (D10) (1.0 g; 2.48 mM) in trifluoroacetic acid (5 ml) was stirred at room temperature for 60 minutes. The resulting mixture was purified on an SCX ion exchange cartridge to afford the title compound as a colourless crystalline solid (0.76 g)

MS (ES+) m/e 304 [M+H]$^+$.

DESCRIPTION 12

4-(3-Hydroxy-phenyl)-piperazine-1-carboxylic acid tert-butyl ester (D12)

Prepared from 3-piperazin-1-yl-phenol (Chem. Pharm. Bull. 49(10), 1314 (2001)) using the same method described in Description 8 (D8).

MS (ES+) m/e 279 [M+H]$^+$.

DESCRIPTION 13

4-[3-(3-Chloro-propoxy)-phenyl]-piperazine-1-carboxylic acid tert-butyl ester (D13)

Prepared from 4-(3-hydroxy-phenyl)-piperazine-1-carboxylic acid tert-butyl ester (D12) using the same method described in Description 9 (D9).

MS (ES+) m/e 355 [M+H]$^+$.

DESCRIPTION 14

4-[3-(3-Piperidin-1-yl-propoxy)-phenyl]-piperazine-1-carboxylic acid tert-butyl ester (D14)

Prepared from 4-[3-(3-chloro-propoxy)-phenyl]-piperazine-1-carboxylic acid tert-butyl ester (D13) using the same method described in Description 10 (D10).

MS (ES+) m/e 404 [M+H]$^+$.

DESCRIPTION 15

1-[3-(3-Piperidin-1-yl-propoxy)-phenyl]-piperazine (D15)

Prepared from 4-[3-(3-piperidin-1-yl-propoxy)-phenyl]-piperazine-1-carboxylic acid tert-butyl ester (D14) using the same method described in Description 11 (D11).

MS (ES+) m/e 304 [M+H]$^+$.

DESCRIPTION 16

4-Bromo-1-methyl-1H-indole (D16)

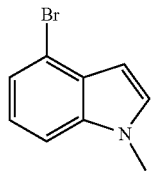

A solution of 4-bromo-1H-indole (6.7 g) in tetrahydrofuran (75 ml) was treated with sodium hydride (1.24 g) and stirred for 0.5 h at room temperature. The resulting suspension was treated with a solution of iodomethane (2.34 ml) in tetrahydrofuran (35 ml) at 0° C. and allowed to warm to room temperature over 1 h, whilst stirring. The reaction mixture was poured onto water and partitioned between dichloromethane and water. The organic phase was dried over (MgSO₄) and concentrated in vacuo to afford the title compound (7.2 g). TLC Silica (cyclohexane-ethyl acetate [1:1]), Rf=0.55.

DESCRIPTION 17

4-Bromo-1-methyl-1H-indole-3-carboxylic acid (D17)

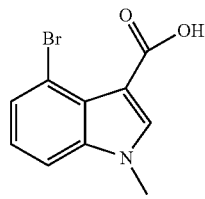

A solution of 4-bromo-1-methyl-1H-indole (D16) (7.0 g) in tetrahydrofuran (50 ml) was treated with a solution of trifluoroacetic anhydride (5.65 ml) in tetrahydrofuran (20 ml) at 0° C. The reaction mixture was allowed to warm to room temperature over 6 h, whilst stirring. The reaction mixture was concentrated in vacuo and then re-suspended in ethanol (25 ml). The solution was treated with 5N sodium hydroxide solution (50 ml) and heated under reflux for 18 h. The reaction mixture was washed with diethyl ether and the aqueous phase acidified with 5N hydrochloric acid solution. The precipitate was filtered, washed with water and concentrated in vacuo to afford the title compound (4.88 g). TLC, Silica (cyclohexane-ethyl acetate-acetic acid [3:1:0.1]), Rf=0.35.

DESCRIPTIONS 18-23

Descriptions 18-23 were prepared using analogous methods to Example 76b by substituting 2-methylpiperidine with the appropriate amine.

| Description | Structure | RT (min) | Mass Ion (M + H)⁺ |
|---|---|---|---|
| 18 | 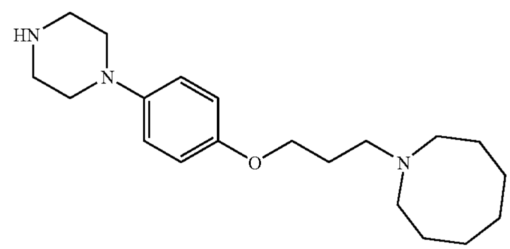 | 1.64 | 332 |
| 19 | 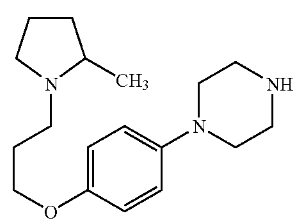 | 0.65 | 304 |
| 20 | 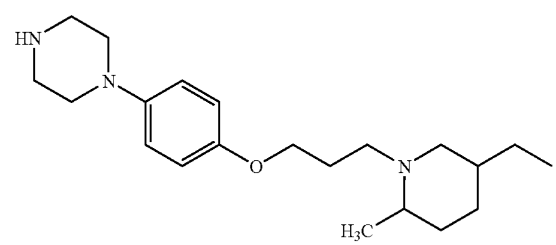 | 1.77 | 346 |
| 21 | 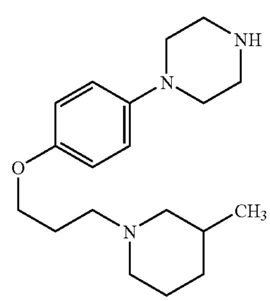 | 1.45 | 318 |

-continued

| Description | Structure | RT (min) | Mass Ion (M + H)+ |
|---|---|---|---|
| 22 | 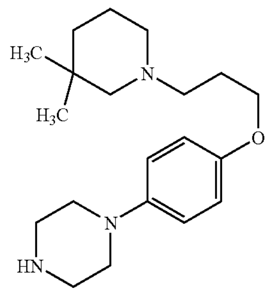 | 1.57 | 332 |
| 23 | 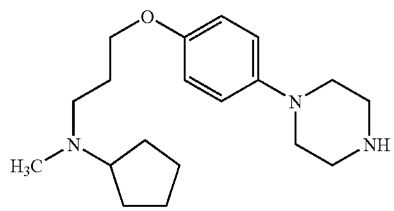 | 1.61 | 318 |

DESCRIPTIONS 24-32

Descriptions 24-32 were prepared by analogous methods to those indicated in the below table:

| Description | Name | Prepared analogously to | RT (min) |
|---|---|---|---|
| 24 | 1,1-Dimethylethyl 4-(2-naphthalenyl)-1-piperazinecarboxylate | E229a from known starting materials | 3.74 |
| 25 | 1,1-Dimethylethyl 4-(4-quinolinyl)-1-piperazinecarboxylate and 1,1-dimethylethyl 4-(3-quinolinyl)-1-piperazinecarboxylate (1:1) | E229a from known starting materials | 2.18 & 3.02 |
| 26 | 1-(2-Naphthalenyl)piperazine | E229b from known starting materials | 2.00 |
| 27 | 4-(1-Piperazinyl)quinoline and 3-(1-piperazinyl)quinoline (1:1) | E229b from D25 | 1.18 |
| 28 | 3-{[4-(2-Naphthalenyl)-1-piperazinyl]methyl}phenol | E229c from D24 | 2.39 |
| 29 | 3-{[4-(1-Naphthalenyl)-1-piperazinyl]methyl}phenol | E229c from D26 | 2.41 |
| 30 | 4-{[4-(8-Quinolinyl)-1-piperazinyl]methyl}phenol | E229c from E229b | 1.78 |
| 31 | 4-{[4-(4-Quinolinyl)-1-piperazinyl]methyl}phenol and 3-{[4-(3-quinolinyl)-1-piperazinyl]methyl}phenol (1:1) | E229c from D27 | 1.91 |
| 32 | 4-{[4-(1-Naphthalenyl)-1-piperazinyl]methyl}phenol | E229c from D26 | 2.46 |

DESCRIPTIONS 33-42

Descriptions 33-42 were prepared by analogous methods to those indicated in the below table:

| Description | Name | Prepared analogously to | RT (min) |
|---|---|---|---|
| 33 | 2-Methyl-4-[4-(2-{4-[(phenylmethyl)oxy]phenyl}ethyl)-1-piperazinyl]quinoline | E237a from known starting materials | 2.20 |
| 34 | 2-Methyl-4-[4-(2-{3-[(phenylmethyl)oxy]phenyl}ethyl)-1-piperazinyl]quinoline | E237a from known starting materials | 2.11 |
| 35 | 1-(1-Naphthalenyl)-4-(2-{4-[(phenylmethyl)oxy]phenyl}ethyl)piperazine | E237a from known starting materials | 2.91 |
| 36 | 1-(1-Naphthalenyl)-4-(2-{3-[(phenylmethyl)oxy]phenyl}ethyl)piperazine | E237a from known starting materials | 2.82 |
| 37 | 1-Phenyl-4-(2-{4-[(phenylmethyl)oxy]phenyl}ethyl)piperazine | E237a from known starting materials | 2.55 |
| 38 | 4-{2-[4-(2-Methyl-4-quinolinyl)-1-piperazinyl]ethyl}phenol | E237b from D33 | 1.69 |
| 39 | 3-{2-[4-(2-Methyl-4-quinolinyl)-1-piperazinyl]ethyl}phenol | E237b from D34 | 4.56 |
| 40 | 4-{2-[4-(1-Naphthalenyl)-1-piperazinyl]ethyl}phenol | E237b from D35 | 2.28 |
| 41 | 3-{2-[4-(1-Naphthalenyl)-1-piperazinyl]ethyl}phenol | E237b from D36 | 2.32 |
| 42 | 4-[2-(4-Phenyl-1-piperazinyl)ethyl]phenol | E237b from D37 | 2.02 |

DESCRIPTION 43

3-Bromo-4-ethyl-benzoic acid (D43)

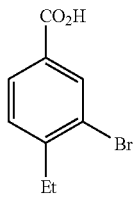

To a mixture of conc. HNO₃ (66 mL), glacial AcOH (300 mL) and water (50 mL), 4-ethyl-benzoic acid (15 g) was added, stirring vigorously, before treating with bromine (5.67 mL). Finally a solution of AgNO₃ (16.97 g) in water (50 mL) was added dropwise and the mixture was stirred vigorously for 2 h. The precipitate was collected by filtration, washed well with water, before being extracted with hot, saturated K₂CO₃ solution, and then treated with charcoal. The hot solution was filtered through kieselguhr and the solution was acidified to pH1 using conc. HCl. The resulting white precipitate was collected by filtration and dried in the vacuum oven overnight at 60° C. to afford the title compound (19.46 g).

NMR (CDCl₃) δ 1.26 (3H, t), 2.83 (2H, q), 7.34 (1H, d), 7.97 (1H, dd), 8.27 (1H, dd)

DESCRIPTION 44

Methyl 3-bromo-4-ethyl-bnzoate (D44)

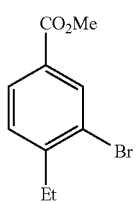

3-Bromo-4-ethyl-benzoic acid (D43) (19.40 g) was dissolved in MeOH (200 mL) and then treated with conc. H₂SO₄ (1 mL). The mixture was heated at reflux overnight, and then concentrated under reduced pressure. The residue was partitioned between EtOAc and saturated aqueous NaHCO₃ solution, extracting again with EtOAc. The combined extracts were then washed with brine, dried (MgSO₄). The solvent was evaporated in vacuo to afford the title compound (15.8 g). ¹H NMR (CDCl₃) δ 1.24 (3H, t), 2.79 (2H, q), 3.91 (3H, s), 7.29 (1H, d), 7.89 (1H, dd), 8.19 (1H, d).

DESCRIPTION 45

Methyl 3-cyano-4ethyl-benzoate (D45)

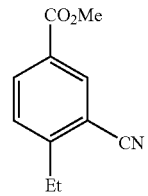

Methyl 3-bromo-4-ethyl-benzoate (D44) (5 g) in NMP (180 mL) was treated with copper (I) cyanide (3.69 g). The mixture was then heated at reflux for 5 h, under argon. After cooling to 20° C. the reaction mixture was diluted with water, then filtered through kieselguhr, washing well with water and EtOAc. The organic layer was washed with water, brine and dried over MgSO₄. The solvent was evaporated to dryness in vacuo and the residue was purified by chromatography on silica eluting with EtOAc-Hexane (1:9) to give the title compound (1.9 g) ¹H NMR (CDCl₃) δ 1.33 (3H, t), 2.94 (2H, q), 3.94 (3H, s), 7.43 (1H, d), 8.17 (1H, dd), 8.28 (1H, d).

DESCRIPTION 46

3-Cyano-4-ethyl benzoic acid (D⁴⁶)

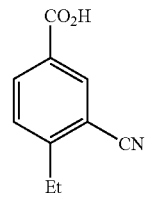

Methyl 3-cyano-4-ethyl-benzoate (D45) (1.92 g) was dissolved in MeOH (50 mL) before adding 1M NaOH solution (15.24 mL) and stirring the resulting mixture overnight at room temperature, under argon. The reaction mixture was diluted with water, and extracted with EtOAc. The aqueous layer was acidified to pH1 using 2M HCl before extracting with EtOAc. The combined extracts were washed with brine, dried over MgSO₄ and the solvent evaporated to dryness in vacuo to afford the title compound (1.63 g). ¹H NMR (CDCl₃) δ 1.35 (3H, t), 2.97 (2H, q), 7.49 (1H, d), 8.24 (1H, dd), 8.36 (1H, d).

Analysis of the Examples was performed as follows:

LCMS was conducted on a Supelcosil LCABZ+PLUS column (3.3 cm×4.6 mm ID) eluting with 0.1% formic acid and 0.01M ammonium acetate in water (solvent A) and 0.05% formic acid and 5% water in acetonitrile (solvent B), using the following elution gradient 0.0-7 min 0% B, 0.7-4.2 min 100% B, 4.2-5.3 min 0% B, 5.3-5.5 min 0% B at a flow rate of 3 mL/min. The mass spectra were recorded on a Fisons VG Platform spectrometer using electrospray positive and negative mode (ES+ve and ES−ve).

Preparative mass directed HPLC was conducted on a Waters FractionLynx system comprising of a Waters 600 pump with extended pump heads, Waters 2700 autosampler, Waters 996 diode array and Gilson 202 fraction collector on a 10 cm×2.54 cm ID ABZ+column, eluting with 0.1% formic acid in water (solvent A) and 0.1% formic acid in acetonitrile (solvent B), using an appropriate elution gradient, at a flow rate of 20 ml/min and detecting at 200-320 nm at room temperature. Mass spectra were recorded on Micromass ZMD mass spectrometer using electrospray positive and negative mode, alternate scans. The software used was MassLynx 3.5 with OpenLynx and FractionLynx options.

EXAMPLE 1

1-Phenyl-1-{4-[4-(3-piperidin-1-yl-propoxy)-benzyl]-piperazin-1-yl}-methanone (E1)

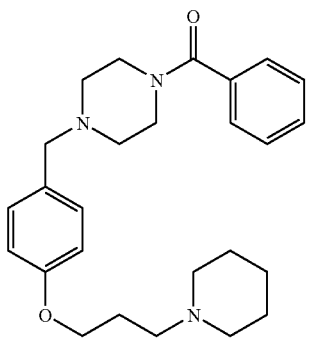

N-Cyclohexylcarbodiimide, N-methyl polystyrene HL (200-400 mesh) 1.8 mMol/g (650 mg, 1.172 mmol) was suspended in a (1:1) mixture of dichloromethane and dimethylformamide and treated sequentially with benzoic acid (72 mg, 0.58 mmol), 1-hydroxybenzotriazole hydrate (80 mg, 0.58 mmol) and stirred for 10 minutes at room temperature. A solution of 1-[4-(3-piperidin-1-yl-propoxy)-benzyl]-piperazine trihydrochloride (D2) (125 mg, 0.29 mmol) in dichloromethane (1 ml) and triethylamine (0.13 ml, 0.87 mmol) was then added to the reaction and stirred at room temperature for 16 hours. After filtration, the filtrate was applied to a Mega Bond elute SCX ion exchange column washing sequentially with water and methanol, followed by 0.880 ammonia/methanol (1:10) to elute the crude reaction mixture. Purification by silica gel chromatography eluting with a mixture of 0.880 ammonia:methanol:dichloromethane (0.5:4.5:95) to afford the title product (95 mg, 77%); MS (ES+), m/e 422 [M+H]$^+$.

EXAMPLES 2-11

Examples 2-11 (E2-E11) were prepared from Description 2 (D2) using an analogous method to that described in Example 1 (E1) by substituting benzoic acid for the appropriate acid indicated in the table.

| Example | Acid | Mass Spectrum |
|---|---|---|
| 1-Benzo[1,3]dioxol-5-yl-1-{4-[4-(3-piperidin-1-yl-propoxy)-benzyl]-piperazin-1-yl}-methanone (E2) | piperonylic acid | MS (ES+) m/e 466 [M + H]$^+$ |
| 1-Naphthalen-2-yl-1-{4-[4-(3-piperidin-1-yl-propoxy)-benzyl]-piperazin-1-yl}-methanone (E3) | 2-naphthoic acid | MS (ES+) m/e 472 [M + H]$^+$ |
| 1-(3,5-Dichloro-phenyl)-1-{4-[4-(3-piperidin-1-yl-propoxy)-benzyl]-piperazin-1-yl}-methanone (E4) | 3,5-dichlorobenzoic acid | MS (ES+) m/e 491/493 [M + H]$^+$ |
| 1-(4-Bromo-3-methyl-phenyl)-1-{4-[4-(3-piperidin-1-yl-propoxy)-benzyl]-piperazin-1-yl}-methanone (E5) | 3-methyl, 4-bromo benzoic acid | MS (ES+) m/e 515/517 [M + H]$^+$ |
| 1-(2-Methoxy-phenyl)-1-{4-[4-(3-piperidin-1-yl-propoxy)-benzyl]-piperazin-1-yl}-methanone (E6) | 2-methoxy benzoic acid | MS (ES+) m/e 452 [M + H]$^+$ |
| 1-(3,4-Dichloro-phenyl)-1-{4-[4-(3-piperidin-1-yl-propoxy)-benzyl]-piperazin-1-yl}-methanone (E7) | 3,4-dichloro benzoic acid | MS (ES+) m/e 491/493/495 [M + H]$^+$ |
| 4-(1-{4-[4-(3-Piperidin-1-yl-propoxy)-benzyl]-piperazin-1-yl}-methanoyl)-benzonitrile (E8) | 4-cyano benzoic acid | MS (ES+) m/e 447 [M + H]$^+$ |
| 1-(4-Fluoro-phenyl)-1-{4-[4-(3-piperidin-1-yl-propoxy)-benzyl]-piperazin-1-yl}-methanone (E9) | 4-fluoro benzoic acid | MS (ES+) m/e 440 [M + H]$^+$ |
| 1-(4-Bromo-phenyl)-1-{4-[4-(3-piperidin-1-yl-propoxy)-benzyl]-piperazin-1-yl}-methanone (E10) | 4-bromo benzoic acid | MS (ES+) m/e 500/502 [M + H]$^+$ |
| 1-Benzofuran-2-yl-1-{4-[4-(3-piperidin-1-yl-propoxy)-benzyl]-piperazin-1-yl}-methanone (E11) | 2-benzofuran carboxylic acid | MS (ES+) m/e 462 [M + H]$^+$ |

EXAMPLE 12

1-Benzo[1,3]dioxol-5-yl-1-{4-[4-(3-piperidin-1-yl-propoxy)-benzyl]-[1,4]diazopan-1-yl}-methanone (E12)

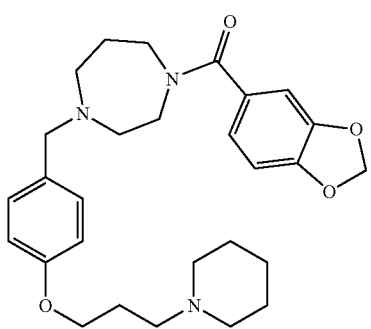

1-[4-(3-Piperidin-1-yl-propoxy)-benzyl]-[1,4]diazepane (D4) (100 mg, 0.30 mmol) was dissolved in dichloromethane (5 ml) and treated sequentially with benzo[1,3]dioxole-5-carboxylic acid (125 mg, 0.75 mmol), 1,3-dicyclohexylcarbodiimide (155 mg, 0.75 mmol) and 1-hydroxybenzotriazole hydrate (101 mg, 0.75 mmol). The mixture was allowed to stir at room temperature under argon for 12 hours, diluted with methanol and passed down an SCX ion exchange column (2 g) eluting with methanol followed by 0.880 ammonia/methanol (1:9). The basic fractions were combined and concentrated in vacuo to afford the title compound (127 mg). MS(ES+) m/e 480 [M+H]$^+$.

EXAMPLES 13-15

Examples 13-15 (E13-E15) were prepared from Description 4 (D4) using an analogous method to that described in Example 12 (E12) by substituting benzo[1,3]dioxole-5-carboxylic acid for the appropriate acid indicated in the table.

| Example | Carboxylic acid | Mass Spectrum |
|---|---|---|
| 1-Phenyl-1-{4-[4-(3-piperidin-1-yl-propoxy)-benzyl]-[1,4]diazepan-1-yl}-methanone (E13) | Benzoic acid | MS(ES+) m/e 436 [M + H]$^+$ |
| 1-Naphthalen-2-yl-1-{4-[4-(3-piperidin-1-yl-propoxy)-benzyl]-[1,4]diazepan-1-yl}-methanone (E14) | Naphthalene-2-carboxylic acid | MS(ES+) m/e 486 [M + H]$^+$ |
| 1-(3,5-Dichloro-phenyl)-1-{4-[4-(3-piperidin-1-yl-propoxy)-benzyl]-[1,4]diazepan-1-yl}-methanone (E15) | 3,5-Dichloro-benzoic acid | MS(ES+) m/e 505 [M + H]$^+$ |

EXAMPLES 16-23

Examples 16-23 (E16-E23) were prepared from Description 4 (D4) using an analogous method to that described in Example 12 (E12) by substituting benzo[1,3]dioxole-5-carboxylic acid for the appropriate acid indicated in the table followed by further purification by column chromatography on silica gel eluting with a mixture of 0.880 ammonia/methanol/dichloromethane (0.5:4.5:95).

| Example | Carboxylic acid | Mass Spectrum |
|---|---|---|
| 1-(4-Bromo-3-methyl-phenyl)-1-{4-[4-(3-piperidin-1-yl-propoxy)-benzyl]-[1,4]diazepan-1-yl}-methanone (E16) | 4-Bromo-3-methyl-benzoic acid | MS(ES+) m/e 529 [M + H]$^+$ |
| 1-(2-Methoxy-phenyl)-1-{4-[4-(3-piperidin-1-yl-propoxy)-benzyl]-[1,4]diazepan-1-yl}-methanone (E17) | 2-Methoxy-benzoic acid | MS(ES+) m/e 466 [M + H]$^+$ |
| 4-(1-{4-[4-(3-Piperidin-1-yl-propoxy)-benzyl]-[1,4]diazepan-1-yl}-methanoyl)-benzonitrile (E18) | 4-Cyano-benzoic acid | MS(ES+) m/e 461 [M + H]$^+$ |
| 1-(4-Fluoro-phenyl)-1-{4-[4-(3-piperidin-1-yl-propoxy)-benzyl]-[1,4]diazepan-1-yl}-methanone (E19) | 4-Fluoro-benzoic acid | MS(ES+) m/e 454 [M + H]$^+$ |
| 1-(4-Bromo-phenyl)-1-{4-[4-(3-piperidin-1-yl-propoxy)-benzyl]-[1,4]diazepan-1-yl}-methanone (E20) | 4-Bromo-benzoic acid | MS(ES+) m/e 515 [M + H]$^+$ |
| 1-Benzofuran-2-yl-1-{4-[4-(3-piperidin-1-yl-propoxy)-benzyl]-[1,4]diazepan-1-yl}-methanone (E21) | Benzofuran-2-carboxylic acid | MS(ES+) m/e 476 [M + H]$^+$ |
| 1-(3,4-Dichloro-phenyl)-1-{4-[4-(3-piperidin-1-yl-propoxy)-benzyl]-[1,4]diazepan-1-yl}-methanone (E22) | 3,4-Dichloro-benzoic acid | MS(ES+) m/e 505 [M + H]$^+$ |
| 1-Cyclopropyl-1-{4-[4-(3-piperidin-1-yl-propoxy)-benzyl]-[1,4]diazepan-1-yl}-methanone (E23) | Cyclopropane carboxylic acid | MS(ES+) m/e 400 [M + H]$^+$ |

EXAMPLE 24

1-Cyclopentyl-1-{4-[4-(3-piperidin-1-yl-propoxy)-benzyl]-[1,4]diazepan-1-yl}methanone (E24)

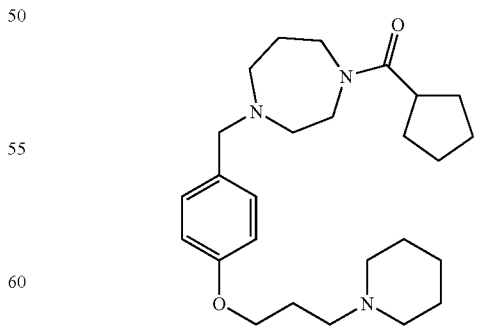

1-[4-(3-Piperidin-1-yl-propoxy)-benzyl]-[1,4]diazepane (D4) (100 mg, 0.30 mmol) was dissolved in dichloromethane (5 ml), treated with cyclopentyl acid chloride (80 mg, 0.60 mmol), potassium carbonate (83 mg, 0.60 mmol) and allowed to stir at room temperature under argon for 12 hours. The reaction mixture was diluted with methanol and passed down an SCX column (2 g) eluting with methanol followed by ammonia/methanol (1:9). The basic fractions were combined and concentrated in vacuo to afford the title compound (56 mg). MS(ES+) m/e 428 [M+H]+.

EXAMPLE 25

1-Benzenesulfonyl-4-[4-(3-piperidin-1-yl-propoxy)-benzyl]-[1,4]diazepane (E25)

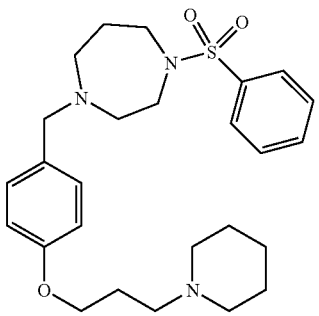

1-[4-(3-Piperidin-1-yl-propoxy)-benzyl]-[1,4]diazepane (D4) (100 mg, 0.30 mmol) was dissolved in 2-butanone (5 ml), treated with benzene sulfonyl chloride (57 mg, 0.32 mmol) and allowed to stir at room temperature under argon for 2 hours. The reaction mixture was diluted with methanol and passed down an SCX column (2 g) eluting with methanol followed by ammonia/methanol (1:9). The basic fractions were combined and concentrated in vacuo to afford the title compound (91 mg). MS(ES+) m/e 472 [M+H]+.

EXAMPLES 26-28

Examples 26-28 (E26-E28) were prepared from Description 4 (D4) using an analogous method to that described in Example 25 (E25) by substituting benzenesulfonyl chloride for the appropriate sulfonyl chloride indicated in the table.

| Example | Sulfonyl Chloride | Mass Spectrum |
| --- | --- | --- |
| 1-(Naphthalene-2-sulfonyl)-4-[4-(3-piperidin-1-yl-propoxy)-benzyl]-[1,4]diazepane (E26) | Naphthalene-2-sulfonyl chloride | MS(ES+) m/e 522 [M + H]+ |
| 1-(4-Fluoro-benzenesulfonyl)-4-[4-(3-piperidin-1-yl-propoxy)-benzyl]-[1,4]diazepane (E27) | 4-Fluoro-benzenesulfonyl chloride | MS(ES+) m/e 490 [M + H]+ |
| 1-(4-Bromo-benzenesulfonyl)-4-[4-(3-piperidin-1-yl-propoxy)-benzyl]-[1,4]diazepane (E28) | 4-Bromo-benzenesulfonyl chloride | MS(ES+) m/e 552 [M + H]+ |

EXAMPLES 29-31

Examples 29-31 (E29-E31) were prepared from Description 4 (D4) using an analogous method to that described in Example 25 (D25) by substituting benzenesulfonyl chloride for the appropriate sulfonyl chloride indicated in the table followed by further purification by column chromatography on silica gel eluting with a mixture of 0.880 ammonia/methanol/dichloromethane (0.5:4.5:95).

| Example | Sulfonyl Chloride | Mass Spectrum |
| --- | --- | --- |
| 1-(3,5-Dichloro-benzenesulfonyl)-4-[4-(3-piperidin-1-yl-propoxy)-benzyl]-[1,4]diazepane (E29) | 3,5-Dichloro-benzenesulfonyl chloride | MS(ES+) m/e 540 [M + H]+ |
| 1-(3,4-Dichloro-benzenesulfonyl)-4-[4-(3-piperidin-1-yl-propoxy)-benzyl]-[1,4]diazepane (E30) | 3,4-Dichloro-benzenesulfonyl chloride | MS(ES+) m/e 540 [M + H]+ |
| 4-{4-[4-(3-Piperidin-1-yl-propoxy)-benzyl]-[1,4]diazepane-1-sulfonyl}-benzonitrile (E31) | 4-Cyano-benzenesulfonyl chloride | MS(ES+) m/e 497 [M + H]+ |

EXAMPLE 32

1-Phenyl-1-{4-[4-(piperidin-4-yloxy)-benzyl]-piperazin-1-yl}-methanone (E32)

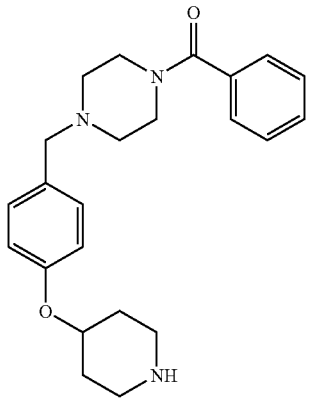

The title compound (E32) was prepared from 4-{4-[4-(1-phenyl-methanoyl)-piperazin-1-ylmethyl]-phenoxy}-piperidine-1-carboxylic acid tert-butyl ester (D7) using the method described in Description 4 (D4). MS(ES+) m/e 380 [M+H]+.

EXAMPLE 33

1-{4-[4-(1-Isopropyl-piperidin-4-yloxy)-benzyl]-piperazin-1-yl}-1-phenyl-methanone (E33)

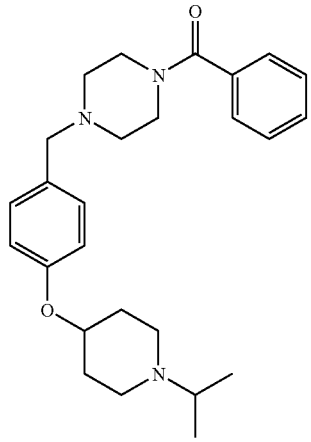

The title compound (E33) was prepared from 1-phenyl-1-{4-[4-(piperidin-4-yloxy)-benzyl]-piperazin-1-yl}-methanone (E32) and acetone using the method described in Description 1 (D1). MS(ES+) m/e 422 [M+H]$^+$.

EXAMPLE 34

1-(4-{4-[1-(2-Methoxy-ethyl)-piperidin-4-yloxy]-benzyl}-piperazin-1-yl)-1-phenyl-methanone (E34)

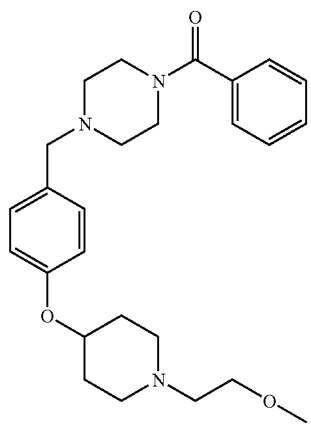

1-Phenyl-1-{4-[4-(piperidin-4-yloxy)-benzyl]-piperazin-1-yl}-methanone (E32) (150 mg, 0.40 mmol) was dissolved in 2-butanone and treated with 1-chloro-2-methoxy-ethane (0.08 ml, 0.80 mmol), potassium carbonate (132 mg, 0.96 mmol) and potassium iodide (159 mg, 0.96 mmol). The reaction mixture was heated under reflux for 24 hours. The mixture was allowed to cool to room temperature, acidified by the addition of glacial acetic acid and passed down an SCX ion exchange column (2 g) eluting with methanol followed by ammonia/methanol (1:9). The basic fractions were combined and concentrated in vacuo to afford the title compound (76 mg). MS(ES+) m/e 438 [M+H]$^+$.

EXAMPLES 35-37

Examples 35-37 (E35-E37) were prepared in accordance with the following general synthesis:

The appropriate acid chloride (1.1 eq) was added to a mixture of 1-[4-(3-piperidin-1-yl-propoxy)-phenyl]-piperazine (D11) (100 mg; 0.33 mM) and potassium carbonate (55 mg; 1.5 eq) in butan-2-one (2 ml). The resulting mixtures were stirred at room temperature for 3 hours and then purified on SCX ion exchange cartridges to afford the title compounds.

| Example | Acid Chloride | Mass Spectrum |
|---|---|---|
| 1-Cyclopropyl-1-{4-[4-(3-piperidin-1-yl-propoxy)-phenyl]-piperazin-1-yl}-methanone (E35) | Cyclopropane carbonyl chloride | MS (ES+) m/e 372 [M + H]$^+$. |
| 1-Phenyl-1-{4-[4-(3-piperidin-1-yl-propoxy)-phenyl]-piperazin-1-yl}-methanone (E36) | Benzoyl chloride | MS (ES+) m/e 408 [M + H]$^+$. |
| 1-(3,4-Dichloro-phenyl)-1-{4-[4-(3-piperidin-1-yl-propoxy)-phenyl]-piperazin-1-yl}-methanone (E37) | 3,4-Dichlorobenzoyl chloride | MS (ES+) m/e 477 [M + H]$^+$. |

EXAMPLES 38-39

Examples 38-39 (E38-E39) were prepared from 1-[3-(3-piperidin-1-yl-propoxy)-phenyl]-piperazine (D15) using the same procedure as described in Examples 36 and 37, respectively.

| Example | Mass Spectrum |
|---|---|
| 1-Phenyl-1-{4-[3-(3-piperidin-1-yl-propoxy)-phenyl]-piperazin-1-yl}-methanone (E38) | MS (ES+) m/e 408 [M + H]$^+$. |
| 1-(3,4-Dichloro-phenyl)-1-{4-[3-(3-piperidin-1-yl-propoxy)-phenyl]-piperazin-1-yl}-methanone (E39) | MS (ES+) m/e 477 [M + H]$^+$. |

EXAMPLES 40-42

Examples 40-42 (E40-E42) were prepared in accordance with the following general synthesis:

The appropriate sulphonyl chloride (1.1 eq) was added to a mixture of 1-[4-(3-piperidin-1-yl-propoxy)-phenyl]-piperazine (D11) (100 mg; 0.33 mM) and potassium carbonate (55 mg; 1.5 eq) in butan-2-one (2 ml). The resulting mixtures were stirred at room temperature for 3 hours and then purified on SCX ion exchange cartridges to afford the title compounds.

| Example | Sulfonyl Chloride | Mass Spectrum |
|---|---|---|
| 1-Methanesulphonyl-4-[4-(3-piperidin-1-yl-propoxy)-phenyl]-piperazine (E40) | Methane sulfonyl chloride | MS (ES+) m/e 382 [M + H]$^+$. |
| 1-Benzenesulphonyl-4-[4-(3-piperidin-1-yl-propoxy)-phenyl]-piperazine (E41) | Benzene sulfonyl chloride | MS (ES+) m/e 444 [M + H]$^+$. |
| 1-(3,4-Dichloro | 3,4- | MS (ES+) m/e |

-continued

| Example | Sulfonyl Chloride | Mass Spectrum |
|---|---|---|
| benzenesulphonyl)-4-[4-(3-piperidin-1-yl-propoxy)-phenyl]-piperazine (E42) | Dichlorobenzene sulfonyl chloride | 513 [M + H]+. |

EXAMPLES 43-45

Examples 43-45 (E43-E45) were prepared from 1-[3-(3-piperidin-1-yl-propoxy)-phenyl]-piperazine (D15) using the same procedure as described in Examples 40, 41 and 42, respectively.

| Example | Mass Spectrum |
|---|---|
| 1-Methanesulphonyl-4-[3-(3-piperidin-1-yl-propoxy)-phenyl]-piperazine (E43) | MS (ES+) m/e 382 [M + H]+. |
| 1-Benzenesulphonyl-4-[3-(3-piperidin-1-yl-propoxy)-phenyl]-piperazine (E44) | MS (ES+) m/e 444 [M + H]+. |
| 1-(3,4-Dichloro benzenesulphonyl)-4-[3-(3-piperidin-1-yl-propoxy)-phenyl]-piperazine (E45) | MS (ES+) m/e 513 [M + H]+. |

EXAMPLES 46-47

Examples 46-47 (E46-E47) were prepared in accordance with the following general synthesis:

The appropriate isocyanate (1.1 eq) was added to 1-[4-(3-piperidin-1-yl-propoxy)-phenyl]-piperazine (D11) (100 mg; 0.33 mM) in butan-2-one (2 ml). The resulting mixtures were stirred at room temperature for 3 hours and then purified on SCX ion exchange cartridges to afford the title compounds.

| Example | Isocyanate | Mass Spectrum |
|---|---|---|
| 4-[4-(3-Piperidin-1-yl-propoxy)-phenyl] piperazine-1-carboxylic acid phenylamide (E46) | Isocyanatobenzene | MS (ES+) m/e 423 [M + H]+. |
| 4-[4-(3-Piperidin-1-yl-propoxy)-phenyl] piperazine-1-carboxylic acid (3,4-dichloro-phenyl)-amide (E47) | 3,4-Dichloro isocyanato benzene | MS (ES+) m/e 492 [M + H]+. |

EXAMPLE 48

4-[4-(3-Piperidin-1-yl-propoxy)-phenyl] piperazine-1-carboxylic acid cyclopropylamide (E48)

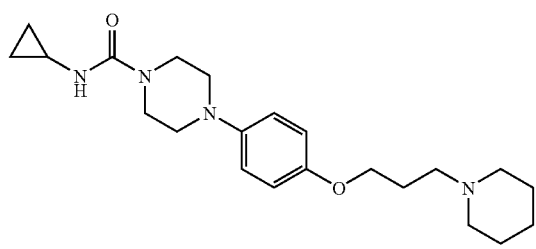

To a solution of 1-[4-(3-piperidin-1-yl-propoxy)-phenyl]-piperazine (D11) (150 mg, 0.49 mM) in dry dichloromethane (3 ml) was added drop wise a 20% solution of phosgene in toluene (0.5 ml; ~2 eq) and the resulting mixture stirred for 1 hour. The solvent was removed by evaporation and the resulting white powder dissolved in dry dichloromethane (4 ml). Triethylamine (0.14 ml: 2 eq) was added followed by cyclopropylamine (0.1 ml; 3 eq) and the mixture stirred for 18 hours. The solvent was removed by evaporation in vacuo and the residue purified on a silica column eluting with 3% methanol in dichloromethane to afford the title compound as a white solid (155 mg) MS (ES+) m/e 387 [M+H]+.

EXAMPLES 49-50

Examples 49-50 (E49-E50) were prepared from 1-[3-(3-piperidin-1-yl-propoxy)-phenyl]-piperazine (D15) using the same procedure as described in Examples 46 and 47, respectively.

| Example | Mass Spectrum |
|---|---|
| 4-[3-(3-Piperidin-1-yl-propoxy)-phenyl] piperazine-1-carboxylic acid phenylamide (E49) | MS (ES+) m/e 423 [M + H]+. |
| 4-[3-(3-Piperidin-1-yl-propoxy)-phenyl] piperazine-1-carboxylic acid (3,4-dichloro-phenyl)-amide (E50) | MS (ES+) m/e 492 [M + H]+. |

EXAMPLE 51

1-(3,4-Dichloro-phenyl)-4-[4-(3-Piperidin-1-yl-propoxy)-phenyl] piperazine (E51)

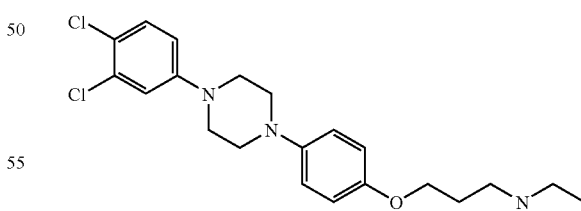

Tris(dibenzylidineacetone) di palladium (0) (5 mol %; 23 mg) was added to a mixture of 1-[4-(3-piperidin-1-yl-propoxy)-phenyl]-piperazine (D11) (150 mg; 0.49 mmol), 3,4- dichloro bromo benzene (160 mg; 1.2 eq), sodium tert-butoxide (71 mg; 1.1 eq) and racemic 2,2'-bis(diphenylphosphino)-1,1'-binaphthyl (7.5 mol %; 24 mg) in dry toluene (3 ml). The resulting mixture was heated at reflux under argon for 18 hours. The reaction was allowed to cool to room temperature and diluted with ethyl acetate (10 ml). The resulting solids were removed by filtration and the filtrate evaporated in vacuo. The residue was purified by column chromatography on silica eluting with 3% methanol in dichloromethane to afford the title compound as a buff solid (45 mg)

MS (ES+) m/e 448 [M+H]$^+$.

EXAMPLE 52

1-(3,4-Dichloro-phenyl)-4-[3-(3-Piperidin-1-yl-propoxy)-phenyl] piperazine (E52)

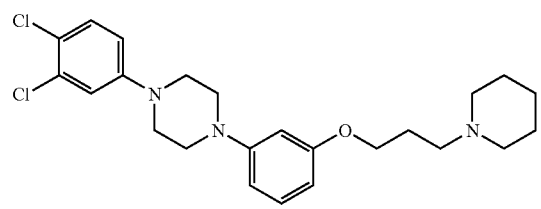

The title compound (E52) was prepared from 1-[3-(3-piperidin-1-yl-propoxy)-phenyl]-piperazine (D15) using the same method as described in Example 51 (E51).

MS (ES+) m/e 448 [M+H]$^+$.

EXAMPLE 53

5-Fluoro-1-methyl-3-{[4-(4-{[3-(1-piperidinyl)propyl]oxy}phenyl)-1-piperazinyl]carbonyl}-1H-indole (E53)

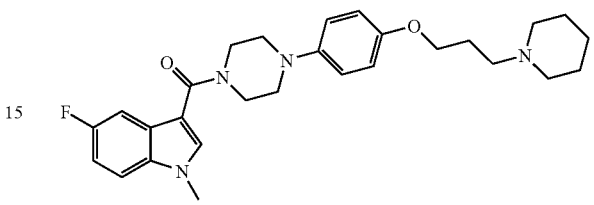

A solution of 5-fluoro-1-methyl-1H-indole-3-carboxylic acid [WO 0071537 A1] (35 mg) and 1-(4-{[3-(1-piperidinyl)propyl]oxy}phenyl)piperazine (D11) (50 mg) in dichloromethane (1 ml) was treated with benzotriazol-1-yloxytripyrrolidinophosphonium hexafluorophosphate (94.4 mg) and heated in a microwave (CEM™ Discover microwave) at 120° C. for 5 min. The reaction mixture was concentrated in vacuo and purified on a SCX cartridge (2 g) eluting with methanol-aqueous ammonia (10:1) followed by mass directed auto preparative HPLC to give the title compound (12 mg). LCMS RT=2.49 min, 478 (M+H)$^+$

EXAMPLES 54-61

The following compounds were prepared in an analogous manner to the process described for E53 from D11 and a known appropriate acid, with the exception of Example 57 which was prepared from D11 and D17.

| Example | Structure | RT (min) | Mass Ion (M + H)$^+$ |
|---|---|---|---|
| 54 | 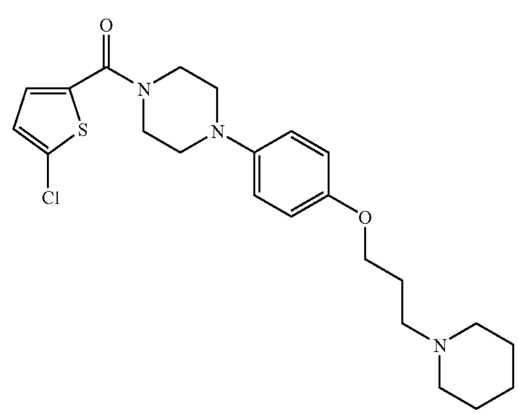 | 2.37 | 448 450 |

-continued

| Example | Structure | RT (min) | Mass Ion (M + H)+ |
|---|---|---|---|
| 55 | 5-fluoro-1H-indol-3-yl piperazine carbonyl, 4-(3-piperidin-1-ylpropoxy)phenyl; formic acid | 2.26 | 464 |
| 56 | 7-fluoro-1-methyl-1H-indol-3-yl piperazine carbonyl, 4-(3-piperidin-1-ylpropoxy)phenyl; formic acid | 2.41 | 478 |
| 57 | 4-bromo-1-methyl-1H-indol-3-yl piperazine carbonyl, 4-(3-piperidin-1-ylpropoxy)phenyl; formic acid | 2.40 | 539, 541 |
| 58 | 1,2-dimethyl-1H-indol-3-yl piperazine carbonyl, 4-(3-piperidin-1-ylpropoxy)phenyl; formic acid | 2.32 | 474 |

-continued
| Example | Structure | RT (min) | Mass Ion (M + H)+ |
|---|---|---|---|
| 59 | 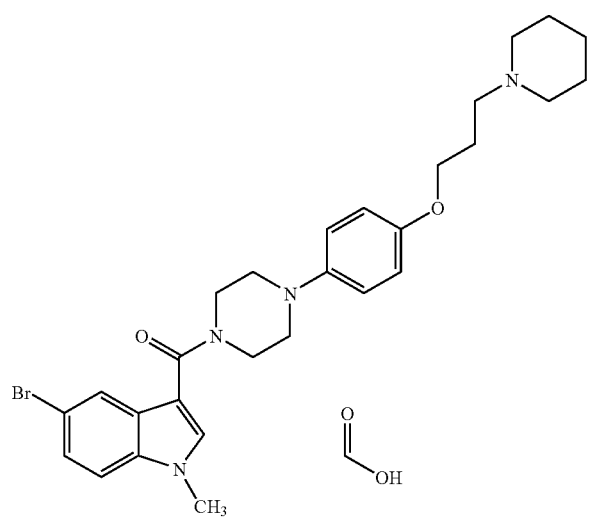 | 2.56 | 539 541 |
| 60 | 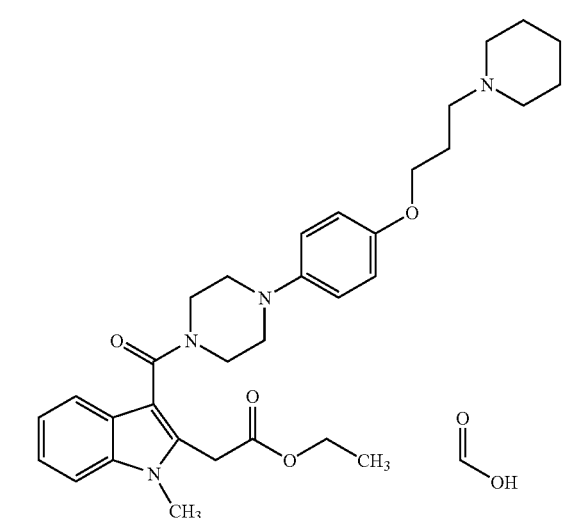 | 2.54 | 546 |
| 61 | 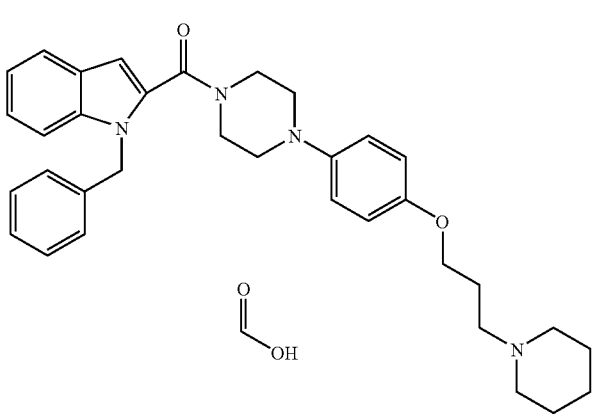 | 2.80 | 536 |

EXAMPLE 62

(1-Methyl-3-{[4-(4-{[3-(1-piperidinyl)propyl]oxy}phenyl)-1-piperazinyl]carbonyl}-1H-indol-2-yl)acetic acid (E62)

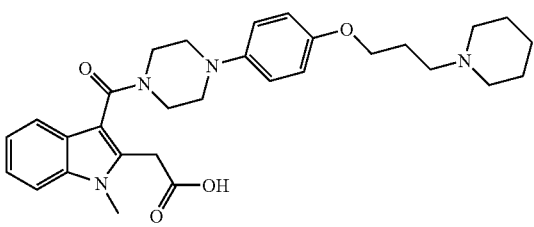

A solution of ethyl (1-methyl-3-{[4-(4-{[3-(1-piperidinyl)propyl]oxy}phenyl)-1-piperazinyl]carbonyl}-1H-indol-2-yl)acetate (E60) [54 mg] in methanol [6 ml] and water [0.8 ml] was treated with 2N sodium hydroxide [0.46 ml] and was heated under reflux for 2 h. The reaction mixture was quenched with hydrochloric acid [10 ml] at room temperature. The reaction mixture was concentrated in vacuo and partitioned between ethyl acetate and water. The organic phase was dried and concentrated in vacuo to give the title compound (20 mg). LCMS RT=2.35 min, 518 (M+H)+

EXAMPLE 63

1-(1-Naphthoyl)-4-[4-(3-piperidin-1-ylpropoxy)phenyl]piperazine trifluoroacetate (E63)

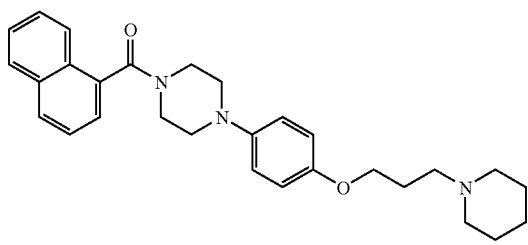

E63a: 4-[4-(1-Naphthoyl)piperazin-1-yl]phenol

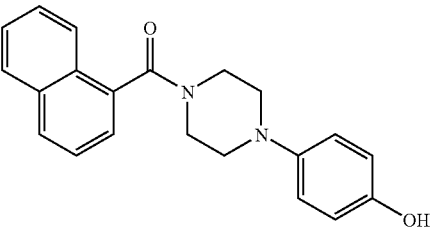

To a stirring mixture of 4-(1-piperazinyl)phenol (5.54 g) and triethylamine (10.83 ml) in dichloromethane (140 ml) was added dropwise, 1-naphthalenecarbonyl chloride (9.83 ml). The resulting reaction mixture was stirred under a nitrogen atmosphere for 3 h. The mixture was partitioned between dichloromethane and water and the organic phase was washed with saturated brine, dried (MgSO$_4$) and evaporated to dryness. The residue was suspended in 6:4 tetrahydrofuran-methanol (370 ml) and treated with a saturated solution of potassium carbonate in methanol (45 ml). The mixture was stirred at room temperature under a nitrogen atmosphere for 20 h. The solvent was evaporated and the residue was partitioned between dichloromethane and water. The organic phase was washed with saturated brine, dried (MgSO$_4$) and evaporated to give an oil (15.5 g), part of which (14.5 g) was purified by chromatography on a silica SPE bond elut cartridge eluting with 10% -80% ethyl acetate-cyclohexane gradient to give the title compound (8.9 g). LCMS RT=2.97 min.

E63b: 1-[4-(3-Chloropropoxy)phenyl]-4-(1-naphthoyl)piperazine

Was prepared from 4-[4-(1-naphthoyl)piperazin-1-yl]phenol (E63a) and 1-bromo-3-chloroproane using the same method described in Description 9 LCMS RT=3.59 min

E63c: 1-(1-Naphthoyl)-4-[4-(3-piperidin-1-ylpropoxy)phenyl]piperazine trifluoroacetate 1-[4-(3-Chloropropoxy)phenyl]-4-(1-naphthoyl)piperazine (E63b) (27 mg) piperidine (0.033 ml), potassium carbonate (46 mg), potassium iodide (56 mg)in 2-butanone (2 ml) was heated to reflux for 36 h. The solvent was removed at room temperature by a stream of nitrogen gas. The residue was dissolved in water and dichloromethane. The organic layer was separated, concentrated and purified by mass directed preparative HPLC to give the title compound (23 mg). LCMS RT=2.15 min, ES+ve m/z 458 (M+H)+.

EXAMPLES 64-75

Examples 64-75 were prepared in an array format using the same method described in Example 63c from 1-[4-(3-chloropropoxy)phenyl]-4-(1-naphthoyl)piperazine (0.067 mmol), the appropriate secondary amine (5.0 eq), potassium carbonate (5.0 eq), and potassium iodide (5.0 eq) in 2-butanone (2 ml). The products were purified by mass directed auto-preparative HPLC to provide the compounds as TFA salts.

| Example | Structure | RT (min) | Mass Ion (M + H)+ |
|---|---|---|---|
| 64 | 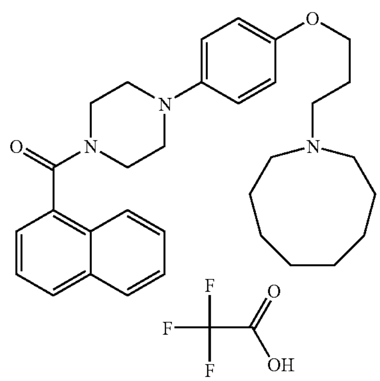 | 2.76 | 500 |
| 65 | 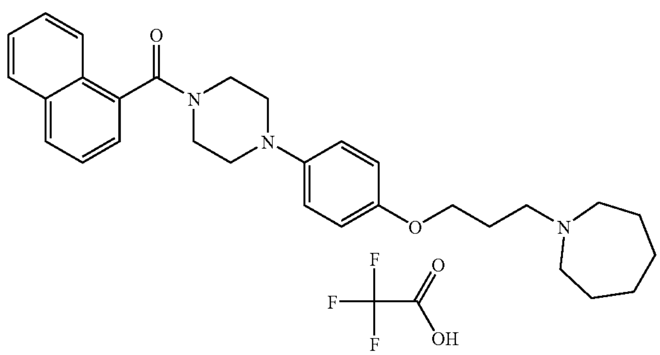 | 2.63 | 472 |
| 66 | 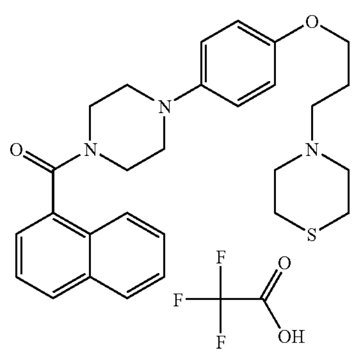 | 2.55 | 476 |
| 67 | 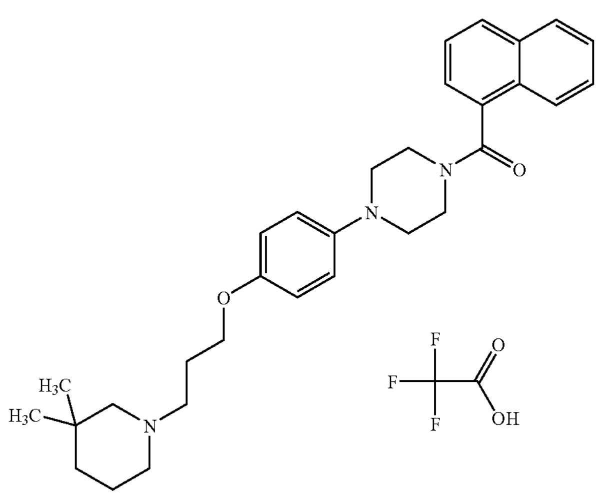 | 2.27 | 486 |

-continued

| Example | Structure | RT (min) | Mass Ion (M + H)+ |
|---------|-----------|----------|-------------------|
| 68 | 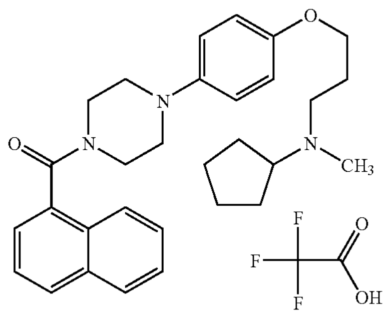 | 2.66 | 472 |
| 69 | 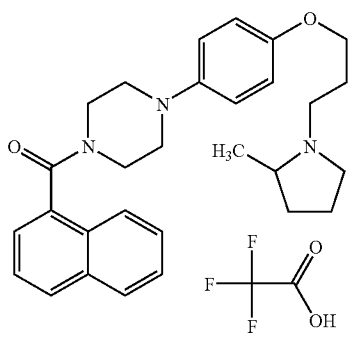 | 2.58 | 458 |
| 70 | 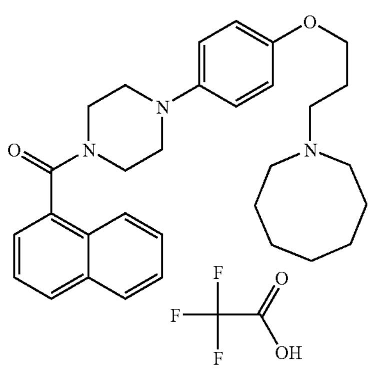 | 2.71 | 485.73 |
| 71 | 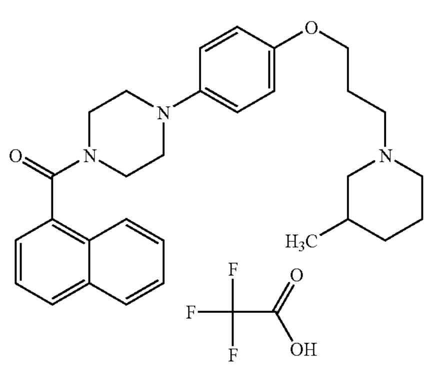 | 2.22 | 472 |

-continued

| Example | Structure | RT (min) | Mass Ion (M + H)+ |
|---|---|---|---|
| 72 | 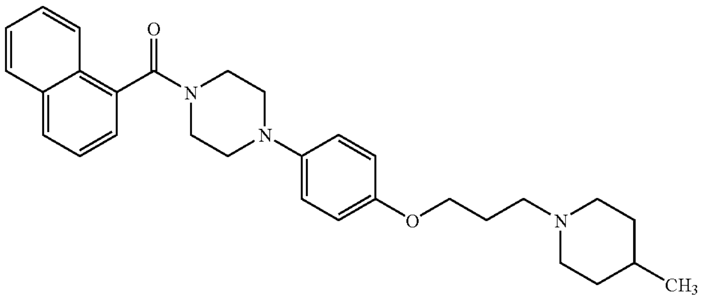 | 2.22 | 472 |
| 73 | 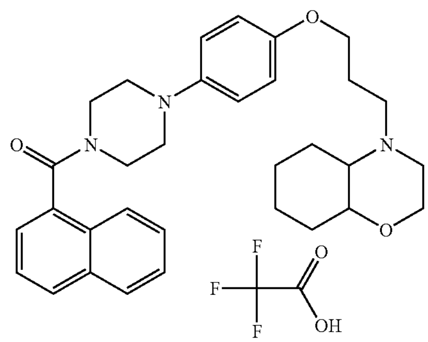 | 2.26 | 514 |
| 74 | 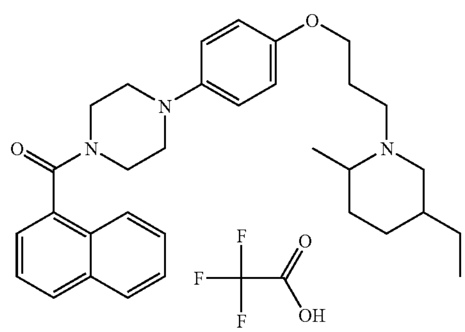 | 2.35 | 500 |
| 75 | 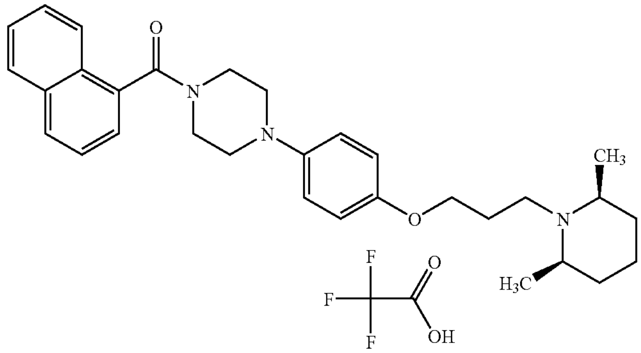 | 2.24 | 486 |

EXAMPLE 76

5-Fluoro-1-methyl-3-[(4-{4-[3-(2-methylpiperidin-1-yl)propoxy]phenyl}piperazin-1-yl)carbonyl]-1H-indole (E76)

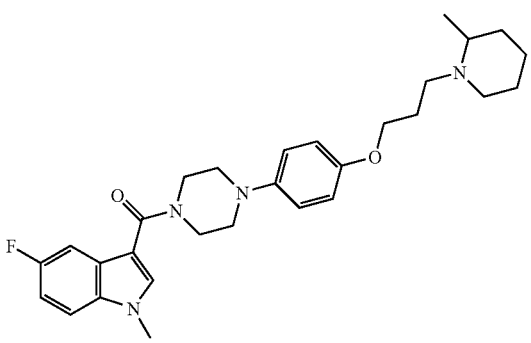

E76a: 1,1-Dimethylethyl 4-(4-{[3-(2-methyl-1-piperidinyl)propyl]oxy}phenyl)-1-piperazinecarboxylate

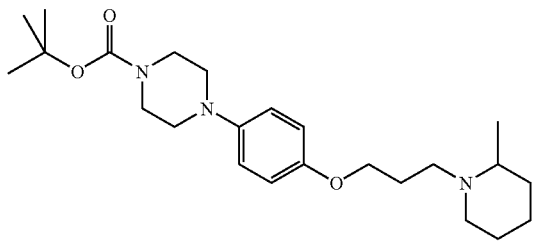

1,1-Dimethylethyl 4-{4-[(3-chloropropyl)oxy]phenyl}-1-piperazinecarboxylate (D9) (1.6 g), was dissolved in 2-butanone (10 ml). Potassium carbonate (1.38 g) and a catalytic amount of potassium iodide were added, followed by 2-methylpiperidine (0.99 g). The mixture was heated at reflux for 72 h under nitrogen. The reaction mixture was diluted with water and extracted with dichloromethane. The organic phases were separated using a hydrophobic frit, combined and evaporated in vacuo. The residue was purified on a 100 g silica SPE bond elut cartridge, eluting with a gradient of 0% to 20% [0.880 ammonia-methanol (1:9)]-dichloromethane mixtures, to give the title compound (1.66 g). LCMS RT=2.48 min.

E76b: 1-(4-{[3-(2-Methyl-1-piperidinyl)propyl]oxy}phenyl)piperazine

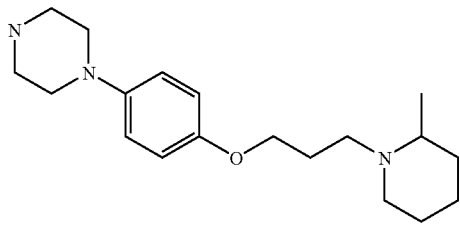

1,1-Dimethylethyl 4-(4-{[3-(2-methyl-1-piperidinyl) propyl]oxy}phenyl)-1-piperazinecarboxylate (E76a) (1.66 g) was dissolved in dry dichloromethane (25 ml) and stirred under nitrogen. 50% Trifluoroacetic acid in dichloromethane (5 ml) was added, and the mixture was stirred at room temperature for 4 h. Saturated sodium bicarbonate solution was then added and the mixture was extracted with dichloromethane. The organic phase was separated using a hydrophobic frit, and evaporated in vacuo, however, most of the product was in the aqueous phase. The product was removed from the aqueous phase using an OASIS cartridge, washing with water and eluting with methanol, and further purified using an aminopropyl bond elut cartridge, eluting with dichloromethane and then SCX cartridge, eluting with 50% [0.880 ammonia-methanol (1:9)]-dichloromethane to give the title compound (0.94 g). LCMS RT=1.01 min, ES+ve m/z=318 (M+H)+

E76c: 5-Fluoro-1-methyl-3-[(4-{4-[3-(2-methylpiperidin-1-yl)propoxy]phenyl}piperazin-1-yl)carbonyl]-1H-indole A solution of 5-fluoro-1-methyl-1H-indole-3-carboxylic acid (19.3 mg) and O-(1H-benzotriazol-1-yl)-N,N,N',N'-tetramethyluronium tetrafluoroborate (TBTU) (56 mg) in DMF (1 ml) and diisopropylethylamine (0.035 ml) was stirred for 10 min before 1-{4-[3-(2-methylpiperidin-1-yl)propoxy] phenyl}piperazine (E76b) (21.3 mg) in DMF (0.5 ml) was added. The mixture was stirred for 18 h and then concentrated under reduced pressure. The residue was purified by SPE ion exchange chromatography on an SCX-2 cartridge (1 g). The cartridge was washed with methanol (3 ml) and the product eluted with 2M ammonia in methanol (2.5 ml), to give the title compound (15 mg) LCMS RT=2.42 min, ES+ve m/z 493 (M+H)+.

EXAMPLES 77-224

Examples 77 to 224 were prepared in an array format in vials using a solution of the appropriate carboxylic acid (0.1 mmol) in DMF (0.5 ml) and a solution of O-(1H-benzotriazol-1-yl)-N,N,N',N'-tetramethyluronium tetrafluoroborate (TBTU) (0.15 mmol) in DMF (0.5 ml) and diisopropylethylamine (0.2 mmol). Each vial was shaken manually and stood for 10 min, before a solution of the appropriate piperazine (selected from D18-D23 or D46 in the case of Example 99) (0.067 mmol) in DMF (0.5 ml) was added to each reaction mixture. The vials were left to stand overnight for approximately 18 h at room temperature. Each solution was then added to the top of a preconditioned SCX-2 SPE cartridge (1 g). The cartridge was washed with methanol (3 ml) and the product eluted with 2M ammonia in methanol (2.5 ml), into pre-weighed vials. The solutions were evaporated to dryness on the genevac to provide the products (Examples 77-222). Examples 151, 154, 162-171 and 206-222 were further purified by mass directed auto-preparative HPLC to provide the products as trifluoroacetate salts.

| Example | Structure | RT (min) | Mass Ion (M + H)+ |
|---------|-----------|----------|-------------------|
| 77 | 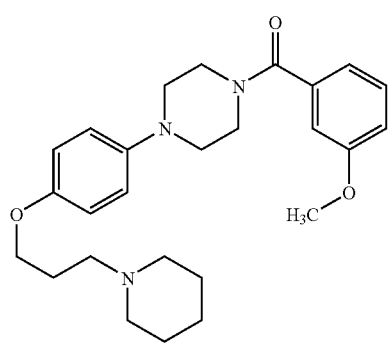 | 2.36 | 438 |
| 78 | 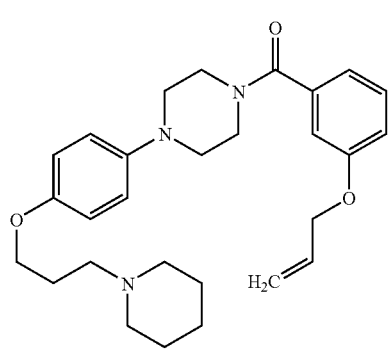 | 2.52 | 464 |
| 79 | 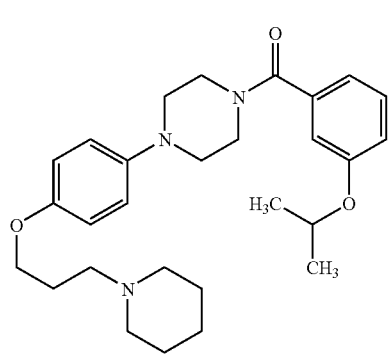 | 2.55 | 466 |
| 80 | 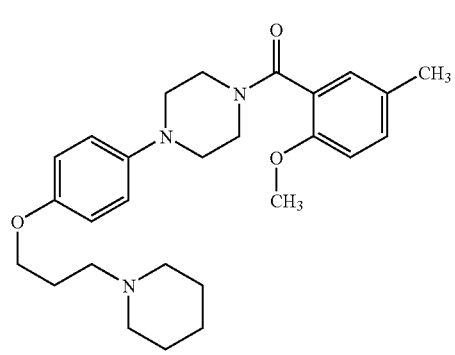 | 2.44 | 452 |

-continued

| Example | Structure | RT (min) | Mass Ion (M + H)+ |
|---------|-----------|----------|-------------------|
| 81 | 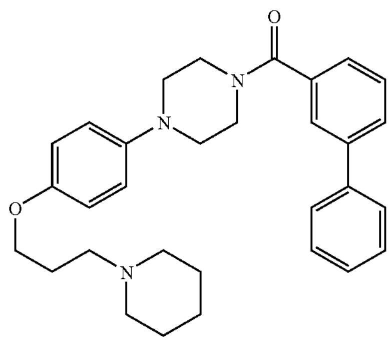 | 2.74 | 484 |
| 82 | 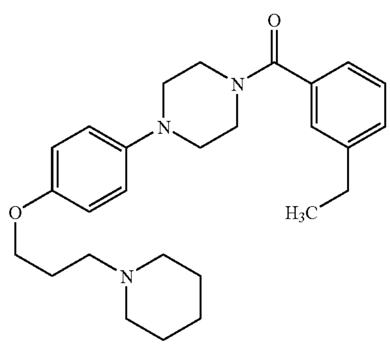 | 2.52 | 436 |
| 83 | 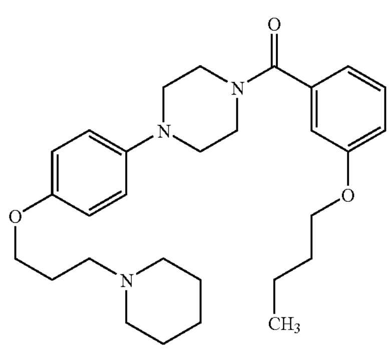 | 2.74 | 480 |
| 84 | 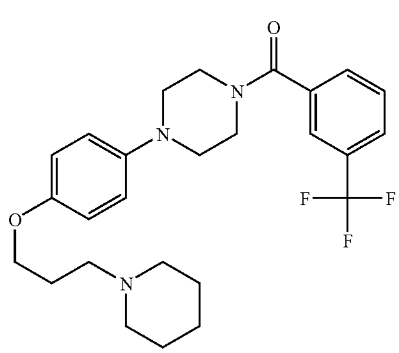 | 2.58 | 476 |

-continued

| Example | Structure | RT (min) | Mass Ion (M + H)+ |
|---------|-----------|----------|-------------------|
| 85 | 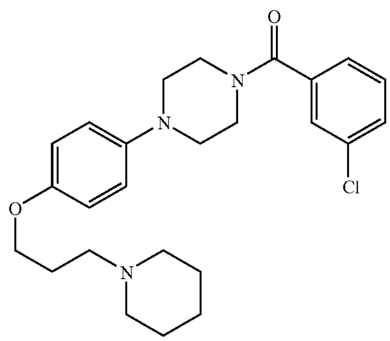 | 2.50 | 442<br>444 |
| 86 | 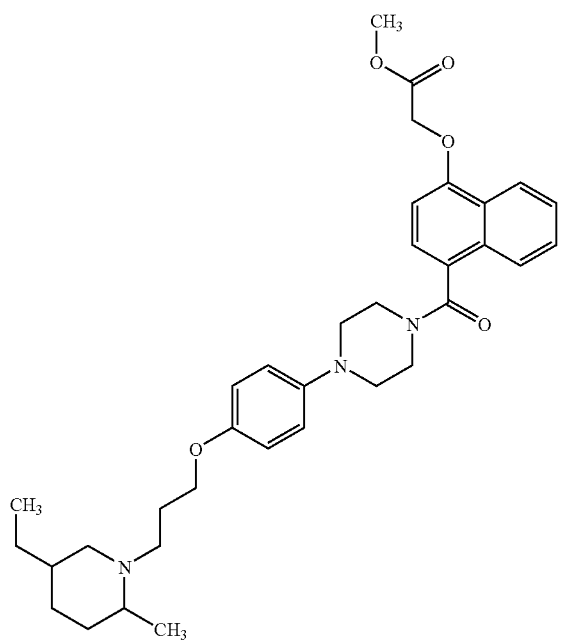 | 2.39 | 444 |
| 87 | 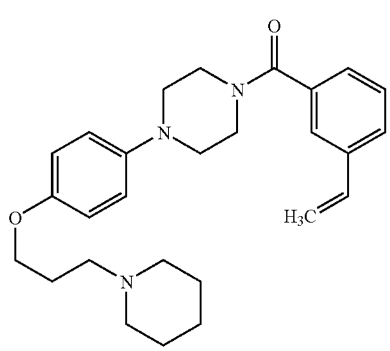 | 2.50 | 434 |

-continued

| Example | Structure | RT (min) | Mass Ion (M + H)+ |
|---|---|---|---|
| 88 | 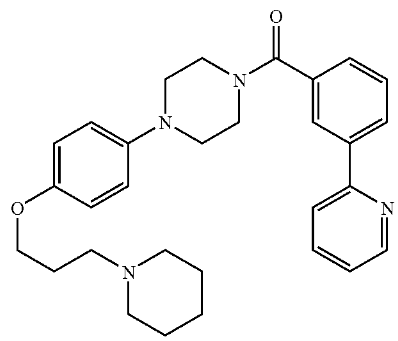 | 2.36 | 485 |
| 89 | 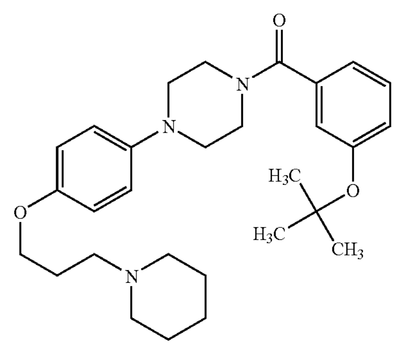 | 2.58 | 480 |
| 90 | 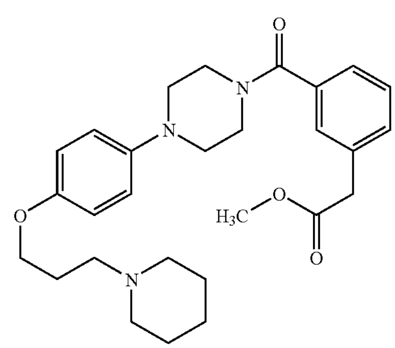 | 2.34 | 480 |
| 91 | 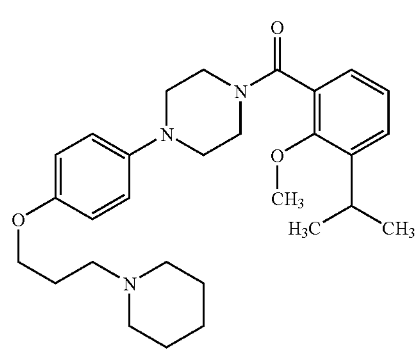 | 2.66 | 480 |

-continued

| Example | Structure | RT (min) | Mass Ion (M + H)+ |
|---|---|---|---|
| 92 | (structure) | 2.23 | 456 |
| 93 | (structure) | 2.76 | 464 |
| 94 | (structure) | 2.24 | 424 |
| 95 | (structure) | 2.16 | 468 |

-continued

| Example | Structure | RT (min) | Mass Ion (M + H)+ |
|---------|-----------|----------|-------------------|
| 96 | 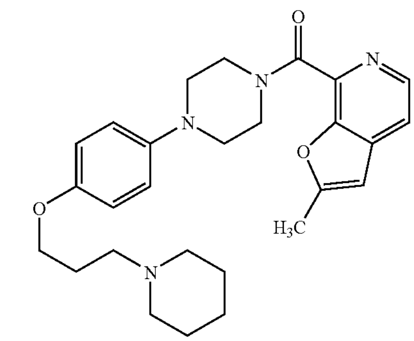 | 1.87 | 463 |
| 97 | 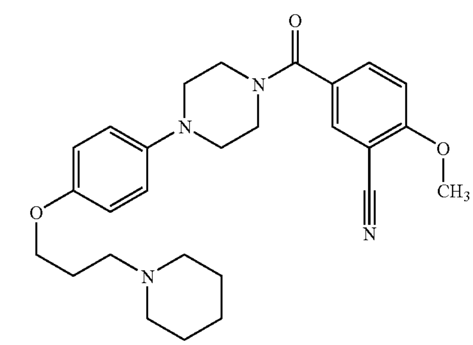 | 1.96 | 463 |
| 98 | 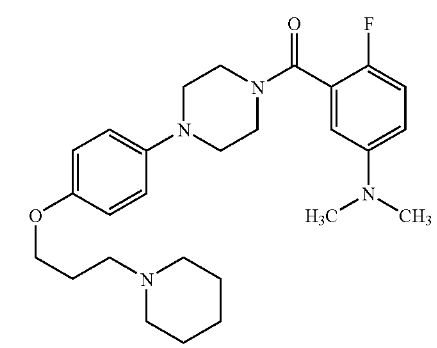 | 1.85 | 467 |
| 99 | 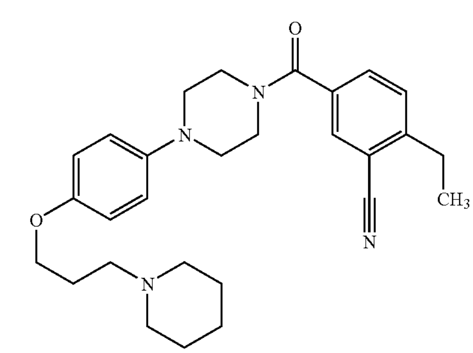 | 2.11 | 461 |

-continued
| Example | Structure | RT (min) | Mass Ion (M + H)+ |
|---|---|---|---|
| 100 | 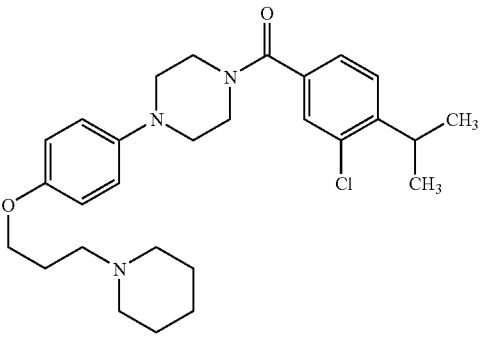 | 2.37 | 484 |
| 101 | 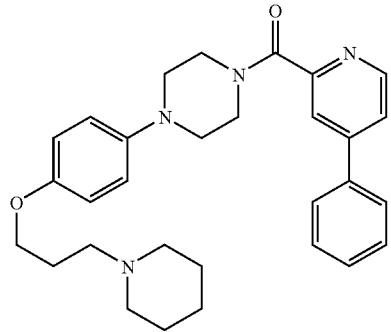 | 2.11 | 485 |
| 102 | 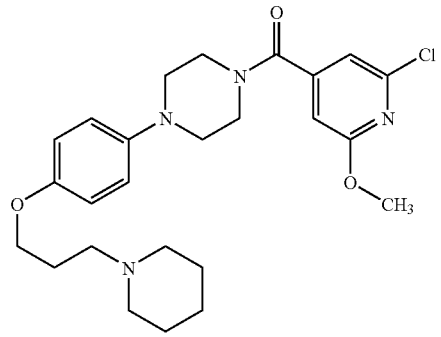 | 2.05 | 473<br>475 |
| 103 | 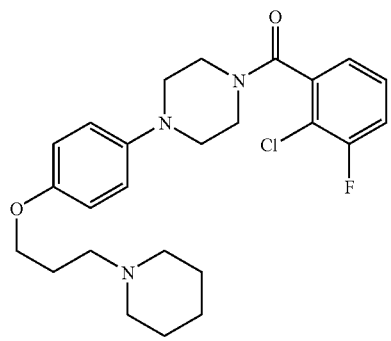 | 2.07 | 460<br>462 |

-continued

| Example | Structure | RT (min) | Mass Ion (M + H)+ |
|---|---|---|---|
| 104 | 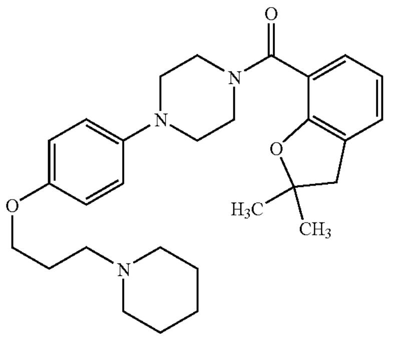 | 2.07 | 478 |
| 105 | 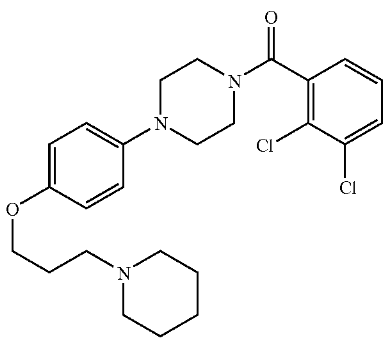 | 2.18 | 476 478 |
| 106 | 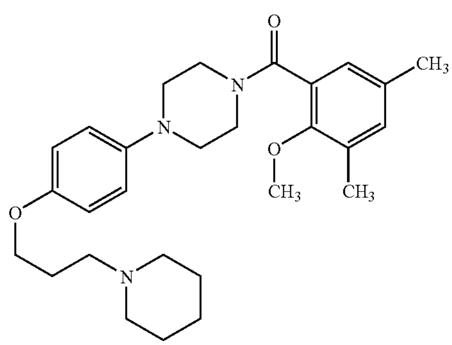 | 2.13 | 466 |
| 107 | 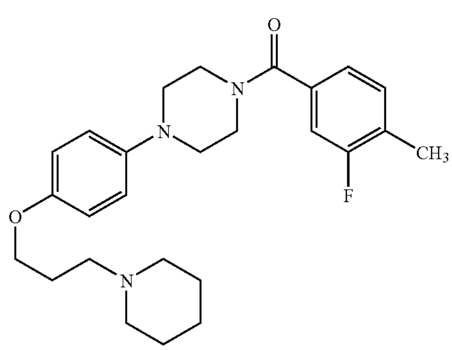 | 2.05 | 440 |

-continued

| Example | Structure | RT (min) | Mass Ion $(M+H)^+$ |
|---|---|---|---|
| 108 | 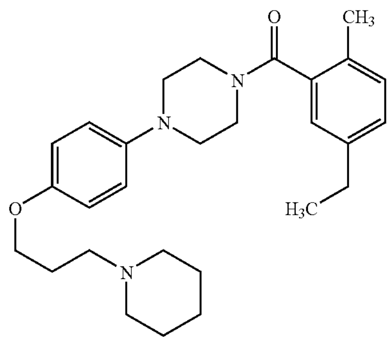 | 2.20 | 450 |
| 109 | 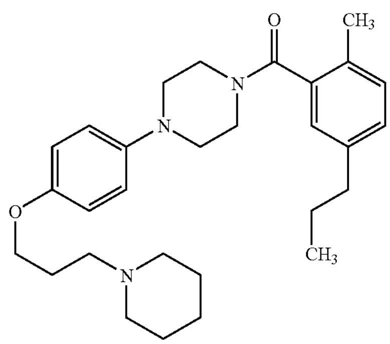 | 2.31 | 464 |
| 110 | 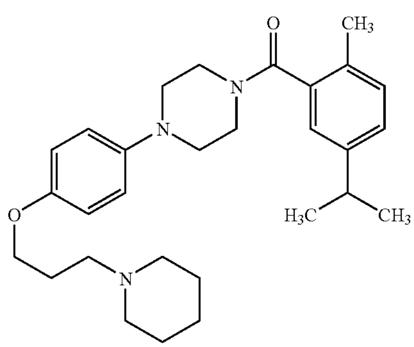 | 2.31 | 464 |
| 111 | 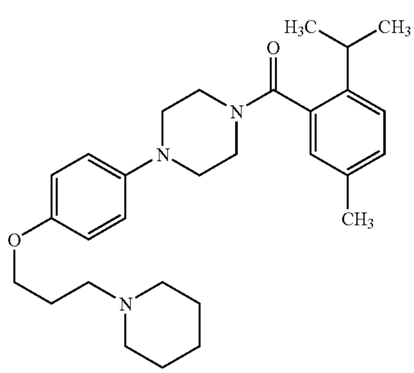 | 2.29 | 464 |

| Example | Structure | RT (min) | Mass Ion (M + H)+ |
|---|---|---|---|
| 112 | 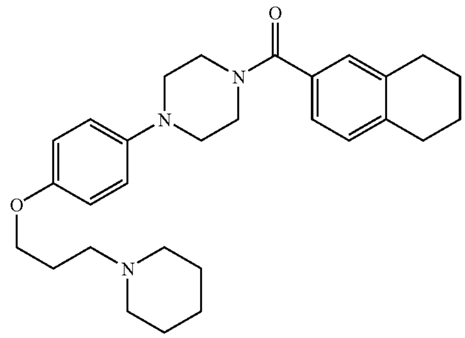 | 2.22 | 462 |
| 113 | 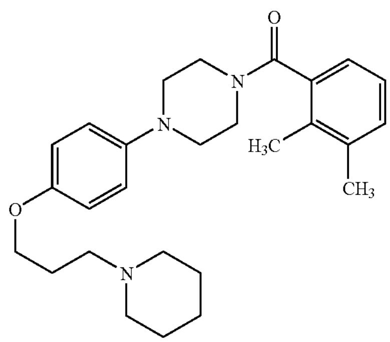 | 2.07 | 436 |
| 114 | 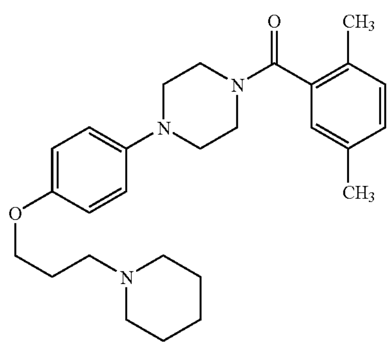 | 2.07 | 436 |
| 115 | 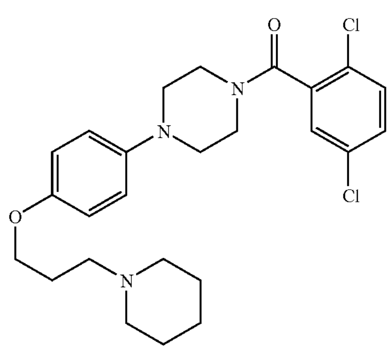 | 2.12 | 476, 478 |

-continued

| Example | Structure | RT (min) | Mass Ion (M + H)+ |
|---|---|---|---|
| 116 | 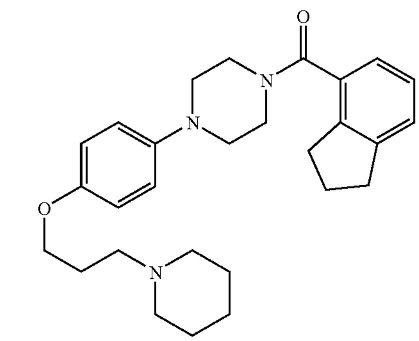 | 2.13 | 448 |
| 117 | 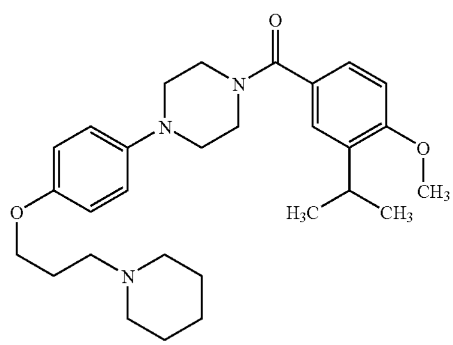 | 2.26 | 480 |
| 118 | 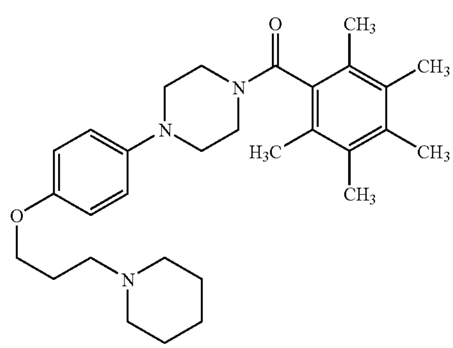 | 2.29 | 478 |
| 119 | 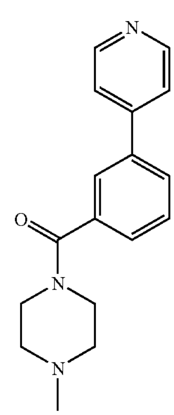 | 2.15 | 485 |

-continued

| Example | Structure | RT (min) | Mass Ion (M + H)+ |
|---------|-----------|----------|-------------------|
| 120 | 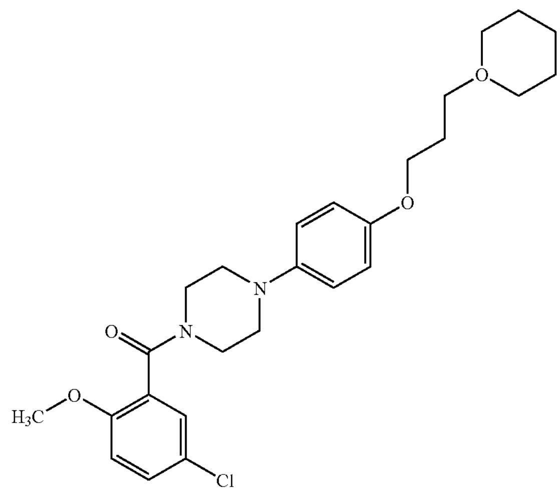 | 2.52 | 472 |
| 121 | 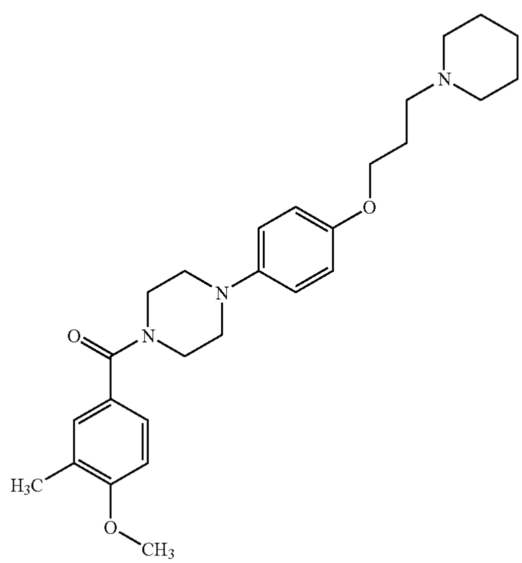 | 2.52 | 452 |

-continued

| Example | Structure | RT (min) | Mass Ion (M + H)+ |
|---|---|---|---|
| 122 | 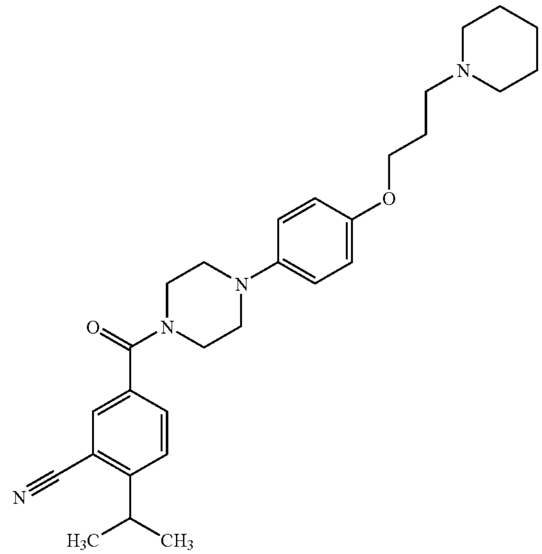 | 2.63 | 475 |
| 123 | 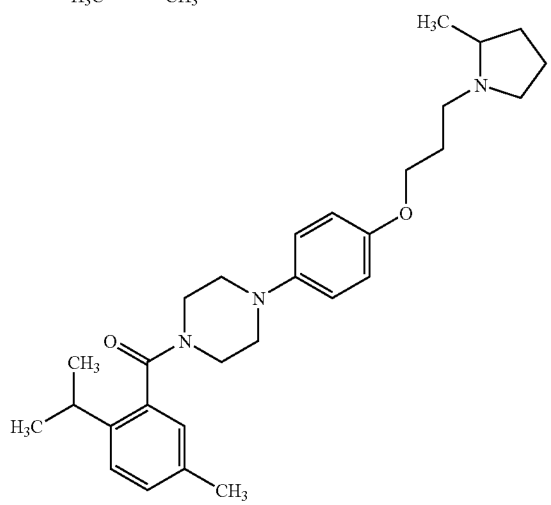 | 2.53 | 464 |
| 124 | 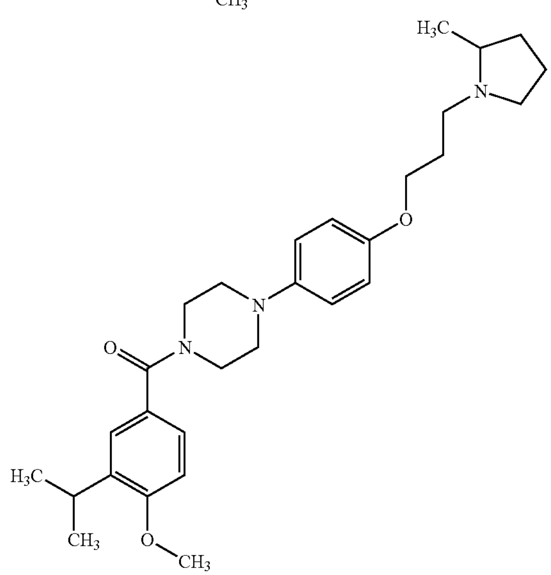 | 2.53 | 480 |

| Example | Structure | RT (min) | Mass Ion (M + H)+ |
|---|---|---|---|
| 125 | 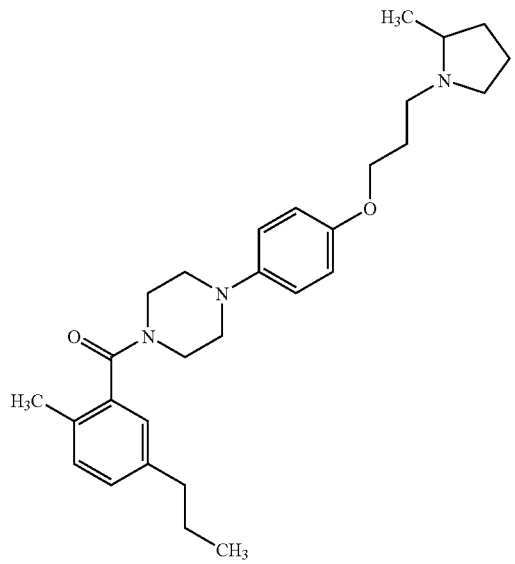 | 2.60 | 464 |
| 126 | 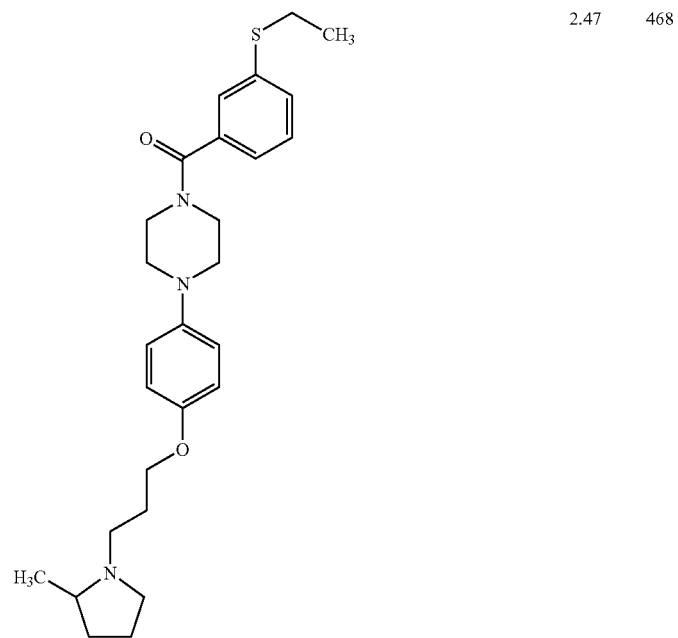 | 2.47 | 468 |

| Example | Structure | RT (min) | Mass Ion (M + H)+ |
|---------|-----------|----------|-------------------|
| 127 | 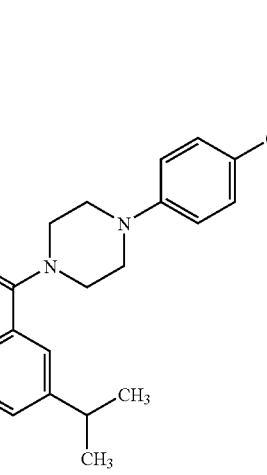 | 2.59 | 464 |
| 128 | 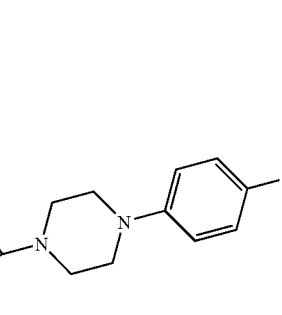 | 2.61 | 537 |
| 129 | 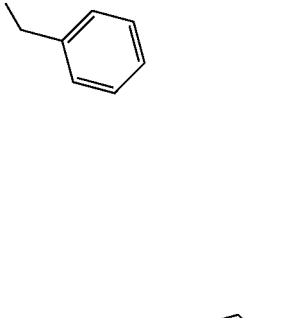 | 2.37 | 475 |

-continued

| Example | Structure | RT (min) | Mass Ion (M + H)+ |
|---|---|---|---|
| 130 | 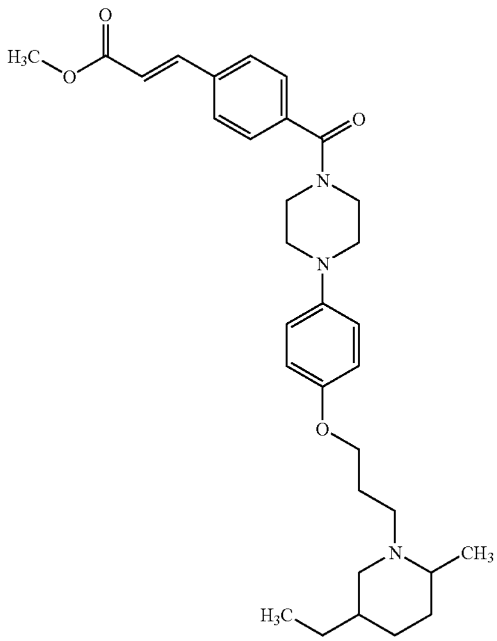 | 2.58 | 534 |
| 131 | 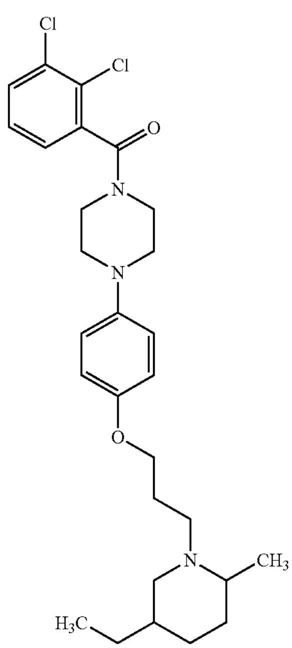 | 2.66 | 518<br>520 |

-continued

| Example | Structure | RT (min) | Mass Ion (M + H)+ |
|---|---|---|---|
| 132 | 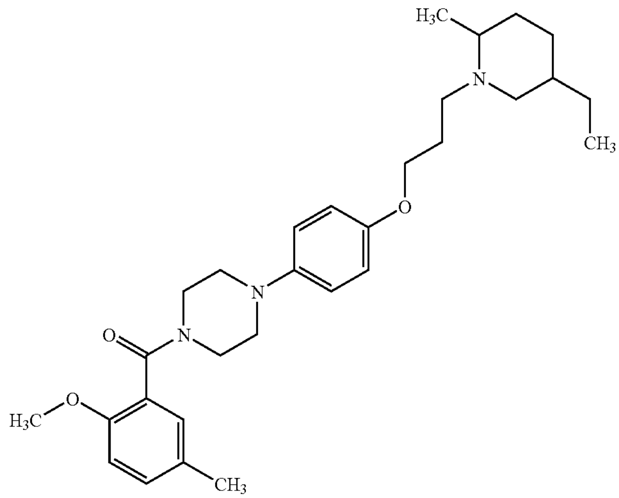 | 2.54 | 494 |
| 133 | 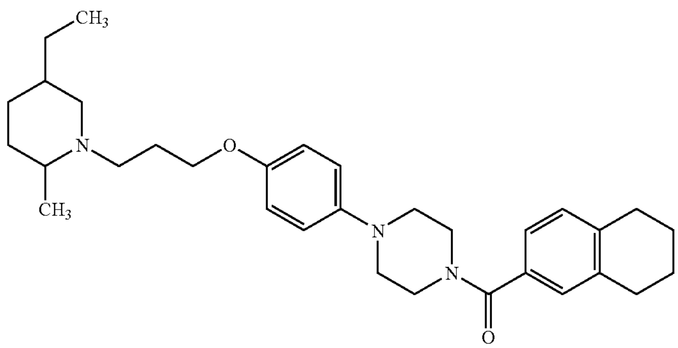 | 2.76 | 504 |
| 134 | 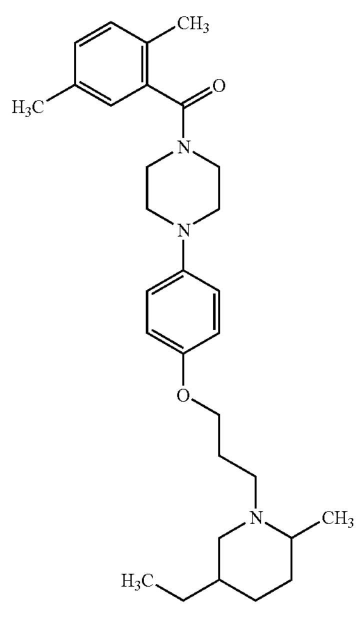 | 2.60 | 478 |

| Example | Structure | RT (min) | Mass Ion (M + H)+ |
|---|---|---|---|
| 135 | 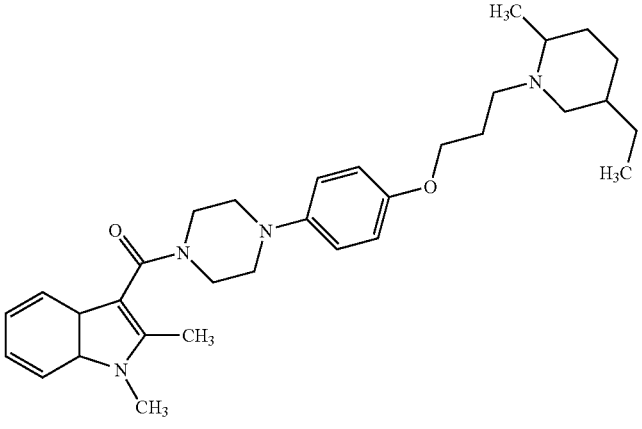 | 2.60 | 517 |
| 136 | 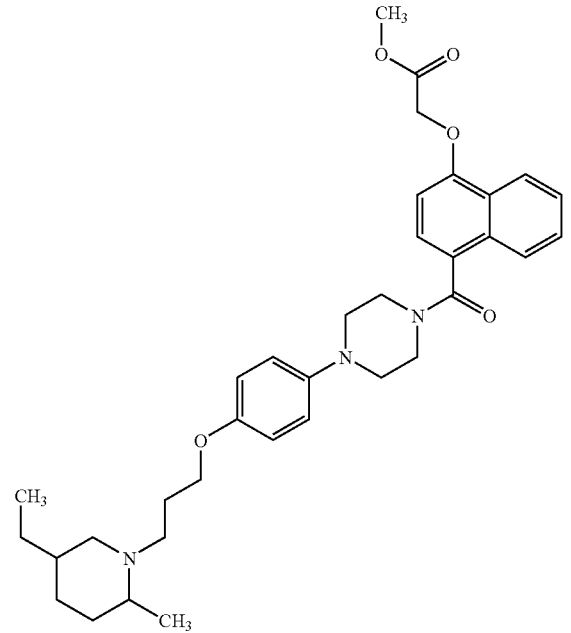 | 2.65 | 588 |
| 137 | 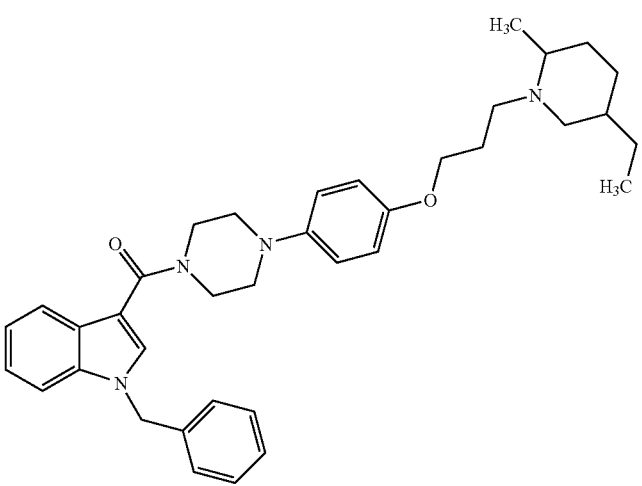 | 2.83 | 579 |

-continued
| Example | Structure | RT (min) | Mass Ion (M + H)+ |
|---|---|---|---|
| 138 | 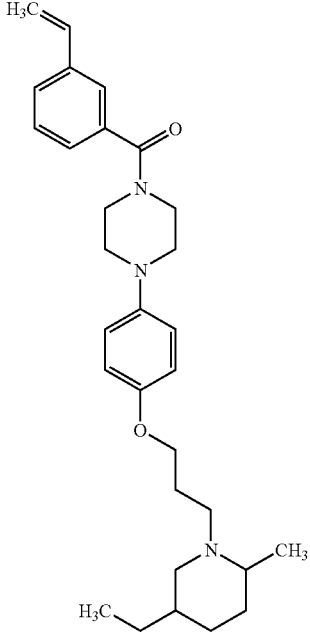 | 2.60 | 476 |
| 139 | 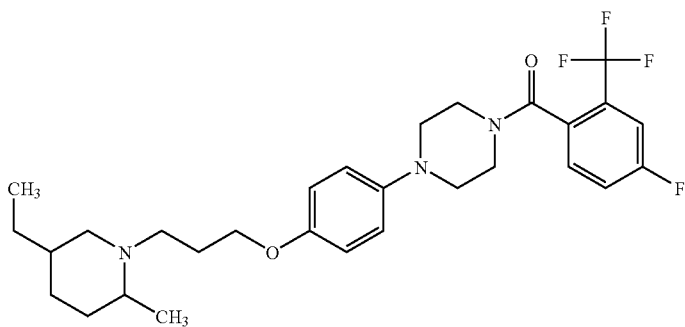 | 2.63 | 536 |
| 140 | 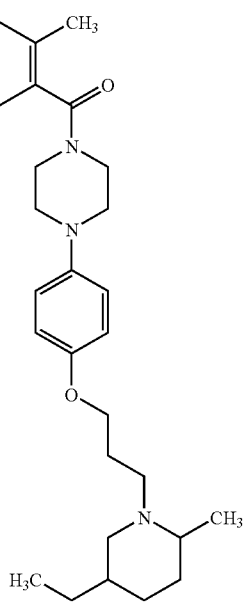 | 2.69 | 542 |

-continued

| Example | Structure | RT (min) | Mass Ion (M + H)+ |
|---------|-----------|----------|-------------------|
| 141 | 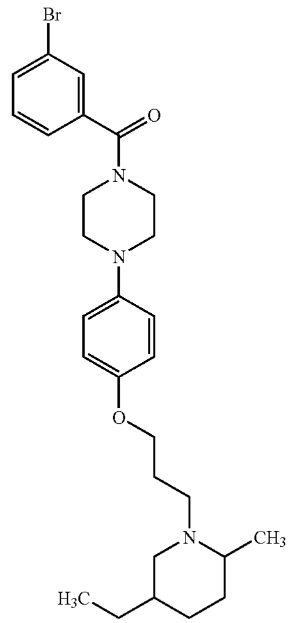 | 2.62 | 528<br>530 |
| 142 | 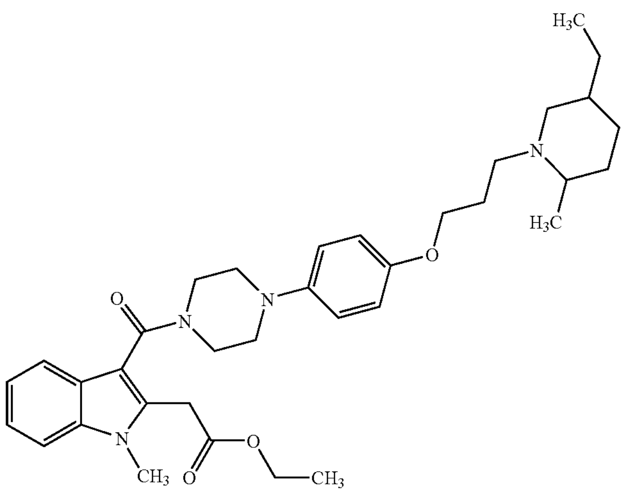 | 2.68 | 589 |
| 143 | 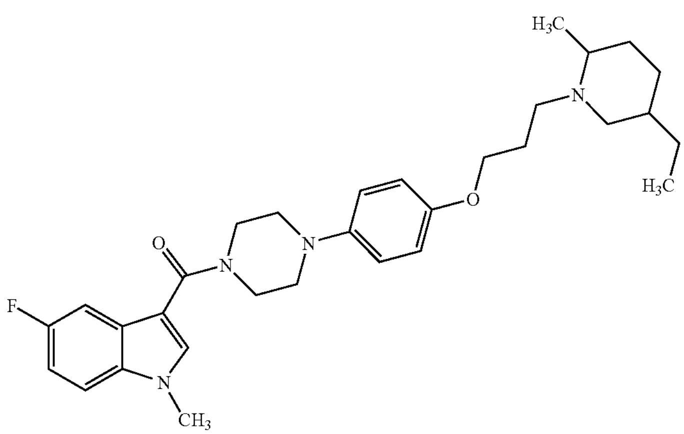 | 2.61 | 521 |

| Example | Structure | RT (min) | Mass Ion (M + H)+ |
|---|---|---|---|
| 144 | 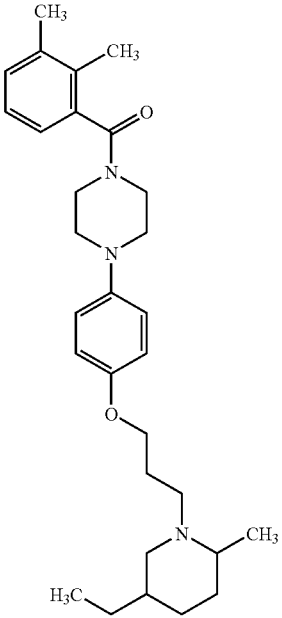 | 2.58 | 478 |
| 145 | 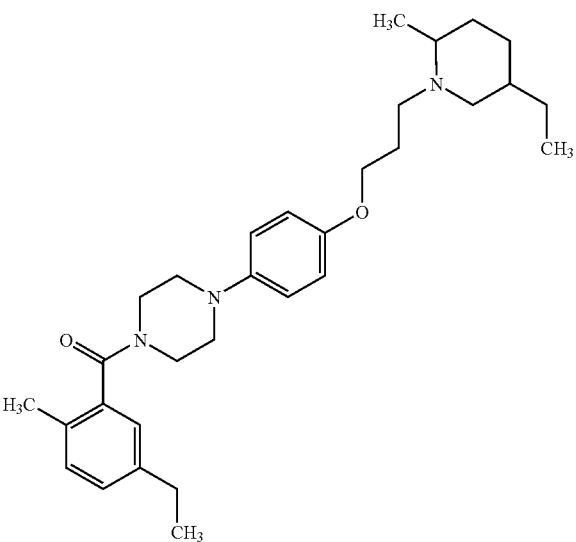 | 2.70 | 492 |

-continued

| Example | Structure | RT (min) | Mass Ion (M + H)+ |
|---------|-----------|----------|-------------------|
| 146 | 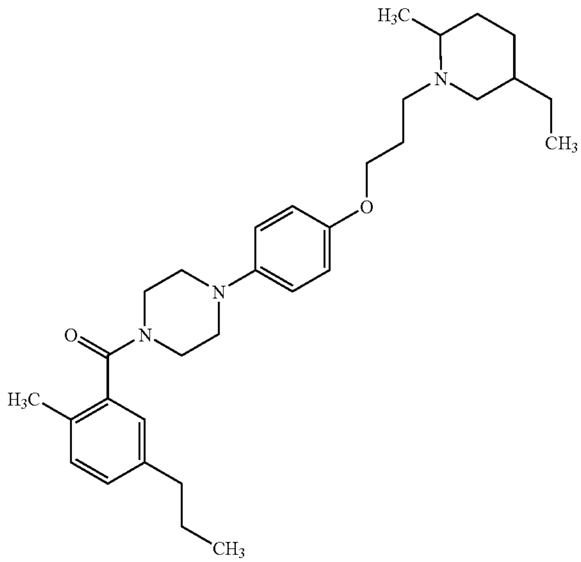 | 2.81 | 506 |
| 147 | 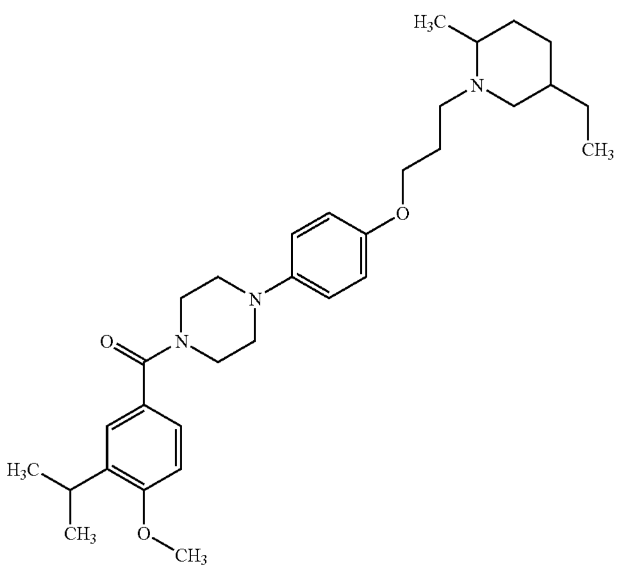 | 2.77 | 522 |

-continued

| Example | Structure | RT (min) | Mass Ion (M + H)+ |
|---------|-----------|----------|-------------------|
| 148 | 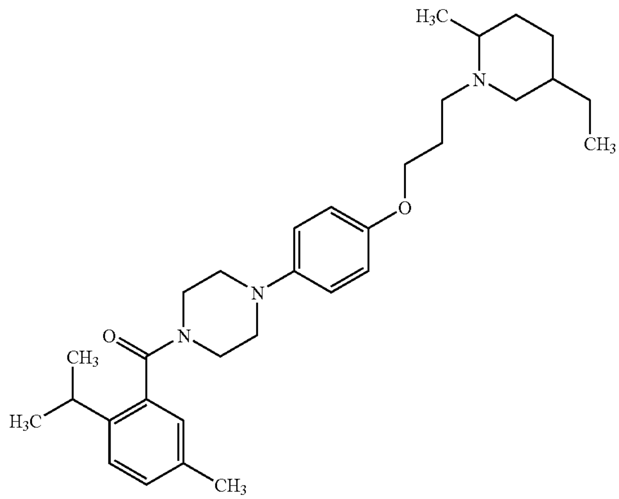 | 2.77 | 506 |
| 149 | 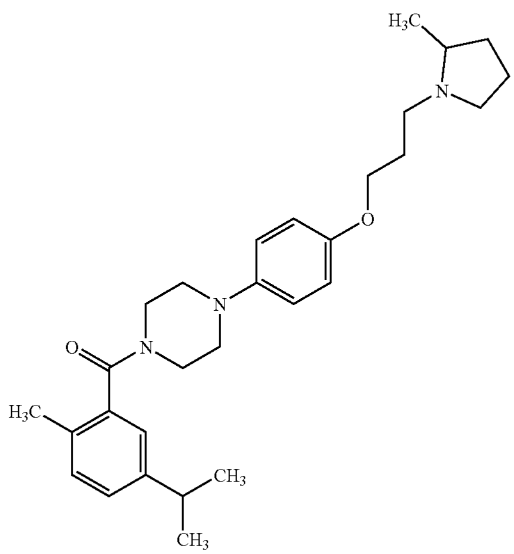 | 2.59 | 464 |
| 150 | 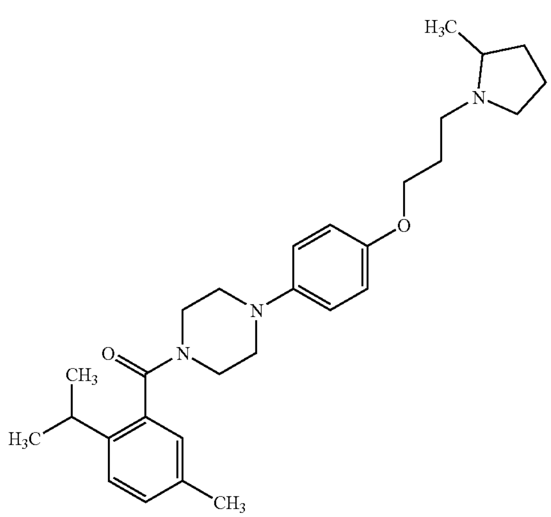 | 2.57 | 464 |

| Example | Structure | RT (min) | Mass Ion (M + H)+ |
|---------|-----------|----------|-------------------|
| 151 | 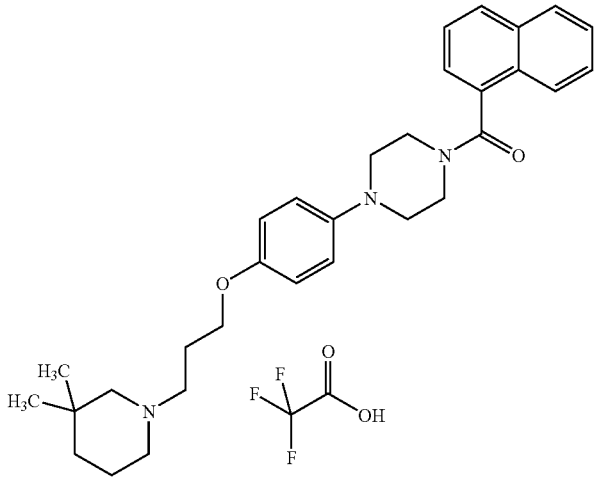 | 2.27 | 486 |
| 152 | 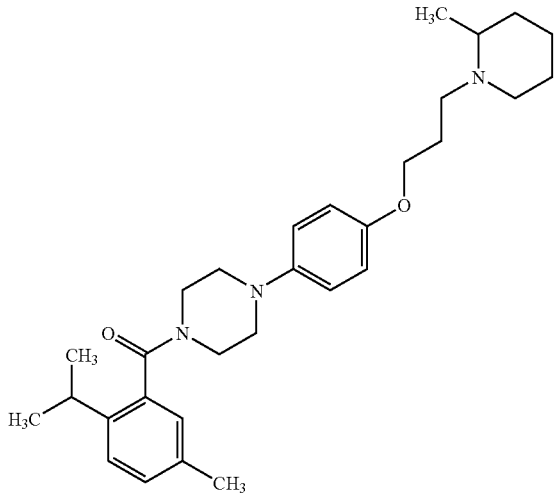 | 2.60 | 478 |
| 153 | 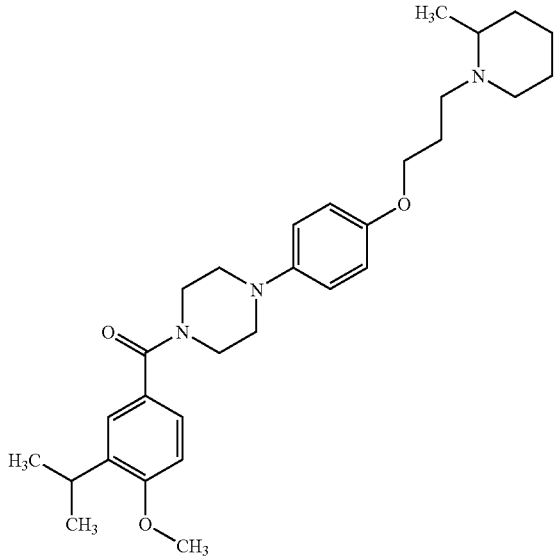 | 2.63 | 494 |

-continued

| Example | Structure | RT (min) | Mass Ion (M + H)+ |
|---------|-----------|----------|-------------------|
| 154 | 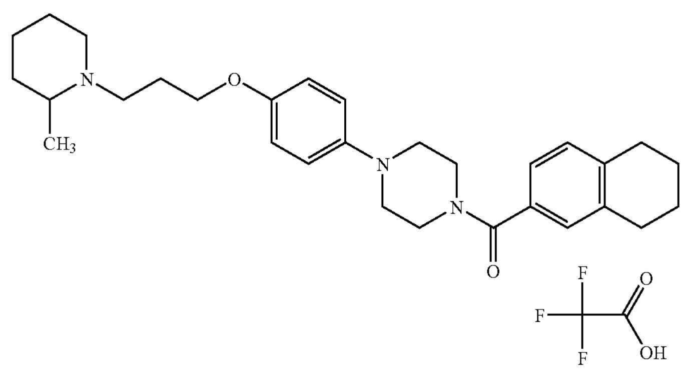 | 2.36 | 466 |
| 155 | 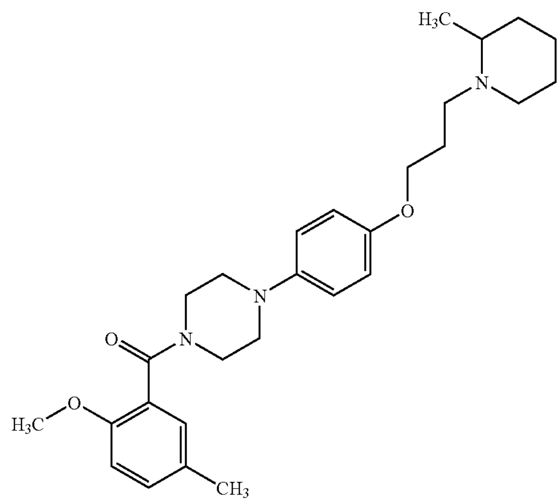 | 2.36 | 466 |
| 156 | 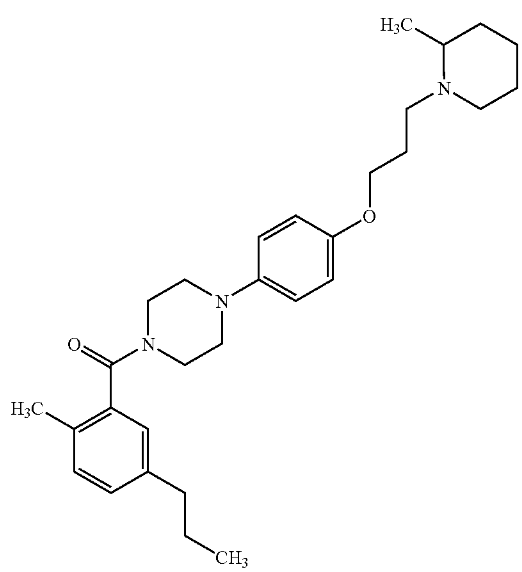 | 2.65 | 478 |

-continued

| Example | Structure | RT (min) | Mass Ion (M + H)+ |
|---------|-----------|----------|-------------------|
| 157 | 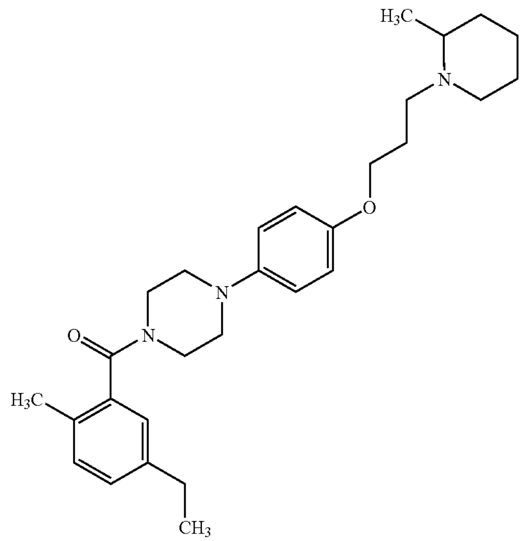 | 2.54 | 464 |
| 158 | 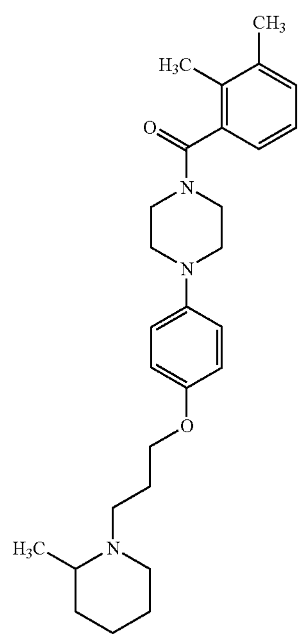 | 2.40 | 450 |

-continued
| Example | Structure | RT (min) | Mass Ion (M + H)+ |
|---------|-----------|----------|-------------------|
| 159 | 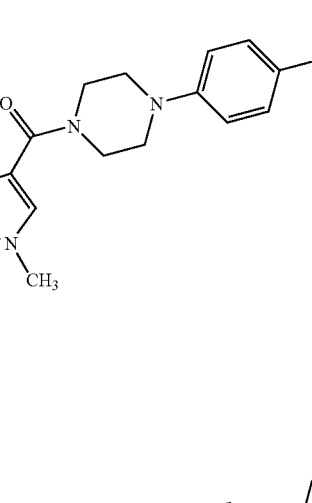 | 2.42 | 561 |
| 160 | 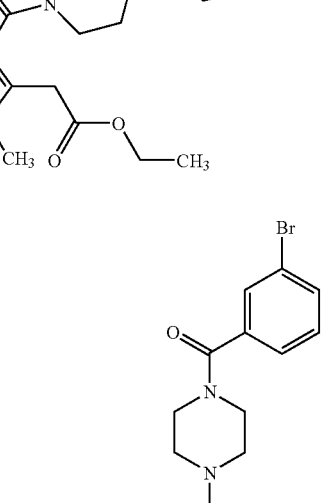 | 2.42 | 561 |
| 161 | 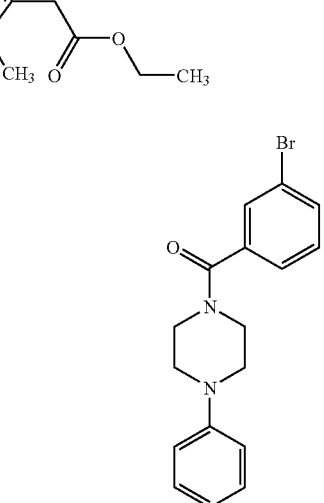 | 2.51 | 500<br>502 |

-continued
| Example | Structure | RT (min) | Mass Ion (M + H)+ |
|---|---|---|---|
| 162 | 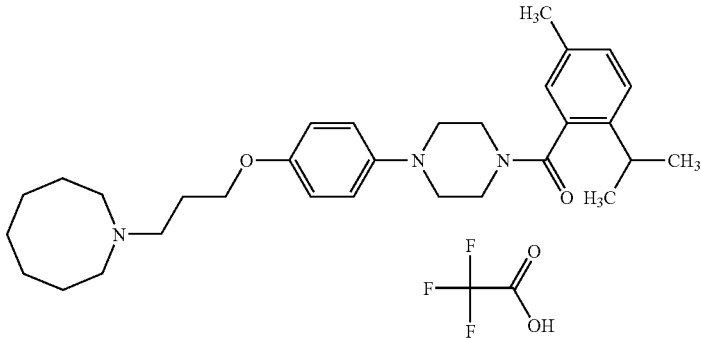 | 2.66 | 492 |
| 163 | 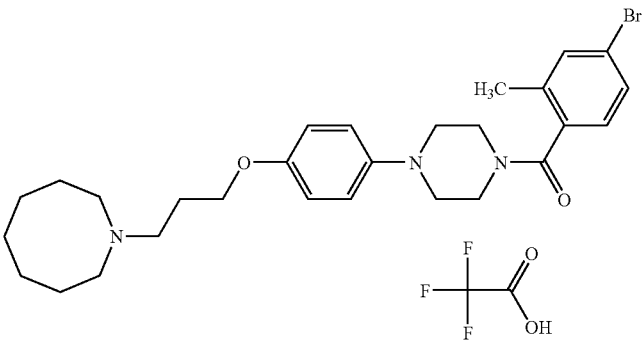 | 2.60 | 528 530 |
| 164 | 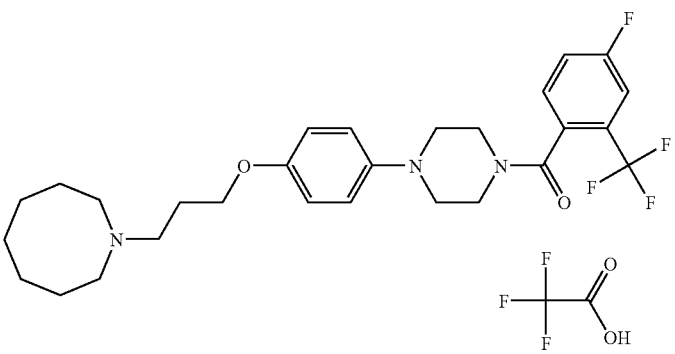 | 2.54 | 522 |
| 165 | 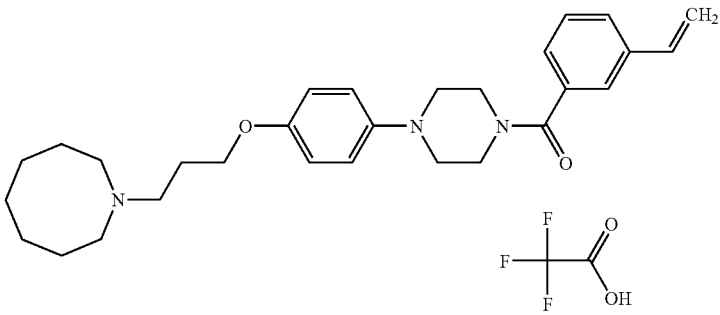 | 2.51 | 462 |

| Example | Structure | RT (min) | Mass Ion (M + H)+ |
| --- | --- | --- | --- |
| 166 | 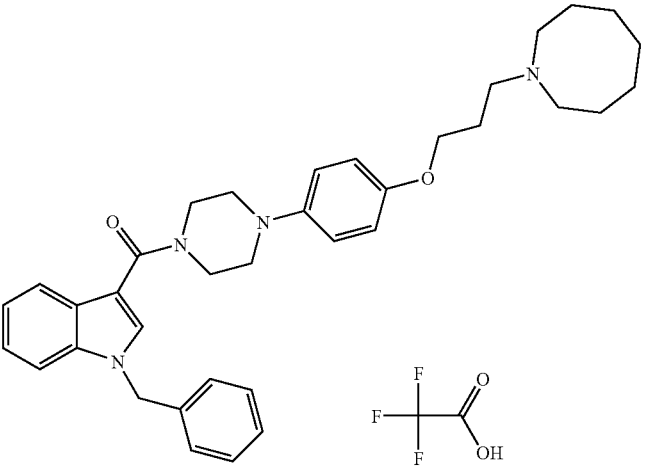 | 2.76 | 565 |
| 167 | 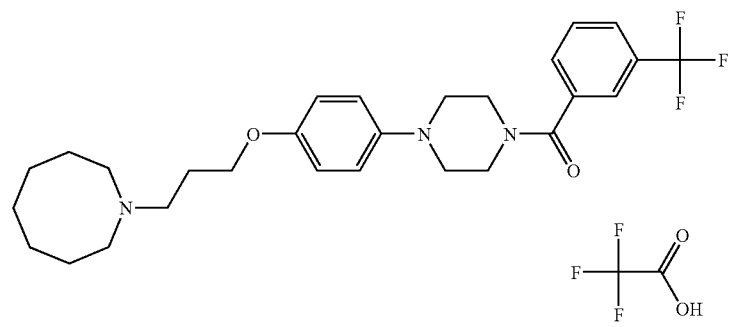 | 2.55 | 504 |
| 168 | 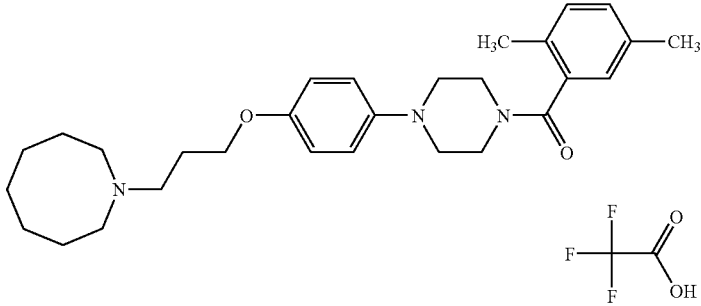 | 2.51 | 464 |
| 169 | 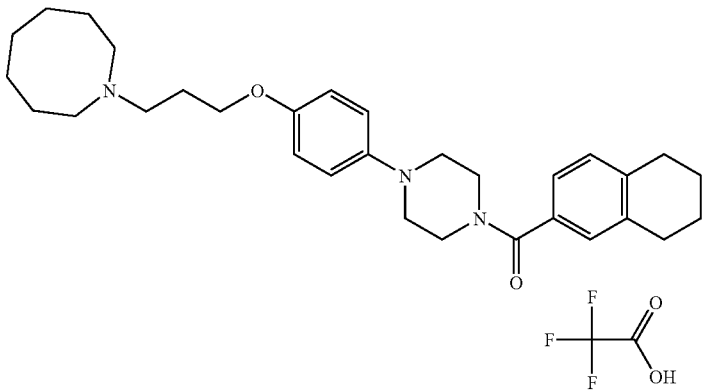 | 2.67 | 490 |

| Example | Structure | RT (min) | Mass Ion (M + H)+ |
|---|---|---|---|
| 170 | 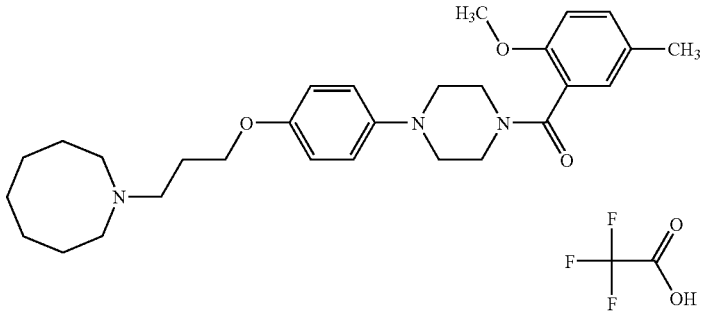 | 2.45 | 480 |
| 171 | 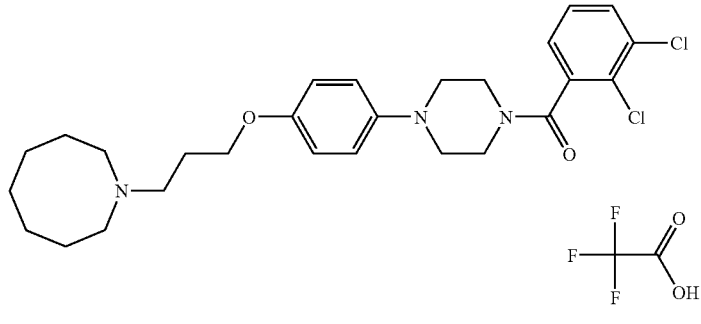 | 2.57 | 504 506 |
| 172 | 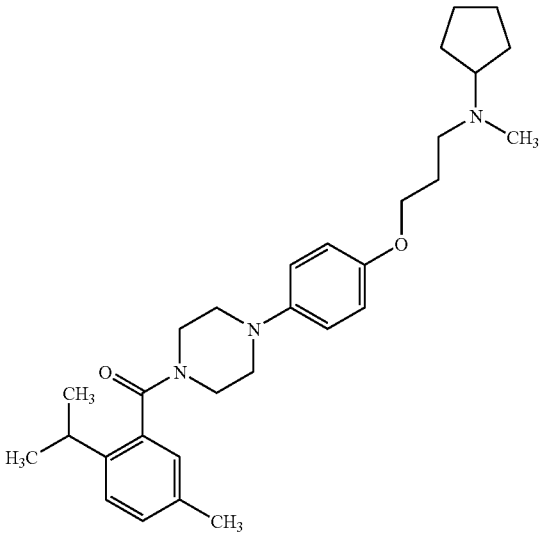 | 2.63 | 478 |

-continued

| Example | Structure | RT (min) | Mass Ion (M + H)+ |
|---------|-----------|----------|-------------------|
| 173 | 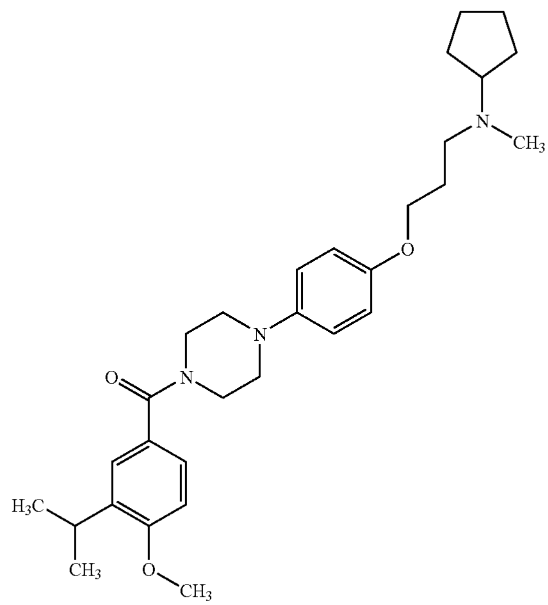 | 2.65 | 494 |
| 174 | 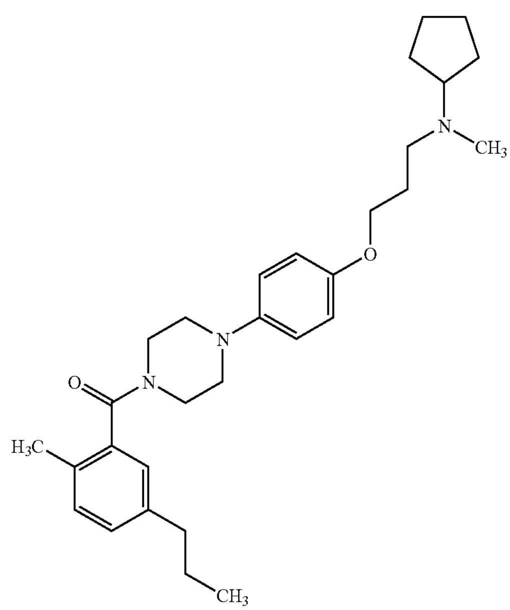 | 2.69 | 478 |

-continued
| Example | Structure | RT (min) | Mass Ion (M + H)+ |
|---|---|---|---|
| 175 | 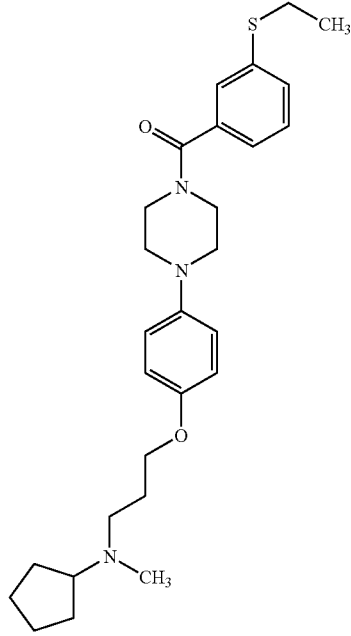 | 2.56 | 482 |
| 176 | 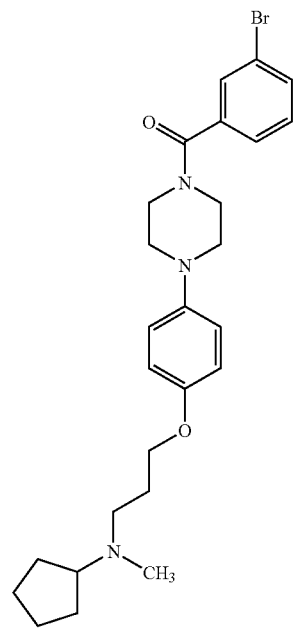 | 2.49 | 500<br>502 |

| Example | Structure | RT (min) | Mass Ion (M + H)+ |
|---|---|---|---|
| 177 | 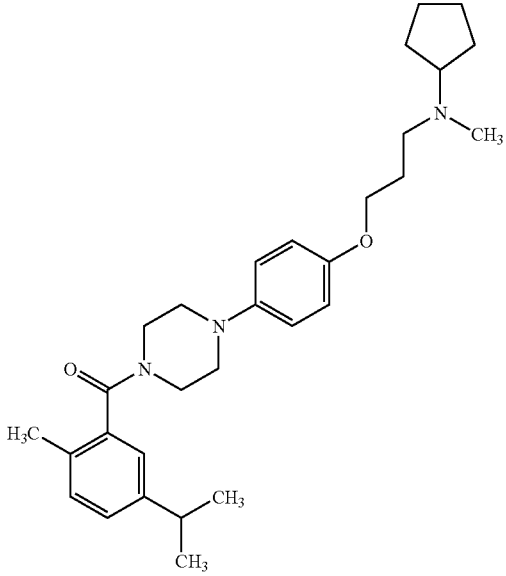 | 2.66 | 478 |
| 178 | 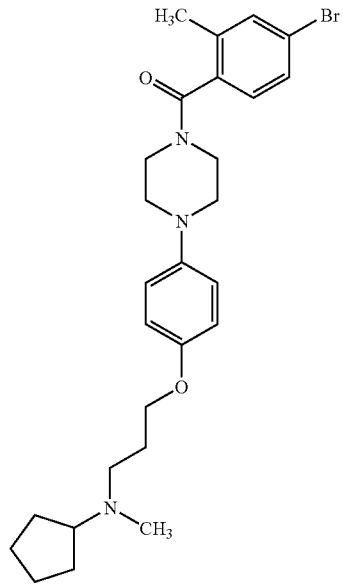 | 2.55 | 514<br>516 |

-continued
| Example | Structure | RT (min) | Mass Ion (M + H)+ |
|---------|-----------|----------|-------------------|
| 179 | 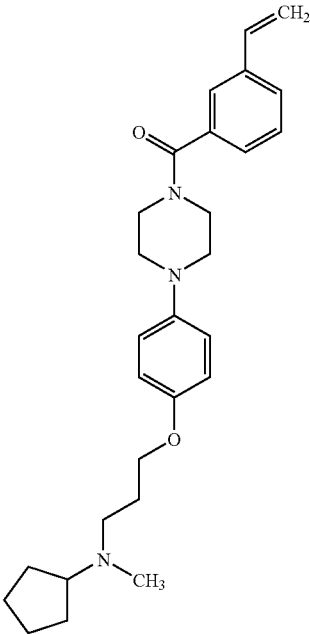 | 2.47 | 448 |
| 180 | 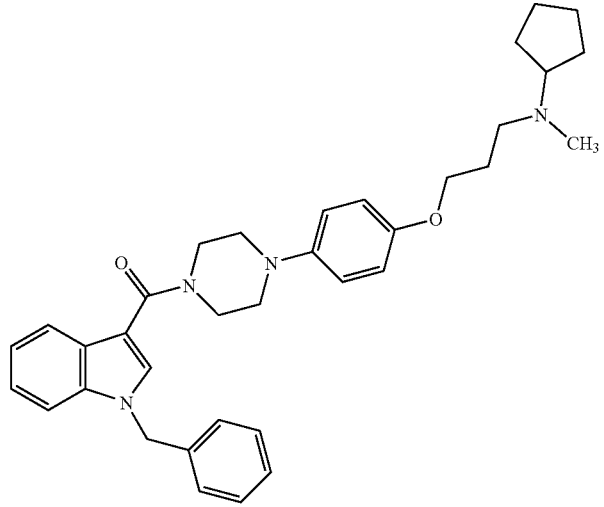 | 2.72 | 551 |

| Example | Structure | RT (min) | Mass Ion (M + H)+ |
|---------|-----------|----------|-------------------|
| 181 | 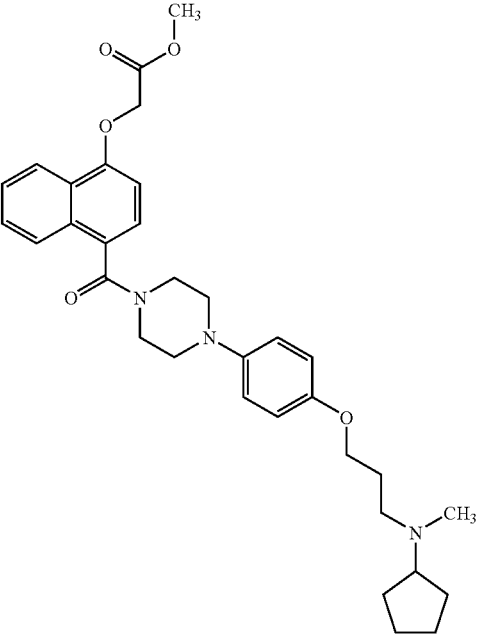 | 2.52 | 560 |
| 182 | 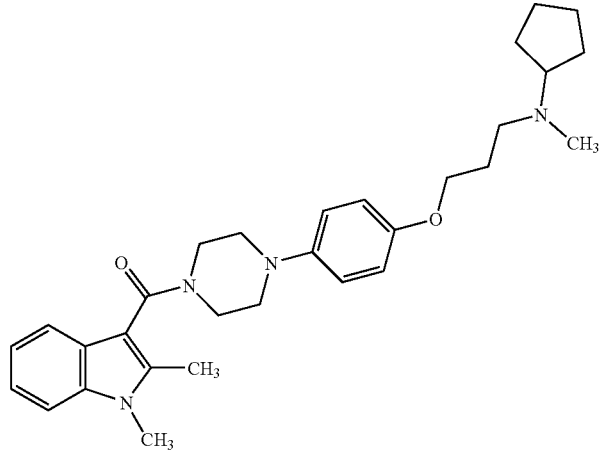 | 2.47 | 489 |

-continued

| Example | Structure | RT (min) | Mass Ion (M + H)+ |
|---|---|---|---|
| 183 | 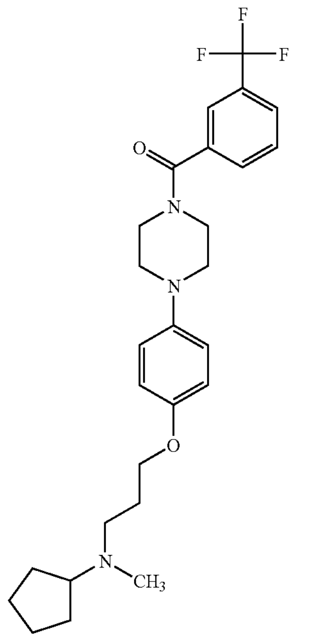 | 2.54 | 490 |
| 184 | 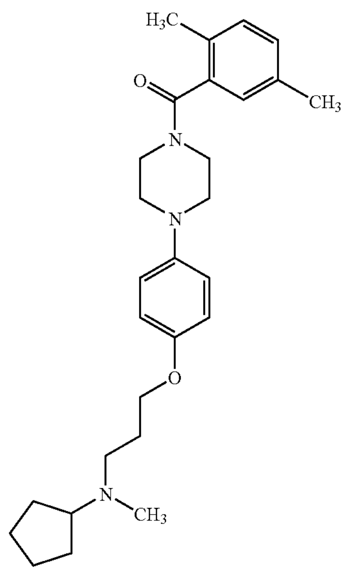 | 2.47 | 450 |
| 185 | 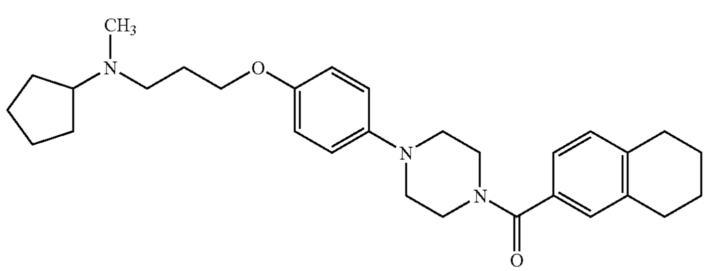 | 2.60 | 476 |

-continued
| Example | Structure | RT (min) | Mass Ion (M + H)+ |
|---|---|---|---|
| 186 | 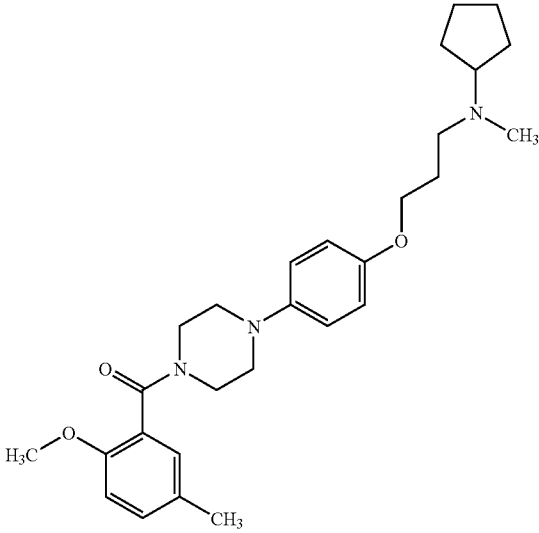 | 2.39 | 466 |
| 187 | 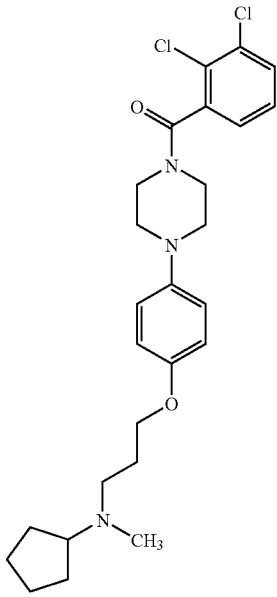 | 2.53 | 491 |

-continued
| Example | Structure | RT (min) | Mass Ion (M + H)+ |
|---|---|---|---|
| 188 | 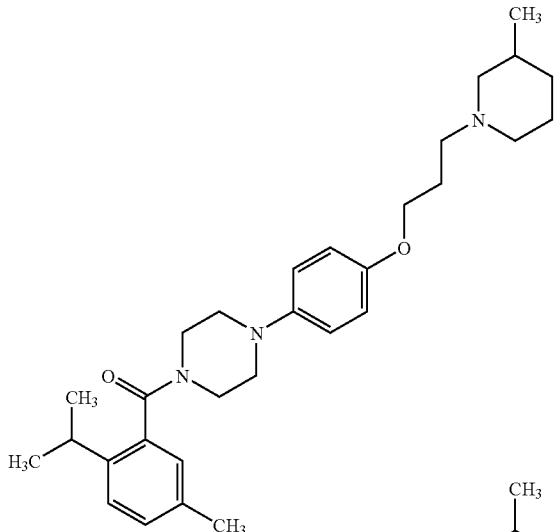 | 2.63 | 478 |
| 189 | 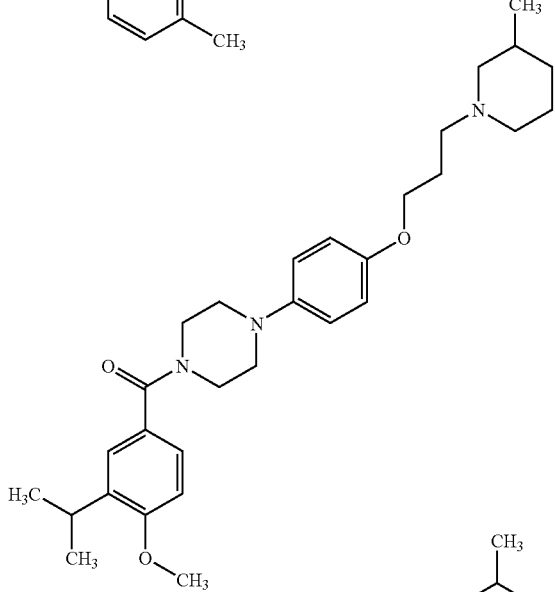 | 2.64 | 494 |
| 190 | 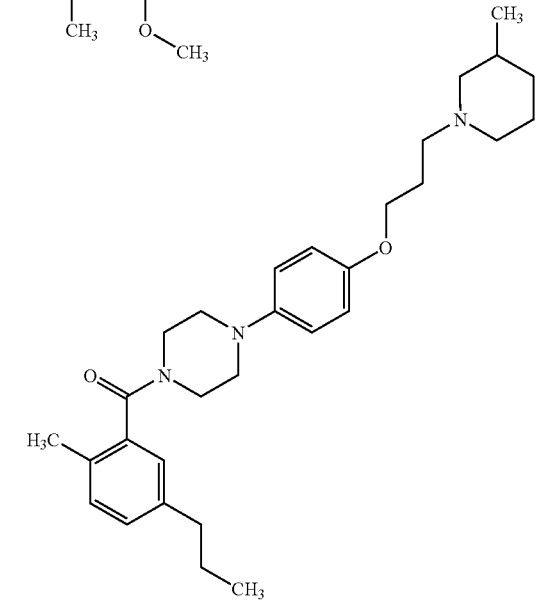 | 2.68 | 478 |

| Example | Structure | RT (min) | Mass Ion (M + H)+ |
|---|---|---|---|
| 191 | 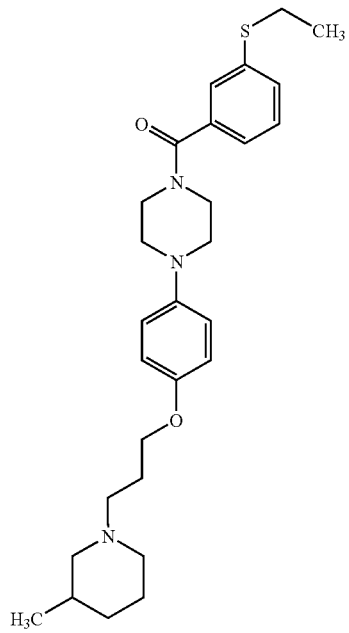 | 2.58 | 482 |
| 192 | 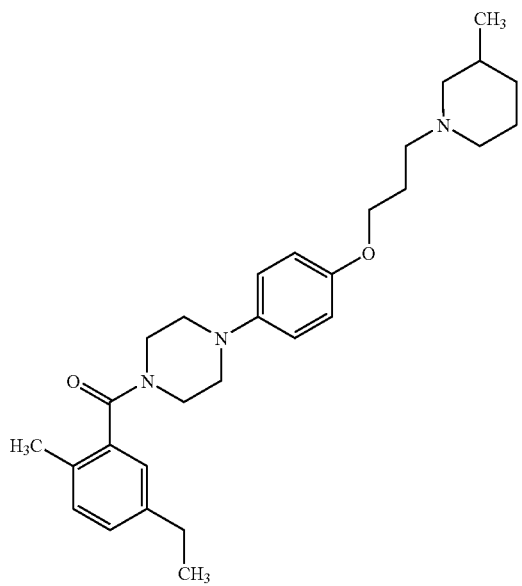 | 2.55 | 464 |

| Example | Structure | RT (min) | Mass Ion (M + H)+ |
|---|---|---|---|
| 193 | 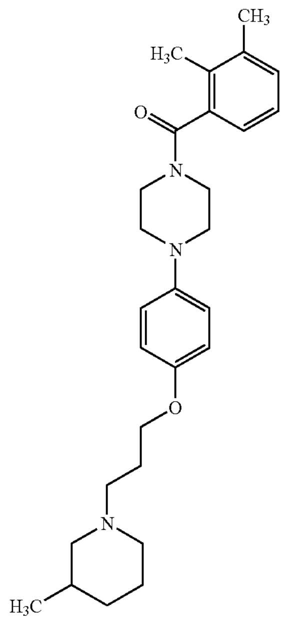 | 2.44 | 450 |
| 194 | 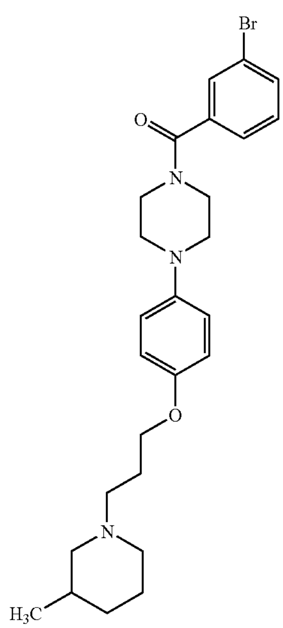 | 2.47 | 500 502 |

-continued

| Example | Structure | RT (min) | Mass Ion (M + H)+ |
|---|---|---|---|
| 195 | 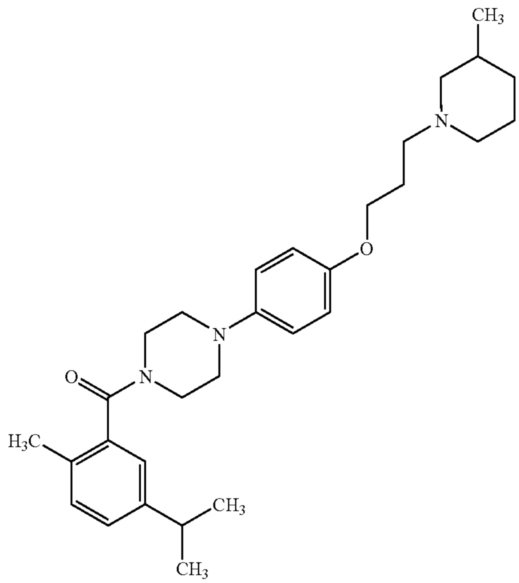 | 2.66 | 478 |
| 196 | 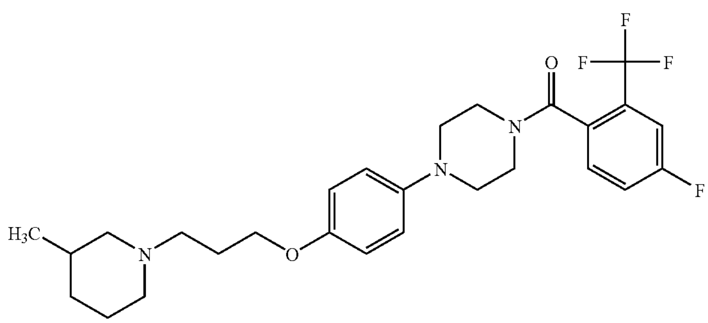 | 2.44 | 508 |
| 197 | 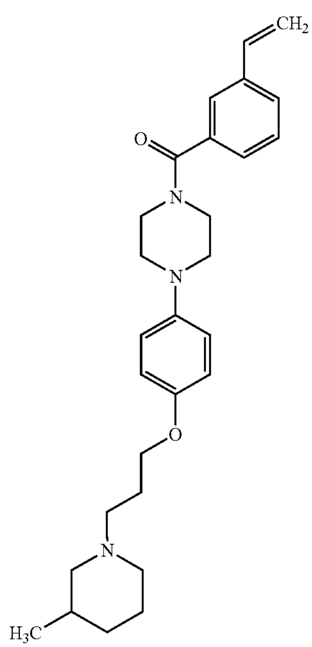 | 2.44 | 448 |

-continued
| Example | Structure | RT (min) | Mass Ion (M + H)+ |
|---|---|---|---|
| 198 | 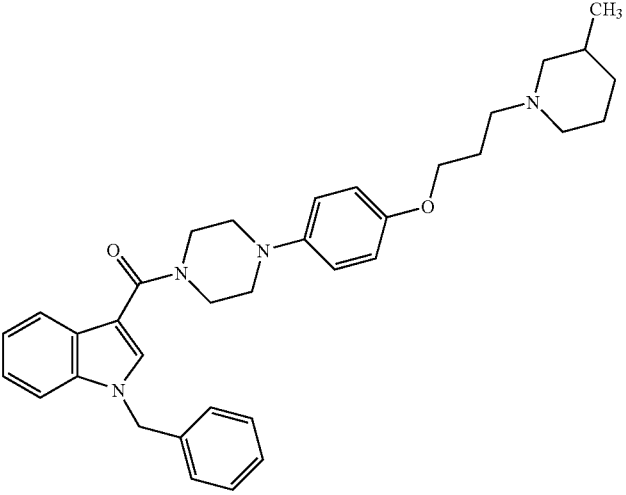 | 2.71 | 551 |
| 199 | 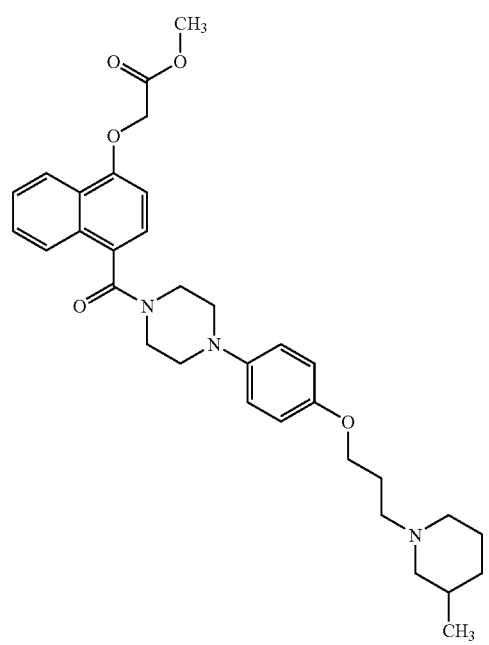 | 2.52 | 560 |
| 200 | 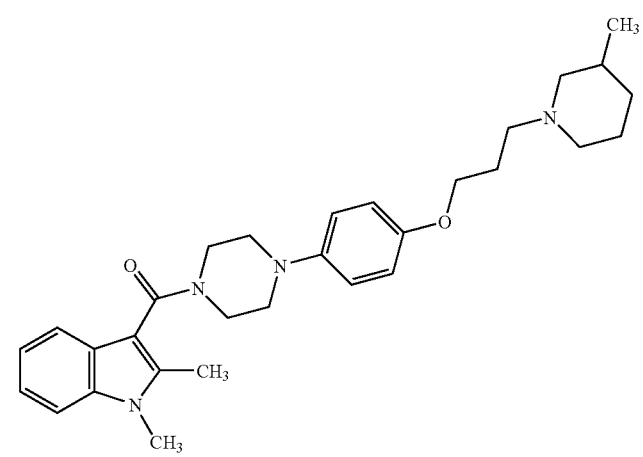 | 2.46 | 489 |

-continued

| Example | Structure | RT (min) | Mass Ion (M + H)+ |
|---|---|---|---|
| 201 | 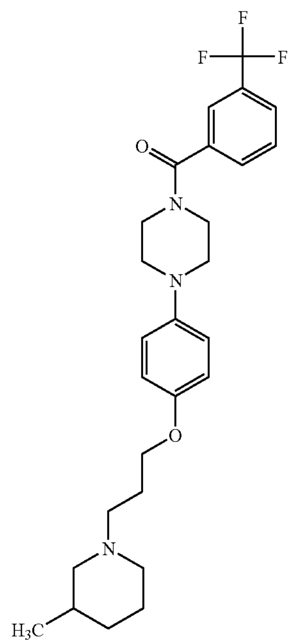 | 2.50 | 490 |
| 202 | 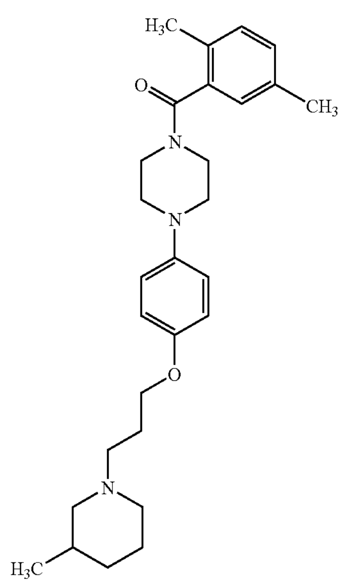 | 2.46 | 450 |
| 203 | 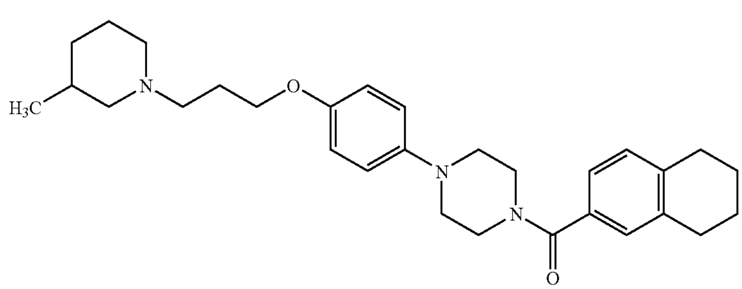 | 2.62 | 476 |

| Example | Structure | RT (min) | Mass Ion (M + H)+ |
|---|---|---|---|
| 204 | 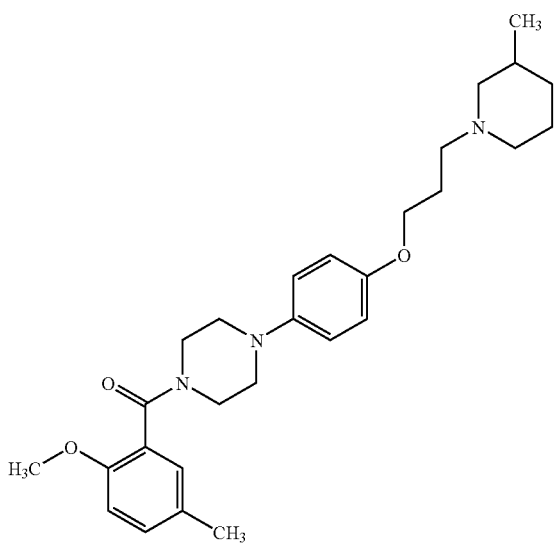 | 2.39 | 466 |
| 205 | 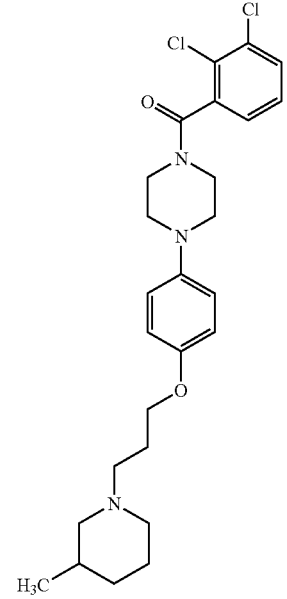 | 2.52 | 490<br>492 |

| Example | Structure | RT (min) | Mass Ion (M + H)+ |
|---|---|---|---|
| 206 | 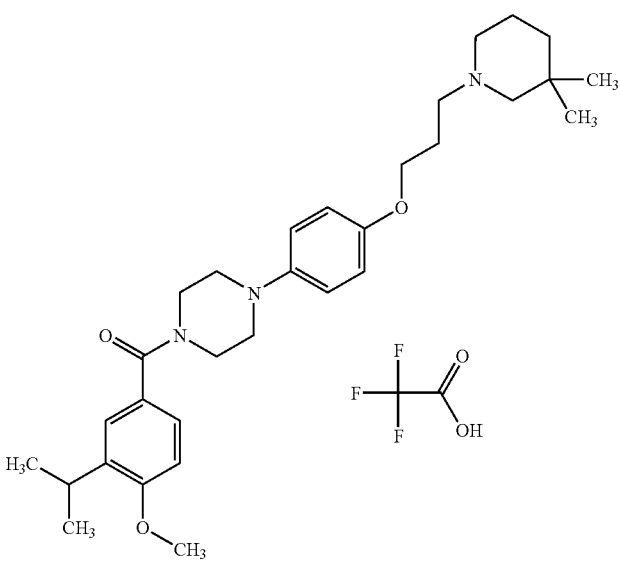 | 2.40 | 508 |
| 207 | 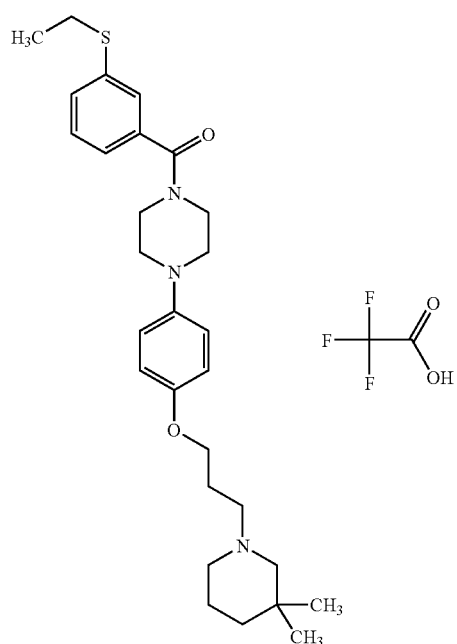 | 2.37 | 496 |

-continued
| Example | Structure | RT (min) | Mass Ion (M + H)+ |
|---|---|---|---|
| 208 | 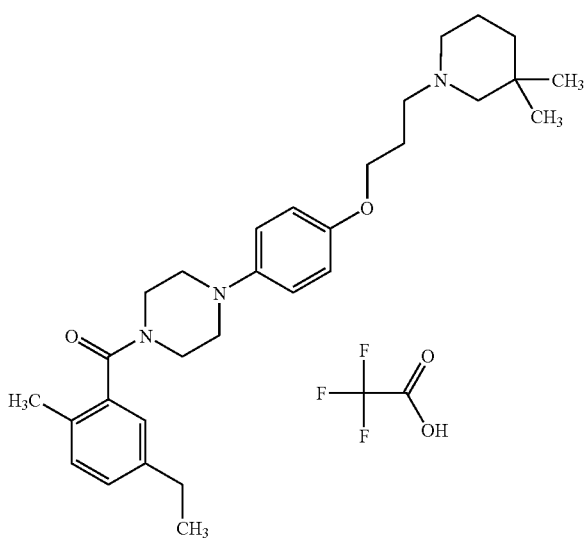 | 2.35 | 478 |
| 209 | 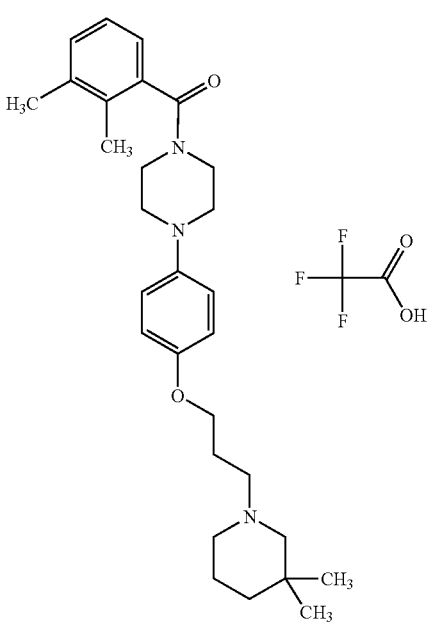 | 2.27 | 464 |

| Example | Structure | RT (min) | Mass Ion (M + H)+ |
|---|---|---|---|
| 210 | 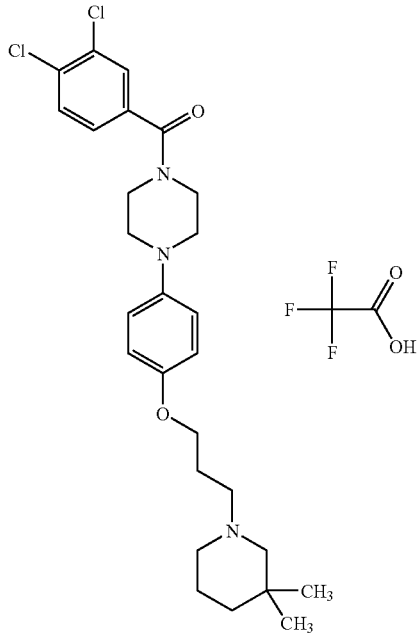 | 2.37 | 504 506 |
| 211 | 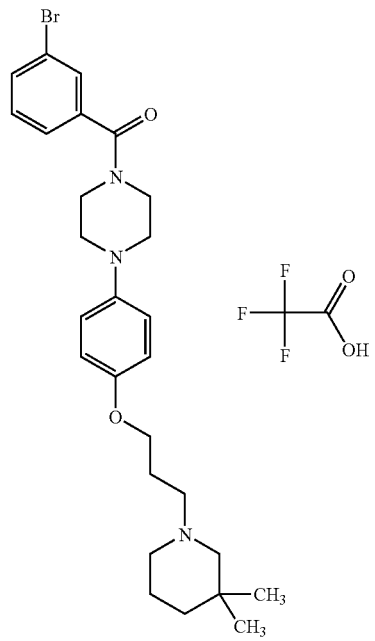 | 2.26 | 514 516 |

-continued
| Example | Structure | RT (min) | Mass Ion (M + H)+ |
|---|---|---|---|
| 212 | 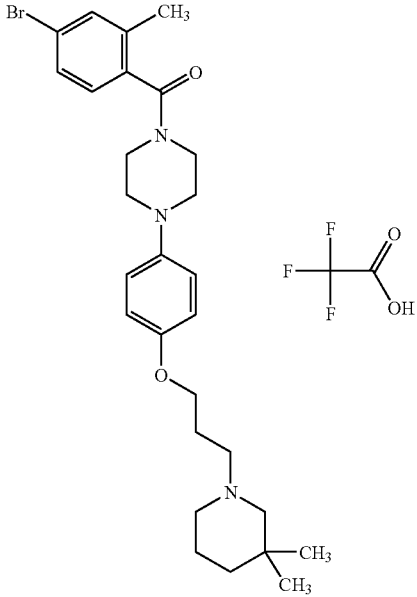 | 2.34 | 528 530 |
| 213 | 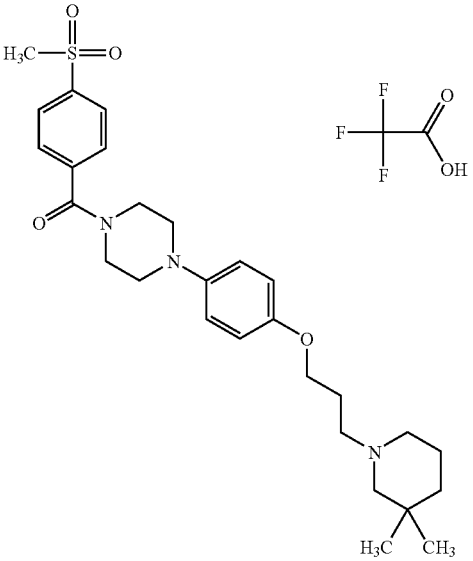 | 2.00 | 514 |
| 214 | 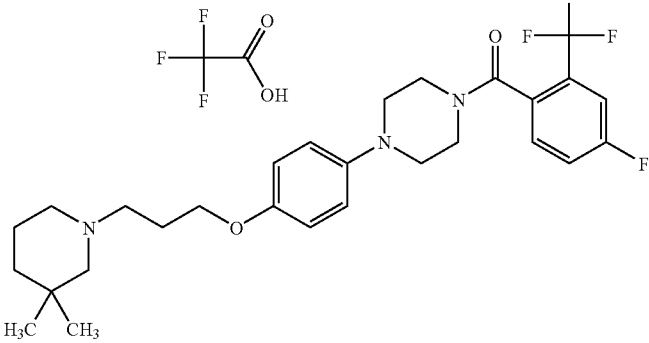 | 2.28 | 522 |

-continued
| Example | Structure | RT (min) | Mass Ion (M + H)+ |
|---|---|---|---|
| 215 | 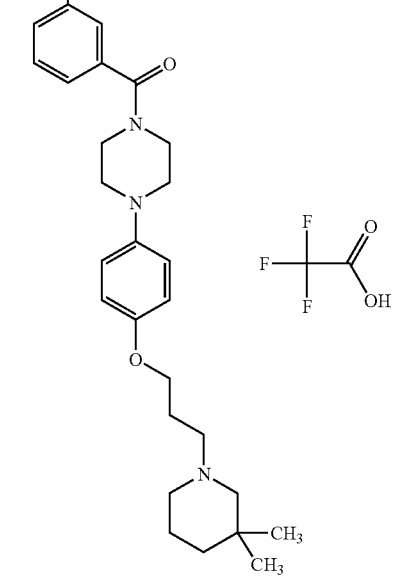 | 2.26 | 462 |
| 216 | 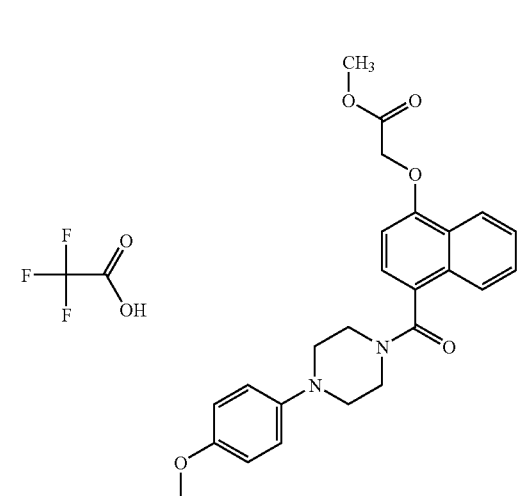 | 2.57 | 574 |

-continued

| Example | Structure | RT (min) | Mass Ion (M + H)+ |
|---|---|---|---|
| 217 | 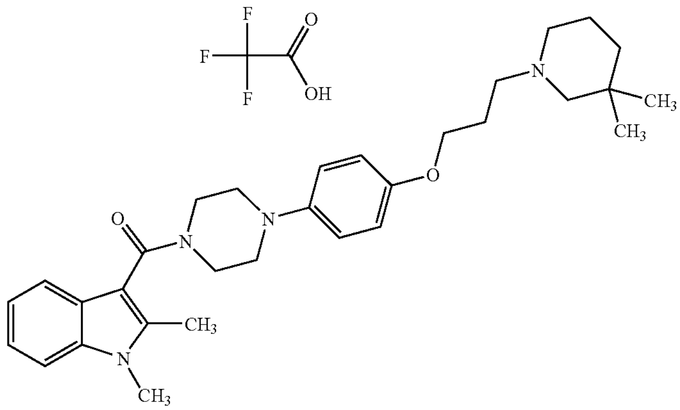 | 2.30 | 503 |
| 218 | 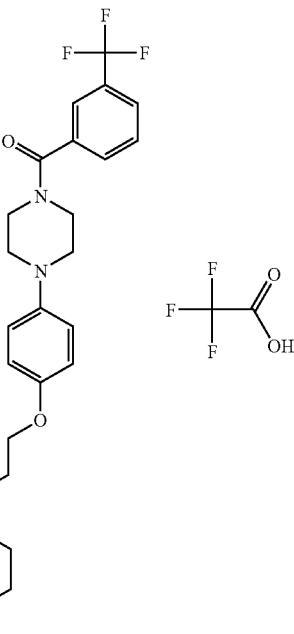 | 2.30 | 504 |

What is claimed is:

1. A compound of formula (I):

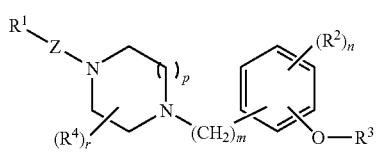

wherein:

R[1] represents phenyl optionally substituted by one or more substituents which may be the same or different and which are selected from the group consisting of: halogen; trifluoromethyl; —C$_{1-6}$ alkyl optionally substituted by COOR[15]; —C$_{1-6}$alkoxy optionally substituted by COOR[15]; hydroxy; oxo; cyano; —C$_{1-6}$alkyl-cyano; C$_{2-6}$ alkenyl optionally substituted by COOR[15]; C$_{3-7}$cycloalkyl; C$_{1-6}$alkylsulfonyl; C$_{2-6}$alkenoxy; C$_{1-6}$alkylthio; NR[15]R[16]; —C$_{1-6}$alkyl-aryl; aryl; —CO-aryl optionally substituted by halogen; —CO-heteroaryl; —CO-heterocyclyl; —COOR[15]; —COR[15]; —CONR[15]R[16]; and —C$_{1-6}$alkyl-CO-aryl groups; and in which R[15] and R[16] independently represent hydrogen, C$_{1-6}$alkyl or C$_{3-8}$cycloalkyl or together may be fused to form a 5- to 7-membered non-aromatic heterocyclic ring optionally interrupted by an O or S atom and optionally substituted by a halogen, C$_{1-6}$alkyl or C$_{1-6}$alkylC$_{1-6}$alkoxy group;

Z represents CO;

r is 0;

p is 1;

m is 0;

$R^3$ represents a group of formula (i):

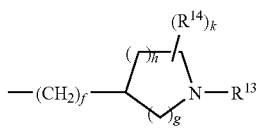

wherein
f is 0;
g is 2;
h is 1;
k is 0; and
$R^{13}$ represents $C_{1-6}$alkyl or $C_{3-8}$cycloalkyl;
or a pharmaceutically acceptable salt thereof.

2. A compound according to claim 1 wherein $R^1$ is phenyl optionally substituted by 1, 2 or 3 substituents which may be the same or different and which are selected from the group consisting of: chlorine, fluorine, bromine; trifluoromethyl; methyl, ethyl, isopropyl, propyl, t-butyl (optionally substituted by COOH, COOMe or COOEt); methoxy, butoxy, —OCH(Me)$_2$, —OC(Me)$_3$ (optionally substituted by COOH or COOMe); hydroxy; oxo; cyano; —CH$_2$—CN; ethenyl (optionally substituted by COOMe); cyclopentyl; —SO$_2$Me; —OCH$_2$CH=CH$_2$; —S-ethyl; N(Me)$_2$; benzyl; phenyl; —CO-phenyl (optionally substituted by chlorine); —CO-azetidinyl; —CO-tetrahydropyranyl; COOH, COOMe, COOt-butyl; —CO-methyl, —CO-ethyl, —CO-isopropyl, —CO-cyclopropyl, —CO-cyclobutyl, —CO-cyclopentyl, —CO-cyclohexyl; —CONH$_2$, —CO-pyrrolidinyl, —CO-morpholinyl, —CO-piperazinyl, —CO-piperidinyl, —CO-thiomorpholinyl (optionally substituted by methyl, fluorine and —CH$_2$OMe); or —CH$_2$COphenyl groups; or a pharmaceutically acceptable salt thereof.

3. A compound according to claim 1 wherein $R^1$ is phenyl substituted by $C_{1-6}$alkylsulfonyl.

4. A compound according to claim 1 wherein $R^1$ is phenyl substituted by SO$_2$Me.

5. A compound according to claim 1 wherein $R^1$ is phenyl substituted by SO$_2$Me at the para position.

6. A compound according to claim 1 wherein —O—$R^3$ is present at the para position of the phenyl group with respect to the rest of the compound.

7. A compound according to claim 1 wherein $R^{13}$ represents isopropyl, cyclopropyl or cyclobutyl.

8. A compound according to claim 3, wherein $R^{13}$ represents isopropyl, cyclopropyl or cyclobutyl.

9. A compound according to claim 4, wherein $R^{13}$ represents isopropyl, cyclopropyl or cyclobutyl.

10. A compound which is 1-(4-{[1-(1-methylethyl)-4-piperidinyl]oxy}phenyl)-4-{[4-(methylsulfonyl)phenyl]carbonyl}piperazine or a pharmaceutically acceptable salt thereof.

11. A pharmaceutical composition which comprises a compound of formula (I) as defined in claim 1 or a pharmaceutically acceptable salt thereof, and a pharmaceutically acceptable carrier or excipient.

12. A method of treatment of diseases of the upper respiratory tract which comprises administering to a human in need thereof an effective amount of a compound of formula (I) as defined in claim 1 or a pharmaceutically acceptable salt thereof.

13. A method of treatment according to claim 11 in which the disease is allergic rhinitis.

14. A pharmaceutical composition which comprises a compound of formula (I) as defined in claim 8 or a pharmaceutically acceptable salt thereof, and a pharmaceutically acceptable carrier or excipient.

15. A method of treatment of diseases of the upper respiratory tract which comprises administering to a human in need thereof an effective amount of a compound of formula (I) as defined in claim 8 or a pharmaceutically acceptable salt thereof.

16. A method of treatment according to claim 15 in which the disease is allergic rhinitis.

17. A pharmaceutical composition which comprises a compound of formula (I) as defined in claim 9 or a pharmaceutically acceptable salt thereof, and a pharmaceutically acceptable carrier or excipient.

18. A method of treatment of diseases of the upper respiratory tract which comprises administering to a human in need thereof an effective amount of a compound of formula (I) as defined in claim 9 or a pharmaceutically acceptable salt thereof.

19. A method of treatment according to claim 18 in which the disease is allergic rhinitis.

* * * * *